United States Patent
Leung et al.

(10) Patent No.: US 11,656,232 B2
(45) Date of Patent: May 23, 2023

(54) AGENTS AND METHODS FOR DIAGNOSING FISH ALLERGY

(71) Applicant: The Chinese University of Hong Kong, Hong Kong (CN)

(72) Inventors: Sze Yin Agnes Leung, Hong Kong (CN); Ting Fan Leung, Hong Kong (CN); Yat Hin Nicki Leung, Hong Kong (CN); Yee Yan Christine Wai, Hong Kong (CN)

(73) Assignee: The Chinese University of Hong Kong, Hong Kong (CN)

( * ) Notice: Subject to any disclaimer, the term of this patent is extended or adjusted under 35 U.S.C. 154(b) by 722 days.

(21) Appl. No.: 16/588,517

(22) Filed: Sep. 30, 2019

(65) Prior Publication Data
US 2020/0191797 A1 Jun. 18, 2020

Related U.S. Application Data

(60) Provisional application No. 62/740,289, filed on Oct. 2, 2018.

(51) Int. Cl.
G01N 33/68 (2006.01)
C12N 9/88 (2006.01)
C07K 14/76 (2006.01)

(52) U.S. Cl.
CPC ......... *G01N 33/6854* (2013.01); *C07K 14/76* (2013.01); *C12N 9/88* (2013.01); *C12Y 402/01011* (2013.01); *C07K 2319/60* (2013.01); *C07K 2319/61* (2013.01); *G01N 2800/24* (2013.01)

(58) Field of Classification Search
None
See application file for complete search history.

(56) References Cited

PUBLICATIONS

Kuehn et al.,"Identification of enolases and aldolases as important fish allergens in cod, salmon, and tuna: component resolved diagnosis using parvalbumin and the new allergens", Clinical et Experimental Allergy 43: 811-822 (Year: 2013).*
Ruethers et al.,"Seafood allergy: A comprehensive review of fish and shellfish allergens", Molecular Immunology 100: 28-57 (available online May 2018) (Year: 2018).*
GenBank A0A162BDB6_CTEID 364 amino acid sequence (Year: 2016).*
Aalberse, et al. "Molecular Allergen-Specific IgE Assays as a Complement to Allergen Extract-Based Sensitization Assessment." The Journal of Allergy and Clinical Immunology: In Practice 3, No. 6 (2015): 863-869.
Abramset al. "Oral food challenge outcomes in a pediatric tertiary care center." Allergy, Asthma & Clinical Immunology 13, No. 1 (2017): 43.
Alvares, et al. "Misdiagnosed food allergy resulting in severe malnutrition in an infant." Pediatrics 132, No. 1 (2013): e229-e232.
Asero, et al. "True monosensitivity to a tropical sole." Allergy (Copenhagen) 54, No. 11 (1999): 1228-1229.
Bird, et al. "Food allergen panel testing often results in misdiagnosis of food allergy." The Journal of pediatrics 166, No. 1 (2015): 97-100.
Borres, et al. "Recent advances in component resolved diagnosis in food allergy." Allergology International 65, No. 4 (2016): 378-387.
Bublin, et al. "IgE sensitization profiles toward green and gold kiwifruits differ among patients allergic to kiwifruit from 3 European countries." Journal of Allergy and Clinical Immunology 114, No. 5 (2004): 1169-1175.
Domínguez, et al. "Gad c 1 efficiency in the diagnosis of fish allergy in children." Clinical and translational allergy 3, No. S3 (2013): P54.
Ebo, et al. "Monosensitivity to pangasius and tilapia caused by allergens other than parvalbumin." Journal of investigational allergology & clinical immunology: official organ of the International Association of Asthmology (INTERASMA) and Sociedad Latinoamericana de Alergia e Inmunologia/International Association of Asthmology.—Barcelona 20, No. 1 (2010): 84-88.
Fernández-Rivas, et al. "Apple allergy across Europe: how allergen sensitization profiles determine the clinical expression of allergies to plant foods." Journal of Allergy and Clinical Immunology 118, No. 2 (2006): 481-488.
Komata, et al. "Usefulness of wheat and soybean specific IgE antibody titers for the diagnosis of food allergy." Allergology International 58, No. 4 (2009): 599-603.
Kuehn, et al. "Important variations in parvalbumin content in common fish species a factor possibly contributing to variable allergenicity." International archives of allergy and immunology 153, No. 4 (2010): 359-366.
Kuehn, et al. "Fish allergens at a glance: variable allergenicity of parvalbumins, the major fish allergens." Frontiers in immunology 5 (2014): 179.
Kuehn, et al. "Clinical monosensitivity to salmonid fish linked to specific IgE-epitopes on salmon and trout beta-parvalbumins." Allergy 66, No. 2 (2011): 299-301.
Kuehn, et al. "Identification of enolases and aldolases as important fish allergens in cod, salmon and tuna: component resolved diagnosis using parvalbumin and the new allergens." Clinical & Experimental Allergy 43, No. 7 (2013): 811-822.
Leung, et al. "Quality-of-life assessment in Chinese families with food-allergic children." Clinical & Experimental Allergy 39, No. 6 (2009): 890-896.

(Continued)

*Primary Examiner* — Anand U Desai
(74) *Attorney, Agent, or Firm* — Kilpatrick Townsend & Stockton LLP

(57) ABSTRACT

The present invention provides novel allergens isolated from grass carp *Ctenopharyngodon idella*, recombinant or modified polypeptides comprising such allergens, nucleic acids encoding the polypeptides as well as related compositions. Also provided are methods and kits for diagnosing fish allergy.

20 Claims, 15 Drawing Sheets
Specification includes a Sequence Listing.

(56) References Cited

PUBLICATIONS

Lieberman, t al. "The utility of peanut components in the diagnosis of IgE-mediated peanut allergy among distinct populations." The Journal of Allergy and Clinical Immunology: In Practice 1, No. 1 (2013): 75-82.

Luengo, et al. "Component resolved diagnosis: when should it be used?." Clinical and translational allergy 4, No. 1 (2014): 28.

Mehta, et al. "Growth and nutritional concerns in children with food allergy." Current opinion in allergy and clinical immunology 13, No. 3 (2013): 275.

Needham, et al. "The consumption of fish and fish products in the Asia-Pacific region based on household surveys." Bangkok, FAO Regional Office for Asia and the Pacific (2015).

Novembre, et al. "Correlation of anti-Pru p 3 IgE levels with severity of peach allergy reactions in children." Annals of Allergy, Asthma & Immunology 108, No. 4 (2012): 271-274.

Okada, et al. "Accurate determination of childhood food allergy prevalence and correction of unnecessary avoidance." Allergy, asthma & immunology research 9, No. 4 (2017): 322-328.

Osterballe, et al. "Threshold levels in food challenge and specific IgE in patients with egg allergy: is there a relationship?." Journal of allergy and clinical immunology 112, No. 1 (2003): 196-201.

Pawankar, "Allergic diseases and asthma: a global public health concern and a call to action." (2014): 1.

Rolinck-Werninghaus, et al. "Outcome of oral food challenges in children in relation to symptom-eliciting allergen dose and allergen-specific I g E." Allergy 67, No. 7 (2012): 951-957.

Sampson, et al. "Standardizing double-blind, placebo-controlled oral food challenges: American Academy of Allergy, Asthma & Immunology—European Academy of Allergy and Clinical Immunology PRACTALL consensus report." Journal of Allergy and Clinical Immunology 130, No. 6 (2012): 1260-1274.

Schulkes, et al. "Specific IgE to fish extracts does not predict allergy to specific species within an adult fish allergic population." Clinical and translational allergy 4, No. 1 (2014): 27.

Sharp, et al. "Fish allergy: in review." Clinical reviews in allergy & immunology 46, No. 3 (2014): 258-271.

Sicherer, et al. "Food allergy: epidemiology, pathogenesis, diagnosis, and treatment." Journal of Allergy and Clinical Immunology 133, No. 2 (2014): 291-307.

Soares-Weiser, et al. "The diagnosis of food allergy: a systematic review and meta-analysis." Allergy 69, No. 1 (2014): 76-86.

Stensgaard, et al. "Quality of life in childhood, adolescence and adult food allergy: patient and parent perspectives." Clinical & Experimental Allergy 47, No. 4 (2017): 530-539.

Swoboda, et al. "Recombinant carp parvalbumin, the major cross-reactive fish allergen: a tool for diagnosis and therapy of fish allergy." The Journal of Immunology 168, No. 9 (2002): 4576-4584.

Tuano, et al. "Utility of component-resolved diagnostics in food allergy." Current allergy and asthma reports 15, No. 6 (2015): 32.

Van Do, et al. "Allergy to fish parvalbumins: studies on the cross-reactivity of allergens from 9 commonly consumed fish." Journal of Allergy and Clinical Immunology 116, No. 6 (2005): 1314-1320.

Vázquez-Cortés, et al. "Selective allergy to the salmonidae fish family: a selective parvalbumin epitope?." Annals of allergy, asthma, & immunology 108, No. 1 (2012): 62-63.

* cited by examiner

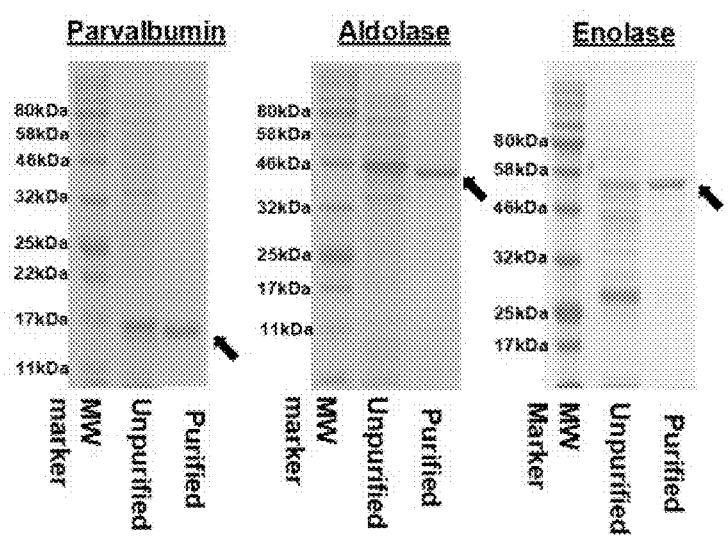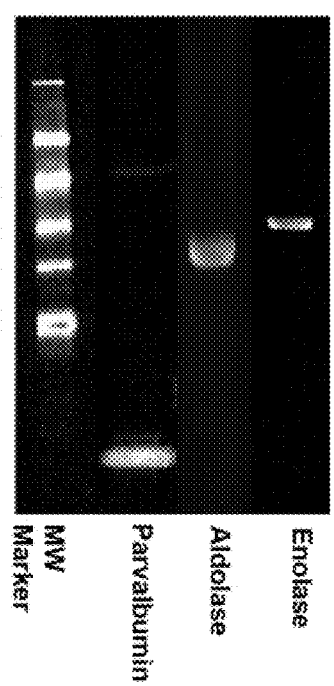

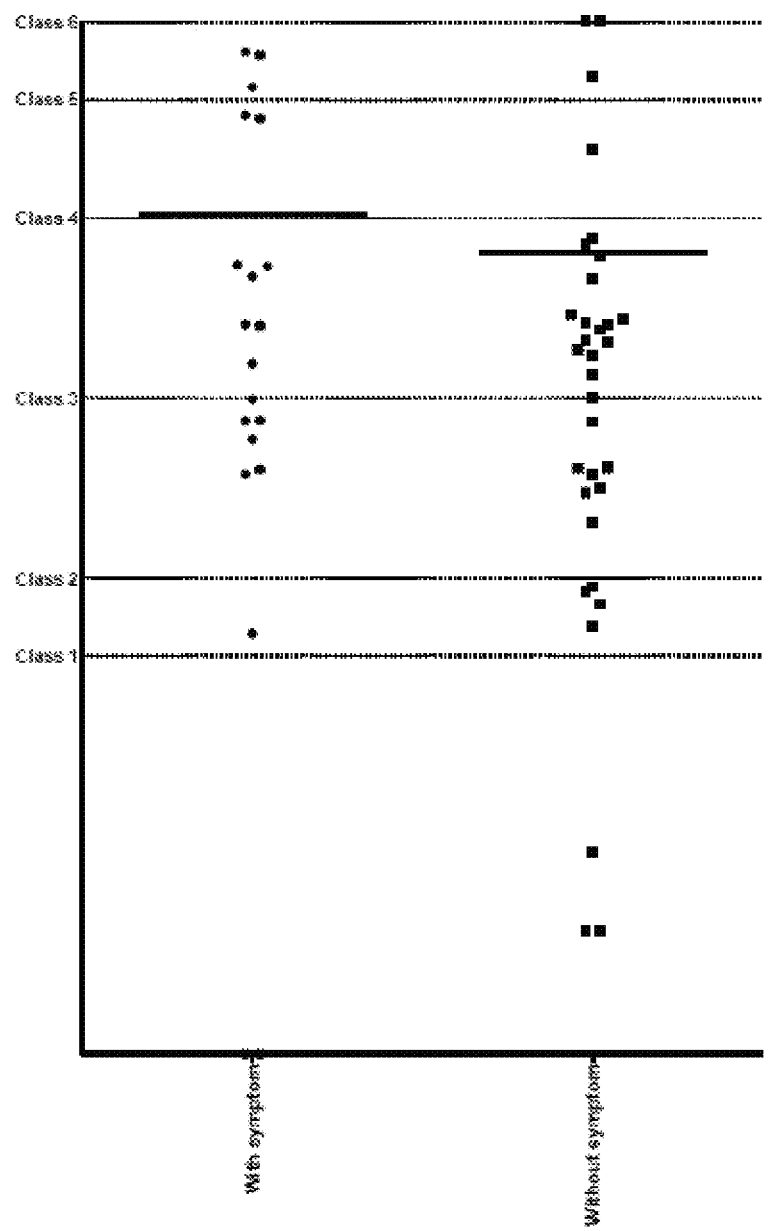

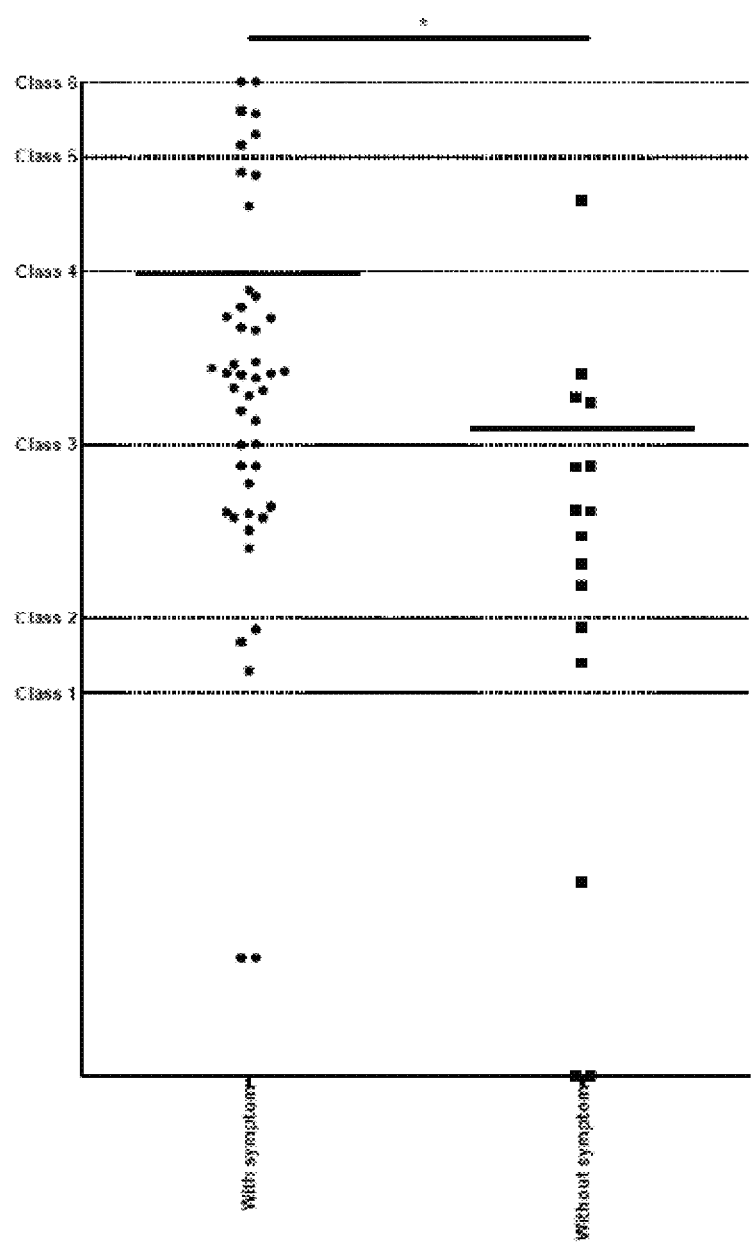

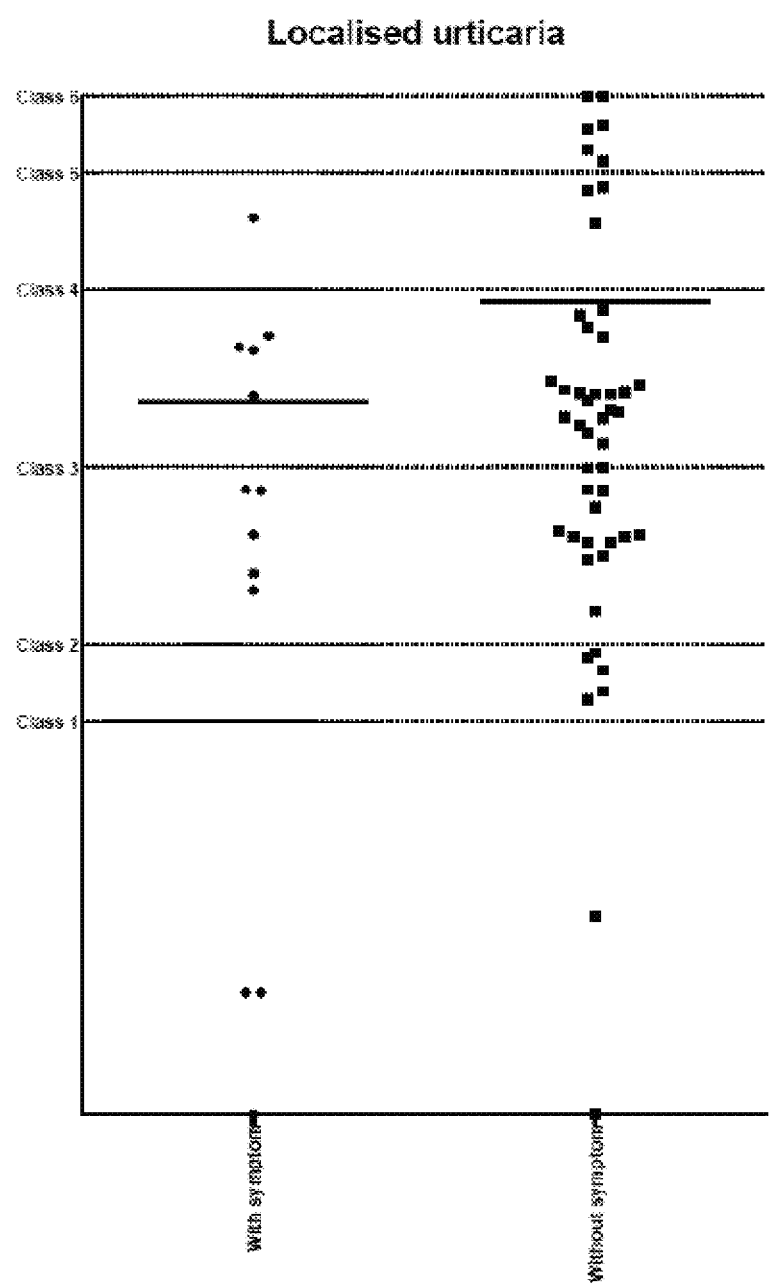

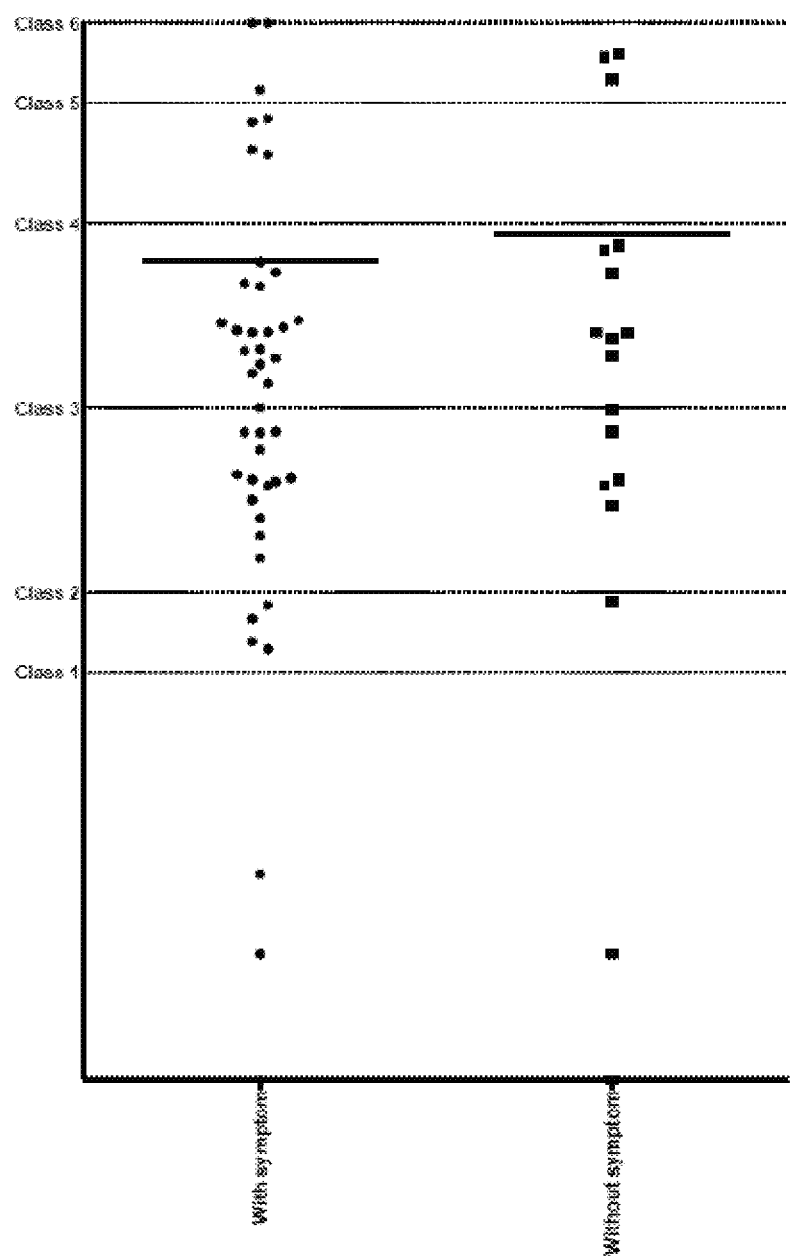

AGENTS AND METHODS FOR DIAGNOSING FISH ALLERGY

This application claims priority to U.S. Provisional Patent Application No. 62/740,289, filed Oct. 2, 2018, the contents of which are hereby incorporated by reference in the entirety for all purposes.

BACKGROUND OF THE INVENTION

Sequence Listing

The instant application contains a Sequence Listing which has been filed electronically in ASCII format and is hereby incorporated by reference in its entirety. Said ASCII copy, created on Nov. 7, 2019, is named 080015-1156166-025810US_SL.txt and is 37,229 bytes in size.

BACKGROUND OF THE INVENTION

Allergies to various fish species are among the most common food allergies in China as well as in other countries in Asia and in Europe. A fish allergy, in contrast to a shellfish allergy, is one in which one's immune system reacts abnormally to a finned fish such as tuna, halibut, or salmon. It is a form of food allergy that affects women more than men and adults more than children. Fish allergies often develop during early childhood but, in contrast to a milk or egg allergy, usually persists well beyond school age.

Fish allergies are more prevalent in areas where fish is a predominant part of the local diet, such as parts of southeast Asia and Scandinavia. Symptoms can range from mild to severe and may include skin rashes, respiratory symptoms, and gastrointestinal distress, for example, hives or a skin rash, generalized itching, stuffy nose and sneezing (allergic rhinitis), headaches, breathing difficulty (asthma), indigestion and stomach pain, belching, bloating, or flatulence, diarrhea, nausea or vomiting can result. In some people, a fish allergy may turn severe and lead the rapid development of anaphylaxis, a potentially deadly, whole-body reaction characterized by widespread rash, facial and tongue swelling, wheezing, shortness of breath, rapid heart rate, delirium, and a feeling of impending doom. A fish allergy may not only be triggered by eating fish but by touching fish or objects used to prepare or contain fish, consuming foods in which fish byproducts are used, or by simply inhaling air in an environment when fish was cooked.

While a fish allergy can often be diagnosed with a blood test or a minimally invasive skin-prick test, a strict avoidance of fish and fish-contaminated environment is the best means of protection. Antihistamines or corticosteroids may be used to relieve mild symptoms.

The currently available commercial diagnostic methods for detecting fish allergies have significant limitations in both sensitivity and specificity depending on the fish species one might be allergic to. As such, there remains a distinct need in the field for new and effective methods for detection of allergies induced by a broad spectrum of fish species. The present invention fulfills this and other related needs.

BRIEF SUMMARY OF THE INVENTION

The present inventors have identified novel allergens of grass carp *Ctenopharyngodon idella*, namely β-parvalbumin, β-enolase, and aldolase A, which are useful as diagnostic markers for detecting fish allergies in patients. Thus, in one aspect, the present disclosure provides an isolated polypeptide comprising the amino acid sequence set forth in any one of SEQ ID NOs:1-3. The polypeptide is optionally conjugated with a heterologous moiety: for instance, the polypeptide can also include one or more heterologous amino acid sequences located at the N-terminus and/or the C-terminus of the amino acid sequence of SEQ ID NO: 1, 2, or 3, such as one or more peptide tag sequences that can facilitate isolation, identification, or detection of the fusion polypeptide (e.g., an epitope tag or 6× His tag) (SEQ ID NO: 4). In some embodiments, the heterologous moiety is a detectable label. In some embodiments, the heterologous moiety is a solid substrate, such as the solid surface of a plate or an array suitable for use in an immunoassay.

In another aspect, this invention provides an isolated nucleic acid comprising a polynucleotide sequence encoding a novel *C. idella* allergen of this invention (e.g., a polypeptide comprising or consisting of SEQ ID NO: 1, 2, or 3) or its fusion proteins described above and herein. For instance, the nucleic acid may comprise a polynucleotide sequence encoding the amino acid sequence of any one of SEQ ID NOs: 1-3 and one or more heterologous nucleotide sequences (e.g., encoding one or more heterologous amino acid sequences). In some embodiments, provided herein is an expression cassette comprising the polynucleotide sequence disclosed herein operably linked to a promoter, e.g., a heterologous promoter or a promoter that in nature does not direct the transcription of any one of the *C. idella* β-parvalbumin, β-enolase, and aldolase A genes.

In some embodiments, the nucleic acid is in the form of a vector comprising a polynucleotide sequence encoding the novel *C. idella* allergen or its fusion protein of this invention (e.g., a polypeptide comprising or consisting of SEQ ID NO: 1, 2, or 3) or comprising an expression cassette that comprises the polynucleotide sequence operably linked to a promoter, especially a heterologous promoter.

In yet other aspects, this invention provides a host cell that comprises the nucleic acid or the expression cassette or the vector described above and herein that can direct the transcription and translation of a polypeptide comprising or consisting of the amino acid sequence of SEQ ID NO:1, 2, or 3. Also provided is a method of recombinantly producing a polypeptide in such host cells by culturing the host cells under conditions that are permissible for the expression of a polypeptide comprising or consisting of the amino acid sequence of any one of SEQ ID NOs:1-3, in which the novel *C. idella* allergen is optionally fused to at least one, possibly more, heterologous peptide sequence. A Host cell comprising the recombinant polypeptide is therefore also provided. In some embodiments, the present disclosure provides a composition comprising the polypeptide or the nucleic acid described herein, optionally two or three of such polypeptides or nucleic acids, and a physiologically acceptable excipient.

In another aspect, the present invention provides a method for detecting fish allergy in a subject who is suspected of suffering from fish allergy, for example, who may have been exposed to fish or fish-contaminated substance or environment and who is experiencing one or more symptoms such as hives, skin rash, nausea, stomach cramps, indigestion, vomiting, diarrhea, stuffy or runny nose, sneezing, headache, asthma, and anaphylaxis. The method includes these steps: (1) contacting a serum or plasma sample taken from the subject with a polypeptide comprising or consisting of any one of SEQ ID NOs: 1-3; (2) detecting in the sample presence of an IgE antibody that specifically binds to the polypeptide; and (3) determining the subject as likely suffering from fish allergy.

In some embodiments, the polypeptide used in step (1) is conjugated to a solid support, such as the surface of a plate or an array suitable for use in an immunoassay. In some embodiments, the polypeptide comprises or consists of the amino acid sequence of SEQ ID NO: 1, where one or more heterologous peptide sequences may be present in the polypeptide. In some embodiments, the threshold for the IgE antibody level detected in step (2) is set at a level of 0.35 kUA/L or higher. In other words, when the IgE level is determined in step (2) as below 0.35 kUA/L, the test subject is ruled out as having a case of fish allergy. In some embodiments, an anti-IgE antibody is used in step (2) in order to determine the IgE level in the sample. The anti-IgE antibody is optionally conjugated to a detectable label to facilitate detection. In some embodiments, two or three polypeptides each comprising or consisting of a different amino acid sequence selected from SEQ ID NO:1, 2, or 3 are used in step (1). In some embodiments, the diagnostic method include a further treatment step, after step (3) where the test subject is found to likely suffer from a fish allergy, of administering to the subject an appropriate therapy for fish allergy, e.g., by administration of antihistamines, corticosteroids, or by immunotherapy such as sublingual immunotherapy.

A further aspect of this invention is a kit for diagnosing fish allergy, which includes a plurality of containers: a first container containing a polypeptide comprising or consisting of any one of SEQ ID NOs:1-3, possibly in the form of a fusion protein including one or more heterologous peptide sequences; and (ii) a second container containing a blood (e.g., serum or plasma) sample obtained from a control subject who is confirmed to have no fish allergy. In some embodiments, the polypeptide is conjugated to a solid support, such as the surface of an immunoassay plate. Optionally, two or three polypeptides each comprising a different amino acid sequence of SEQ ID NO: 1, 2, or 3 are included in the kit, and the polypeptides may be kept in the same container or each in a separate container. In some embodiments, one polypeptide comprising or consisting of SEQ ID NO: 1 is included in the kit, optionally it is conjugated to a solid support. In some embodiments, the kit also includes a third container containing an anti-IgE antibody, which is optionally conjugated to a detectable label for ease of detection.

In a related aspect, the present invention provides a use of the polypeptide comprising or consisting of the amino acid sequence of any one of SEQ ID NOs: 1-3 for manufacturing a kit for detecting fish allergy, which kit is described above and herein.

BRIEF DESCRIPTION OF THE DRAWINGS

FIGS. 1A-1B: (FIG. 1A) Purification of recombinant allergens parvalbumin (left), aldolase (middle) and enolase (right) using immobilized metal-chelate affinity chromatography. Arrow indicates purified parvalbumin, aldolase and enolase at 14 kDa, 40 kDa and 50 kDa respectively on a SDS-PAGE. Color pre-stained protein standard, broad range (New England Biolab) was used as the molecular weight marker. (FIG. 1B) Verification of allergen identity using immunoblotting with antibodies specific to the allergen. Lane 1, Genscript WB Master protein standard. Lane 2, recombinant parvalbumin probed with mouse monoclonal anti-parvalbumin antibody, clone PARV-19 (Sigma-Aldrich). Lane 3, recombinant aldolase probed with polyclonal anti-aldolase A antibody (Aviva Systems Biology). Lane 4, recombinant enolase probed with polyclonal anti-enolase 3 antibody (Lifespan).

FIGS. 4A-4J: IgE reactivity of subjects with or without the clinical symptoms of (FIG. 4A) anaphylaxis, (FIG. 4B) itchy throat, (FIG. 4C) angioedema, (FIG. 4D) localized urticaria, (FIG. 4E) generalized urticaria, (FIG. 4F) facial rash, (FIG. 4G) skin itchiness without rash, (FIG. 4H) vomiting or diarrhea, (FIG. 4I) abdominal pain, and (FIG. 4J) short of breath or wheeze.

(FIG. 6A) Cod parvalbumin inhibited IgE binding to *C. idella* parvalbumin for a maximum of 50% at 50 µg/ml; and (FIG. 6B) Reciprocally, *C. idella* parvalbumin inhibited IgE binding to cod parvalbumin by nearly 90% at 20 µg/ml. The inhibitory effect is identical to cod parvalbumin itself.

DEFINITIONS

Figure 2:
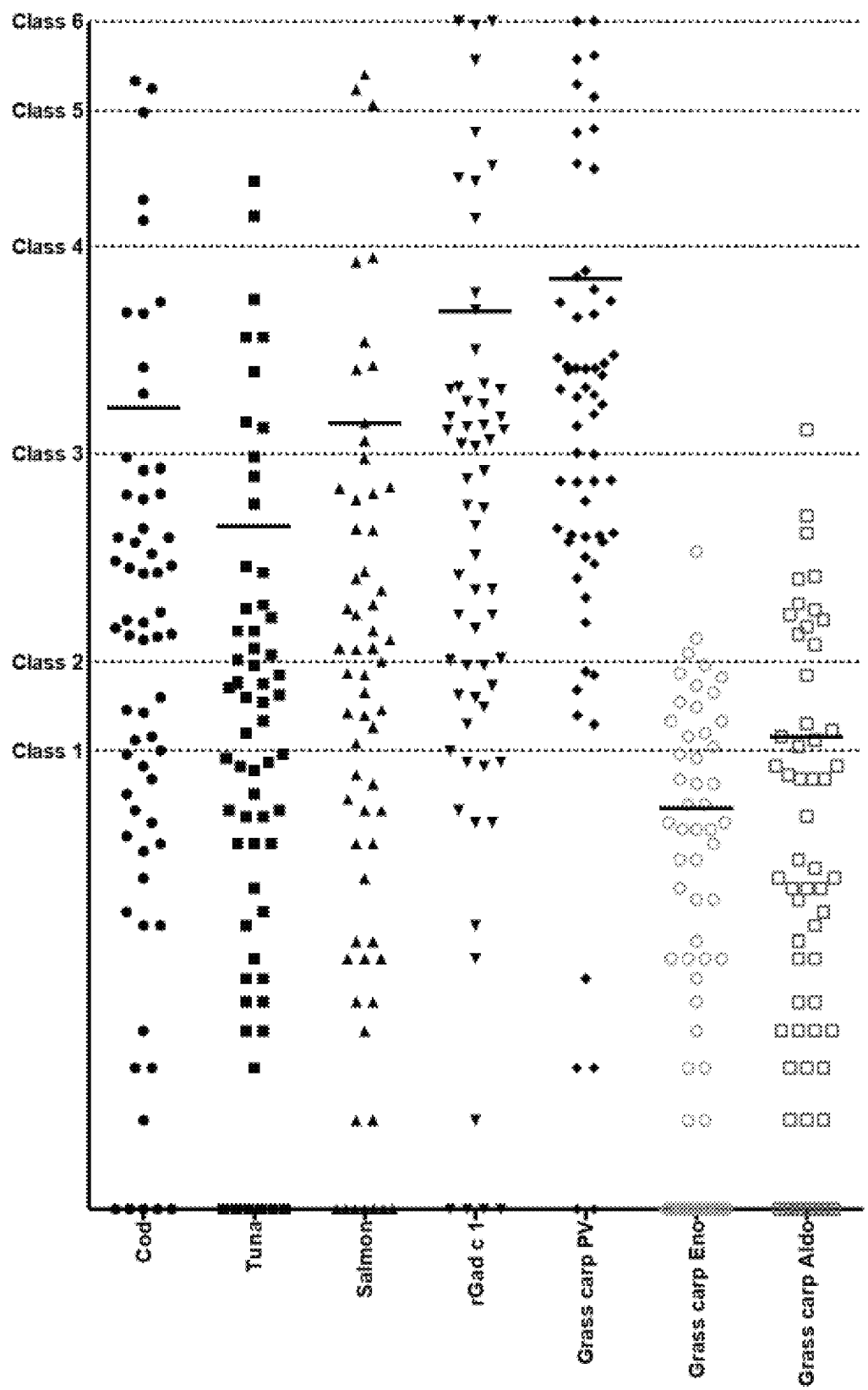
FIG. 2: IgE sensitization profile of 62 fish-allergic patients. sIgE levels of cod (f3), tuna (f40), salmon (f41) and rGad c 1 (f426) were measured by Phadia ImmunoCAP while IgE to grass carp allergens parvalbumin, enolase and aldolase were measured by standardized ELISA.

As used herein, the following terms have the meanings ascribed to them unless specified otherwise.

The terms "a," "an," or "the" as used herein not only include aspects with one member, but also include aspects with more than one member. For instance, the singular forms "a," "an," and "the" include plural referents unless the context clearly dictates otherwise. Thus, for example, reference to "a cell" includes a plurality of such cells and reference to "the agent" includes reference to one or more agents known to those skilled in the art, and so forth.

The terms "about" and "approximately" shall generally mean an acceptable degree of error for the quantity measured given the nature or precision of the measurements. Typical, exemplary degrees of error are within 20 percent (%), preferably within 10%, and more preferably within 5% of a given value or range of values. Alternatively, and particularly in biological systems, the terms "about" and "approximately" may mean values that are within an order of magnitude, preferably within 5-fold and more preferably within 2-fold of a given value. Numerical quantities given herein are approximate unless stated otherwise, meaning that the term "about" or "approximately" can be inferred when not expressly stated.

"β-parvalbumin, β-enolase, and aldolase A of grass carp *Ctenopharyngodon idella*" refer to three newly identified fish allergens having the amino acid sequences set forth in SEQ ID NO: 1, SEQ ID NO:2, and SEQ ID NO:3, respectively. The Uniprot No. for the aldolase A is A0A162BDB6 and the EMBL Accession No. is AKA64469.1.

The term "peptide," "polypeptide," and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers. As used herein, the terms encompass amino acid chains of any length, including peptides (i.e., epitopes), wherein the amino acid residues are linked by covalent peptide bonds.

The term "amino acid" includes naturally-occurring α-amino acids and their stereoisomers, as well as unnatural (non-naturally occurring) amino acids and their stereoisomers. "Stereoisomers" of amino acids refers to mirror image isomers of the amino acids, such as L-amino acids or D-amino acids. For example, a stereoisomer of a naturally-occurring amino acid refers to the mirror image isomer of the naturally-occurring amino acid, i.e., the D-amino acid.

Naturally-occurring amino acids are those encoded by the genetic code, as well as those amino acids that are later modified, e.g., hydroxyproline, γ-carboxyglutamate and O-phosphoserine. Naturally-occurring α-amino acids include, without limitation, alanine (Ala), cysteine (Cys), aspartic acid (Asp), glutamic acid (Glu), phenylalanine (Phe), glycine (Gly), histidine (His), isoleucine (Ile), arginine (Arg), lysine (Lys), leucine (Leu), methionine (Met), asparagine (Asn), proline (Pro), glutamine (Gln), serine (Ser), threonine (Thr), valine (Val), tryptophan (Trp), tyrosine (Tyr), and combinations thereof. Stereoisomers of a naturally-occurring α-amino acids include, without limitation, D-alanine (D-Ala), D-cysteine (D-Cys), D-aspartic acid (D-Asp), D-glutamic acid (D-Glu), D-phenylalanine (D-Phe), D-histidine (D-His), D-isoleucine (D-Ile), D-arginine (D-Arg), D-lysine (D-Lys), D-leucine (D-Leu), D-methionine (D-Met), D-asparagine (D-Asn), D-proline (D-Pro), D-glutamine (D-Gln), D-serine (D-Ser), D-threonine (D-Thr), D-valine (D-Val), D-tryptophan (D-Trp), D-tyrosine (D-Tyr), and combinations thereof.

Unnatural (non-naturally occurring) amino acids include, without limitation, amino acid analogs, amino acid mimetics, synthetic amino acids, N-substituted glycines, and N-methyl amino acids in either the L- or D-configuration that function in a manner similar to the naturally-occurring amino acids. For example, "amino acid analogs" are unnatural amino acids that have the same basic chemical structure as naturally-occurring amino acids, i.e., an α carbon that is bound to a hydrogen, a carboxyl group, an amino group, but have modified R (i.e., side-chain) groups or modified peptide backbones, e.g., homoserine, norleucine, methionine sulfoxide, methionine methyl sulfonium. "Amino acid mimetics" refer to chemical compounds that have a structure that is different from the general chemical structure of an amino acid, but that functions in a manner similar to a naturally-occurring amino acid.

Amino acids may be referred to herein by either the commonly known three letter symbols or by the one-letter symbols recommended by the IUPAC-IUB Biochemical Nomenclature Commission. Nucleotides, likewise, may be referred to by their commonly accepted single-letter codes.

With respect to amino acid sequences, one of skill in the art will recognize that individual substitutions, additions, or deletions to a peptide, polypeptide, or protein sequence which alters, adds, or deletes a single amino acid or a small percentage of amino acids in the encoded sequence is a "conservatively modified variant" where the alteration results in the substitution of an amino acid with a chemically similar amino acid. The chemically similar amino acid includes, without limitation, a naturally-occurring amino acid such as an L-amino acid, a stereoisomer of a naturally occurring amino acid such as a D-amino acid, and an unnatural amino acid such as an amino acid analog, amino acid mimetic, synthetic amino acid, N-substituted glycine, and N-methyl amino acid.

Conservative substitution tables providing functionally similar amino acids are well known in the art. For example, substitutions may be made wherein an aliphatic amino acid (e.g., G, A, I, L, or V) is substituted with another member of the group. Similarly, an aliphatic polar-uncharged group such as C, S, T, M, N, or Q, may be substituted with another member of the group; and basic residues, e.g., K, R, or H, may be substituted for one another. In some embodiments, an amino acid with an acidic side chain, e.g., E or D, may be substituted with its uncharged counterpart, e.g., Q or N, respectively; or vice versa. Each of the following eight groups contains other exemplary amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

The term "amino acid modification" or "amino acid alteration" refers to a substitution, a deletion, or an insertion of one or more amino acids.

The term "nucleic acid," "nucleotide" or "polynucleotide" refers to deoxyribonucleic acids (DNA) or ribonucleic acids (RNA) and polymers thereof in either single-, double- or multi-stranded form. The term includes, but is not limited to, single-, double- or multi-stranded DNA or RNA, genomic DNA, cDNA, DNA-RNA hybrids, or a polymer comprising purine and/or pyrimidine bases or other natural, chemically modified, biochemically modified, non-natural, synthetic or derivatized nucleotide bases. Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), orthologs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991), Ohtsuka et al., *J. Biol. Chem.* 260:2605-2608 (1985), and Rossolini et al., *Mol. Cell. Probes* 8:91-98 (1994)). The term nucleic acid is used interchangeably with gene, cDNA, and mRNA encoded by a gene.

The term "nucleotide sequence encoding a polypeptide" or "gene" means the segment of DNA involved in producing a polypeptide chain, it includes regions preceding and following the coding region (leader and trailer) involved in the transcription/translation of the gene product and the regulation of the transcription/translation, as well as intervening sequences (introns) between individual coding segments (exons). The leader, the trailer as well as the introns include regulatory elements that are necessary during the transcription and the translation of a gene (e.g., promoters, terminators, translational regulatory sequences such as ribosome binding sites and internal ribosome entry sites, enhancers, silencers, insulators, boundary elements, replication origins, matrix attachment sites and locus control regions, etc.). A "gene product" can refer to either the mRNA or protein expressed from a particular gene.

"Percentage of sequence identity" is determined by comparing two optimally aligned sequences over a comparison window, wherein the portion of the sequence (e.g., a peptide of the invention) in the comparison window may comprise additions or deletions (i.e., gaps) as compared to the reference sequence which does not comprise additions or deletions, for optimal alignment of the two sequences. The percentage is calculated by determining the number of positions at which the identical amino acid residue occurs in both sequences to yield the number of matched positions, dividing the number of matched positions by the total number of positions in the window of comparison and multiplying the result by 100 to yield the percentage of sequence identity.

The term "percent identity" or "percent sequence identity," in the context of describing two or more polynucleotide or amino acid sequences, refer to two or more sequences or subsequences that are the same or have a specified percentage of amino acid residues or nucleotides that are the same (for example, a variant of a peptide of interest used in the method of this invention has at least 80% sequence identity, preferably 85%, 90%, 91%, 92%, 93, 94%, 95%, 96%, 97%, 98%, 99%, or 100% identity, to a reference sequence, e.g., a corresponding epitope or antigen, when compared and aligned for maximum correspondence over a comparison window, or designated region as measured using one of the following sequence comparison algorithms or by manual alignment and visual inspection. Such sequences are then said to be "substantially identical." With regard to polynucleotide sequences, this definition also refers to the complement of a test sequence. Preferably, the identity exists over a region that is at least about 8 amino acids in length, or more preferably over a region that is at least 8-25 or at least 8 to 12 amino acids in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. For sequence comparison of nucleic acids and proteins, the BLAST and BLAST 2.0 algorithms and the default parameters discussed below are used.

Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

Additional examples of algorithms that are suitable for determining percent sequence identity and sequence similarity are the BLAST and BLAST 2.0 algorithms, which are described in Altschul et al., (1990) *J. Mol. Biol.* 215: 403-410 and Altschul et al. (1977) *Nucleic Acids Res.* 25: 3389-3402, respectively. Software for performing BLAST analyses is publicly available at the National Center for Biotechnology Information website, ncbi.nlm.nih.gov. The algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits acts as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word size (W) of 28, an expectation (E) of 10, M=1, N=−2, and a comparison of both strands. For amino acid sequences, the BLASTP program uses as defaults a word size (W) of 3, an expectation (E) of 10, and the BLOSUM62 scoring matrix (see, e.g., Henikoff and Henikoff, *Proc. Natl. Acad. Sci. USA* 89:10915 (1989)).

The BLAST algorithm also performs a statistical analysis of the similarity between two sequences (see, e.g., Karlin and Altschul, *Proc. Nat'l. Acad. Sci. USA,* 90: 5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or peptides are substantially identical is that the peptide encoded by the first nucleic acid is immunologically cross reactive with the antibodies raised against the peptide encoded by the second nucleic acid. Thus, a peptide is typically substantially identical to a second peptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

The terms "transfection" or "transfected" refer to introduction of a nucleic acid into a cell by non-viral or viral-based methods. The nucleic acid molecules may be gene sequences encoding complete proteins or functional portions thereof. See, e.g., Sambrook et al., 1989, Molecular Cloning: A Laboratory Manual, 18.1-18.88.

The term "expression" or "expressed" in the context of a gene refers to the transcriptional and/or translational product of the gene. The level of expression of a DNA molecule in a cell may be determined on the basis of either the amount of corresponding mRNA that is present within the cell or the amount of protein encoded by that DNA produced by the cell.

Expression of a transfected gene can occur transiently or stably in a cell. During "transient expression" the transfected gene is not transferred to the daughter cell during cell division. Since its expression is restricted to the transfected cell, expression of the gene is lost over time. In contrast, stable expression of a transfected gene can occur when the gene is co-transfected with another gene that confers a selection advantage to the transfected cell. Such a selection advantage may be a resistance towards a certain toxin that is presented to the cell.

The term "promoter," as used herein, refers to a polynucleotide sequence capable of driving transcription of a coding sequence in a cell. Thus, promoters used in the polynucleotide constructs of the invention include cis-acting transcriptional control elements and regulatory sequences that are involved in regulating or modulating the timing and/or rate of transcription of a gene. For example, a promoter can be a cis-acting transcriptional control element, including an enhancer, a promoter, a transcription terminator, an origin of replication, a chromosomal integration sequence, 5' and 3' untranslated regions, or an intronic sequence, which are involved in transcriptional regulation. These cis-acting sequences typically interact with proteins or other biomolecules to carry out (turn on/off, regulate, modulate, etc.) gene transcription. A "constitutive promoter" is one that is capable of initiating transcription in nearly all tissue types, whereas a "tissue-specific promoter" initiates transcription only in one or a few particular tissue types. An "inducible promoter" is one that initiates transcription only under particular environmental conditions or developmental conditions.

A polynucleotide/polypeptide sequence is "heterologous" to an organism or a second polynucleotide/polypeptide sequence if it originates from a different species, or, if from the same species, is modified from its original form. For example, when a promoter is said to be operably linked to a heterologous coding sequence, it means that the coding sequence is derived from one species whereas the promoter sequence is derived another, different species; or, if both are derived from the same species, the coding sequence is not naturally associated with the promoter (e.g., is a genetically engineered coding sequence, or from a different gene in the same species).

Nucleic acid or amino acid sequences are "operably linked" (or "operatively linked") when placed into a functional relationship with one another. For instance, a promoter or enhancer is operably linked to a coding sequence if it regulates, or contributes to the modulation of, the transcription of the coding sequence. Operably linked DNA sequences are typically contiguous, and operably linked amino acid sequences are typically contiguous and in the same reading frame. However, since enhancers generally function when separated from the promoter by up to several kilobases or more and intronic sequences may be of variable lengths, some polynucleotide elements may be operably linked but not contiguous. Similarly, certain amino acid sequences that are non-contiguous in a primary polypeptide sequence may nonetheless be operably linked due to, for example folding of a polypeptide chain.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. For example, recombinant cells express genes that are not found within the native (non-recombinant) form of the cell or express native genes that are otherwise abnormally expressed, under-expressed, or not expressed at all.

An "expression cassette" refers to a nucleic acid construct, which when introduced into a host cell, results in transcription and/or translation of a RNA or polypeptide, respectively. Antisense constructs or sense constructs that are not or cannot be translated are expressly included by this definition. One of skill will recognize that the inserted polynucleotide sequence need not be identical, but may be only substantially similar to a sequence of the gene from which it was derived.

The term "vector" or "recombinant expression vector" refers a nucleic acid construct, generated recombinantly or synthetically, with a series of specified nucleic acid elements that permit transcription of a particular polynucleotide sequence in a host cell. An expression vector may be part of a plasmid, viral genome, or nucleic acid fragment. Typically, an expression vector includes a polynucleotide to be transcribed, operably linked to a promoter. "Operably linked" in this context means two or more genetic elements, such as a polynucleotide coding sequence and a promoter, placed in relative positions that permit the proper biological functioning of the elements, such as the promoter directing transcription of the coding sequence.

The term "allergen" refers not only to naturally occurring allergen extracts and allergen molecules but also to mutants of allergens, hypoallergens or parts of allergen molecules, such as polypeptides. Allergens are able to trigger an allergy, that is, an immediate-type hypersensitivity reaction, which is induced by the synthesis of IgE antibodies. Hypoallergens are natural or recombinant derivatives of an allergen molecule which, due to slight differences compared with the amino acid sequence of the allergen, assume a conformation by which IgE-binding properties are lost.

A "label," "detectable label," or "detectable moiety" is a composition detectable by radiological, spectroscopic, photochemical, biochemical, immunochemical, chemical, or other physical means. For example, useful labels include radioisotopes such as $^{32}P$, fluorescent dyes, electron-dense reagents, enzymes (e.g., as commonly used in an ELISA), biotin, digoxigenin, or haptens and proteins that can be made detectable, e.g., by incorporating a radioactive component into a polypeptide or used to detect antibodies specifically reactive with the polypeptide. Typically a detectable label is a heterologous moiety attached to a probe or a molecule (e.g., a protein or nucleic acid) with defined binding characteristics (e.g., a polypeptide with a known binding specificity or a polynucleotide), so as to allow the presence of the probe/molecule (and therefore its binding target) to be readily detectable. The heterologous nature of the label ensures that it has an origin different from that of the probe or molecule that it labels, such that the probe/molecule attached with the detectable label does not constitute a naturally occurring composition.

The phrase "specifically hybridize(s) to" refers to the binding, duplexing, or hybridization of one polynucleotide sequence to another polynucleotide sequence based on Watson-Crick nucleotide base-pairing under stringent hybridization conditions when that sequences are present in a complex mixture (e.g., total cellular or library DNA or RNA). The phrase "stringent hybridization conditions" refers to conditions under which a nucleic acid (e.g., a polynucleotide probe) will hybridize to its target nucleotide sequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For high stringency hybridization, a positive signal is at least two times background, preferably 10 times background hybridization. Exemplary high stringency hybridization conditions include: 50% formamide, 5×SSC and 1% SDS incubated at 42° C. or 5×SSC and 1% SDS incubated at 65° C., with a wash in 0.2×SSC and 0.1% SDS at 65° C.

The term "immunoassay" describes an assay that uses an antibody to specifically bind an antigen. The immunoassay is characterized by the use of specific binding properties of a particular antibody to identify, isolate, target, and/or detect the presence or quantity of the antigen.

The phrase "specifically binds," when used to describe the binding relationship between an antibody and its target antigen, refers to a binding reaction that is determinative of the presence of the antigen (e.g., a polypeptide) in a heterogeneous population of proteins and other biologics. Thus, under designated immunoassay conditions, the specified antibodies bind to a particular polypeptide at least two times the background and do not substantially bind in a significant amount to other polypeptides or other antigens present in the sample. Specific binding to an antibody under such conditions may require an antibody that is selected for its specificity for a particular protein. For example, polyclonal antibodies raised to a particular antigen can be selected to obtain only those polyclonal antibodies that are specifically immunoreactive with that specific antigen and not with other proteins. This selection may be achieved by subtracting out antibodies that cross-react with molecules. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, *Antibodies, A Laboratory Manual* (1988) for a description of immunoassay formats and conditions that can be used to determine specific immunoreactivity). Typically, a specific binding reaction will yield at least twice of the background signal or noise and more typically more than 10, 20, 50, or up to 100 times the background.

By "host cell" is meant a cell that contains an expression vector and supports the replication or expression of the expression vector. Host cells may be prokaryotic cells such as *E. coli*, or eukaryotic cells such as yeast, insect, amphibian, or mammalian cells such as CHO, HeLa and the like, e.g., cultured cells, explants, and cells in vivo.

A "biological sample," as used herein, is a sample of biological tissue or fluid that potentially contains an IgE antibody produced as a result of fish allergy in a subject. Such samples include, but are not limited to, bodily fluids such as blood (including whole blood or any fraction of blood such as serum or plasma) or urine, small segments isolated from relevant organs or tissues (e.g., skin or mouth swab), and secretion such as sweat or tear taken from an animal (especially a mammal, including human) suspected to have been exposed to fish and have developed fish allergy. Biological samples may also include sections of tissues such as frozen sections taken for histological purposes.

The terms "treat," "treating" and "treatment" refer to the administering of a therapeutically effective amount of an anti-allergy agent or a pharmaceutical composition comprising same, which is effective to ameliorate undesired symptoms associated with fish allergy, to prevent the manifestation of such symptoms before they occur, to slow down the progression of an allergic condition, to slow down the deterioration of symptoms associated with an allergic condition, to slow down the irreversible damage caused by the chronic stage of an allergic condition, to lessen the severity or cure an allergic condition, to improve survival rate or more rapid recovery form such a condition.

The term "administering" or "administration" of a therapeutic agent or composition to a subject includes oral administration, topical contact, administration as a suppository, intravenous, intraperitoneal, intramuscular, intralesional, intrathecal, intranasal, or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, epicutaneous, subcutaneous, intraperitoneal, intraventricular, and intracranial. Other modes of delivery include, but are not limited to, the use of liposomal formulations, intravenous infusion, transdermal patches, etc. One skilled in the art will know of additional methods for administering a therapeutically effective amount of an anti-allergic agent for preventing or relieving one or more symptoms associated with fish allergy. By "co-administer" it is meant that a second therapeutic agent is administered at the same time, just prior to, or just after the administration of a first agent.

The term "physiologically acceptable carrier/excipient" or "pharmaceutically acceptable carrier/excipient" refers to a substance that aids the administration of an active agent to a cell, an organism, or a subject. "Physiologically acceptable excipient" refers to a carrier or excipient that can be included in a therapeutic composition and that causes no significant adverse toxicological effect on the recipient. Non-limiting examples of pharmaceutically acceptable carrier include water, NaCl, normal saline solutions, lactated Ringer's, normal sucrose, normal glucose, binders, fillers, disintegrants, lubricants, coatings, sweeteners, flavors and colors, liposomes, dispersion media, microcapsules, cationic lipid carriers, isotonic and absorption delaying agents, and the like. The excipient may also be substances for providing the formulation with stability, sterility and isotonicity (e.g. antimicrobial preservatives, antioxidants, chelating agents and buffers), for preventing the action of microorganisms (e.g. antimicrobial and antifungal agents, such as parabens, chlorobutanol, phenol, sorbic acid and the like) or for providing the formulation with an edible flavor etc. In some instances, the carrier is an agent that facilitates the delivery of the amino acid molecule to a target cell or tissue. One of skill in the art will recognize that other physiologically acceptable excipient are useful in the present invention.

DETAILED DESCRIPTION OF THE INVENTION

I. Introduction

Provided herein are novel agents that are useful for detecting fish allergy in subjects who are suspected to suffer from fish allergy. β-parvalbumin, β-enolase, and aldolase A of grass carp Ctenopharyngodon idella have been shown in this study as diagnostic markers that can offer better diagnostic sensitivity and specificity in specific IgE tests in comparison to existing tests for indication of allergies to a broad spectrum of fish species. As such, these newly identified C. idella allergens provide an effective first line detection method for making a preliminary determination of whether a person is likely suffering from fish allergy.

The present disclosure provides an isolated polypeptide having at least about 80%, e.g., at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99%, sequence identity to any one of the amino acid sequences set forth in SEQ ID NO: 1, 2, or 3. In some embodiments, the polypeptide comprises an amino acid sequence comprising or consisting of any one of the sequences as set forth in SEQ ID NOs:1, 2, and 3. In other embodiments, the isolated peptide has 100% sequence identity to any one of the amino acid sequences set forth in SEQ ID NOs: 1-3.

II. Production of Newly Identified C. idella Allergens

A. General Recombinant Technology

Basic texts disclosing general methods and techniques in the field of recombinant genetics include Sambrook and Russell, *Molecular Cloning, A Laboratory Manual* (3rd ed. 2001); Kriegler, *Gene Transfer and Expression: A Laboratory Manual* (1990); and Ausubel et al., eds., *Current Protocols in Molecular Biology* (1994).

For nucleic acids, sizes are given in either kilobases (kb) or base pairs (bp). These are estimates derived from agarose or acrylamide gel electrophoresis, from sequenced nucleic acids, or from published DNA sequences. For proteins, sizes are given in kilodaltons (kDa) or amino acid residue numbers. Proteins sizes are estimated from gel electrophoresis, from sequenced proteins, from derived amino acid sequences, or from published protein sequences.

Oligonucleotides that are not commercially available can be chemically synthesized, e.g., according to the solid phase phosphoramidite triester method first described by Beaucage & Caruthers, *Tetrahedron Lett.* 22: 1859-1862 (1981), using an automated synthesizer, as described in Van Devanter et. al., *Nucleic Acids Res.* 12: 6159-6168 (1984). Purification of oligonucleotides is performed using any art-recognized strategy, e.g., native acrylamide gel electrophoresis or anion-exchange HPLC as described in Pearson & Reanier, *J. Chrom.* 255: 137-149 (1983).

The sequence of a polynucleotide encoding a C. idella allergen of this invention (e.g., any one of SEQ ID NOs: 1-3) and related fusion protein can be verified after cloning or subcloning using, e.g., the chain termination method for sequencing double-stranded templates of Wallace et al., *Gene* 16: 21-26 (1981).

B. Cloning and Subcloning of Coding Sequences for C. idella Allergens

Polynucleotide sequences encoding the C. idella allergens of this invention can be determined based on their amino acid sequences (e.g., any one of SEQ ID NOs: 1-3) and available information of the C. idella genome. They can be isolated from an C. idella cDNA or genomic library or can be synthesized by a commercial supplier.

A nucleic acid sequence encoding a C. idella allergen of this invention can be isolated from a C. idella cDNA or genomic DNA library using standard cloning techniques such as polymerase chain reaction (PCR). Most commonly used techniques for this purpose are described in standard texts, e.g., Sambrook and Russell, supra.

cDNA libraries suitable for obtaining a coding sequence for a C. idella allergen of this invention may be commercially available or can be constructed. The general methods of isolating mRNA, making cDNA by reverse transcription, ligating cDNA into a recombinant vector, transfecting into a recombinant host for propagation, screening, and cloning are well known (see, e.g., Gubler and Hoffman, *Gene*, 25: 263-269 (1983); Ausubel et al., supra). Upon obtaining an amplified segment of nucleotide sequence by PCR, the segment can be further used as a probe to isolate a longer length polynucleotide sequence encoding the C. idella allergen from the cDNA library. A general description of appropriate procedures can be found in Sambrook and Russell, supra.

Based on sequence homology, degenerate oligonucleotides can be designed as primer sets and PCR can be performed under suitable conditions (see, e.g., White et al., *PCR Protocols: Current Methods and Applications*, 1993; Griffin and Griffin, *PCR Technology*, CRC Press Inc. 1994) to amplify a segment of nucleotide sequence from a cDNA or genomic library. Using the amplified segment as a probe, a longer length nucleic acid encoding a C. idella allergen of this invention is obtained.

Upon acquiring a nucleic acid sequence encoding a C. idella allergen of this invention, the coding sequence can be modified as appropriate (e.g., adding a coding sequence for a heterologous tag, such as an affinity tag, for example, 6× His tag (SEQ ID NO: 4) or GST tag) and then be subcloned into a vector, for instance, an expression vector, so that a recombinant C. idella allergen can be produced from the resulting construct, for example, after transfection and culturing host cells under conditions permitting recombinant protein expression directed by a promoter operably linked to the coding sequence.

C. Modification of Nucleic Acids for Preferred Codon Usage in a Host Organism

The polynucleotide sequence encoding a C. idella allergen can be further altered to coincide with the preferred codon usage of a particular host. For example, the preferred codon usage of one strain of bacterial cells can be used to derive a polynucleotide that encodes a C. idella allergen of this invention and includes the codons favored by this strain. The frequency of preferred codon usage exhibited by a host cell can be calculated by averaging frequency of preferred codon usage in a large number of genes expressed by the host cell (e.g., calculation service is available from web site of the Kazusa DNA Research Institute, Japan). This analysis is preferably limited to genes that are highly expressed by the host cell.

At the completion of modification, the coding sequences are verified by sequencing and are then subcloned into an appropriate expression vector for recombinant production of the *C. idella* allergens of this invention.

D. Chemical Synthesis of the *C. idella* Allergens

The amino acid sequences of the *C. idella* allergens of this invention are provided in SEQ ID NOs: 1-3. These allergens in some cases may be presented in the form of fusion proteins containing at least one, perhaps two (e.g., one on each of the N-terminus and C-terminus) peptides from a heterologous origin, such as affinity tag for the ease of detection and/or isolation of the antigens. Aside from recombinant production, these polypeptides can also be synthesized chemically using conventional peptide synthesis or other protocols well known in the art.

Polypeptides may be synthesized by solid-phase peptide synthesis methods using procedures similar to those described by Merrifield et al., *J. Am. Chem. Soc.*, 85:2149-2156 (1963); Barany and Merrifield, *Solid-Phase Peptide Synthesis, in The Peptides: Analysis, Synthesis, Biology* Gross and Meienhofer (eds.), Academic Press, N.Y., vol. 2, pp. 3-284 (1980); and Stewart et al., *Solid Phase Peptide Synthesis* 2nd ed., Pierce Chem. Co., Rockford, Ill. (1984). During synthesis, N-α-protected amino acids having protected side chains are added stepwise to a growing polypeptide chain linked by its C-terminal and to a solid support, i.e., polystyrene beads. The peptides are synthesized by linking an amino group of an N-α-deprotected amino acid to an α-carboxy group of an N-α-protected amino acid that has been activated by reacting it with a reagent such as dicyclohexylcarbodiimide. The attachment of a free amino group to the activated carboxyl leads to peptide bond formation. The most commonly used N-α-protecting groups include Boc, which is acid labile, and Fmoc, which is base labile.

Materials suitable for use as the solid support are well known to those of skill in the art and include, but are not limited to, the following: halomethyl resins, such as chloromethyl resin or bromomethyl resin; hydroxymethyl resins; phenol resins, such as 4-(α-[2,4-dimethoxyphenyl]-Fmoc-aminomethyl)phenoxy resin; tert-alkyloxycarbonyl-hydrazidated resins, and the like. Such resins are commercially available, and their methods of preparation are known by those of ordinary skill in the art.

Briefly, the C-terminal N-α-protected amino acid is first attached to the solid support. The N-α-protecting group is then removed. The deprotected α-amino group is coupled to the activated α-carboxylate group of the next N-α-protected amino acid. The process is repeated until the desired peptide is synthesized. The resulting peptides are then cleaved from the insoluble polymer support and the amino acid side chains deprotected. Longer peptides can be derived by condensation of protected peptide fragments. Details of appropriate chemistries, resins, protecting groups, protected amino acids and reagents are well known in the art and so are not discussed in detail herein (See, Atherton et al., *Solid Phase Peptide Synthesis: A Practical Approach*, IRL Press (1989), and Bodanszky, *Peptide Chemistry, A Practical Textbook*, 2nd Ed., Springer-Verlag (1993)).

III. Expression and Purification of *C. idella* Allergens

Following verification of the coding sequence, the *C. idella* allergens or fusion proteins of the present invention can be produced using routine techniques in the field of recombinant genetics, relying on the polynucleotide sequences encoding the polypeptides disclosed herein.

A. Expression Systems

To obtain high level expression of a nucleic acid encoding a *C. idella* allergen or fusion polypeptide of the present invention, one typically subclones a polynucleotide encoding the polypeptide into an expression vector that contains a strong promoter (typically heterologous, i.e., of non-*C. idella* origin) to direct transcription, a transcription/translation terminator and a ribosome binding site for translational initiation. Suitable bacterial promoters are well known in the art and described, e.g., in Sambrook and Russell, supra, and Ausubel et al., supra. Bacterial expression systems for expressing a recombinant polypeptide are available in, e.g., *E. coli*, *Bacillus* sp., *Salmonella*, and *Caulobacter*. Kits for such expression systems are commercially available. Eukaryotic expression systems for mammalian cells, yeast, and insect cells are well known in the art and are also commercially available. In one embodiment, the eukaryotic expression vector is an adenoviral vector, an adeno-associated vector, or a retroviral vector.

The promoter used to direct expression of a heterologous nucleic acid depends on the particular application. The promoter is optionally positioned about the same distance from the heterologous transcription start site as it is from the transcription start site in its natural setting. As is known in the art, however, some variation in this distance can be accommodated without loss of promoter function.

In addition to the promoter, the expression vector typically includes a transcription unit or expression cassette that contains all the additional elements required for the expression of the *C. idella* allergen or fusion polypeptide in host cells. A typical expression cassette thus contains a promoter operably linked to the coding sequence and signals required for efficient polyadenylation of the transcript, ribosome binding sites, and translation termination. The nucleic acid sequence encoding the *C. idella* allergen or fusion polypeptide is typically linked to a cleavable signal peptide sequence to promote secretion of the recombinant polypeptide by the transformed cell. Such signal peptides include, among others, the signal peptides from tissue plasminogen activator, insulin, and neuron growth factor, and juvenile hormone esterase of *Heliothis virescens*. Additional elements of the cassette may include enhancers and, if genomic DNA is used as the structural gene, introns with functional splice donor and acceptor sites.

In addition to a promoter sequence, the expression cassette should also contain a transcription termination region downstream of the structural gene to provide for efficient termination. The termination region may be obtained from the same gene as the promoter sequence or may be obtained from different genes.

The particular expression vector used to transport the genetic information into the cell is not particularly critical. Any of the conventional vectors used for expression in eukaryotic or prokaryotic cells may be used. Standard bacterial expression vectors include plasmids such as pBR322 based plasmids, pSKF, pET23D, and fusion expression systems such as GST and LacZ. Epitope tags can also be added to recombinant proteins to provide convenient methods of isolation, e.g., c-myc.

Expression vectors containing regulatory elements from eukaryotic viruses are typically used in eukaryotic expression vectors, e.g., SV40 vectors, papilloma virus vectors, and vectors derived from Epstein-Barr virus. Other exemplary eukaryotic vectors include pMSG, pAV009/A$^+$, pMTO10/A$^+$, pMAMneo-5, baculovirus pDSVE, and any other vector allowing expression of proteins under the direction of the SV40 early promoter, SV40 later promoter, metallothionein promoter, murine mammary tumor virus promoter, Rous sarcoma virus promoter, polyhedrin promoter, or other promoters shown effective for expression in eukaryotic cells.

Some expression systems have markers that provide gene amplification such as thymidine kinase, hygromycin B phosphotransferase, and dihydrofolate reductase. Alternatively, high yield expression systems not involving gene amplification are also suitable, such as a baculovirus vector in insect cells, with a polynucleotide sequence encoding the *C. idella* allergen or fusion polypeptide under the direction of the polyhedrin promoter or other strong baculovirus promoters.

The elements that are typically included in expression vectors also include a replicon that functions in *E. coli*, a gene encoding antibiotic resistance to permit selection of bacteria that harbor recombinant plasmids, and unique restriction sites in nonessential regions of the plasmid to allow insertion of eukaryotic sequences. The particular antibiotic resistance gene chosen is not critical, any of the many resistance genes known in the art are suitable. The prokaryotic sequences are optionally chosen such that they do not interfere with the replication of the DNA in eukaryotic cells, if necessary. Similar to antibiotic resistance selection markers, metabolic selection markers based on known metabolic pathways may also be used as a means for selecting transformed host cells.

When periplasmic expression of a recombinant protein (e.g., a *C. idella* allergen or fusion polypeptide of the present invention) is desired, the expression vector further comprises a sequence encoding a secretion signal, such as the *E. coli* OppA (Periplasmic Oligopeptide Binding Protein) secretion signal or a modified version thereof, which is directly connected to 5' of the coding sequence of the protein to be expressed. This signal sequence directs the recombinant protein produced in cytoplasm through the cell membrane into the periplasmic space. The expression vector may further comprise a coding sequence for signal peptidase 1, which is capable of enzymatically cleaving the signal sequence when the recombinant protein is entering the periplasmic space. More detailed description for periplasmic production of a recombinant protein can be found in, e.g., Gray et al., *Gene* 39: 247-254 (1985), U.S. Pat. Nos. 6,160,089 and 6,436,674.

B. Transfection Methods

Standard transfection methods are used to produce bacterial, mammalian, yeast, insect, or plant cell lines that express large quantities of a recombinant polypeptide, which are then purified using standard techniques (see, e.g., Colley et al., *J. Biol. Chem.* 264: 17619-17622 (1989); *Guide to Protein Purification*, in *Methods in Enzymology*, vol. 182 (Deutscher, ed., 1990)). Transformation of eukaryotic and prokaryotic cells are performed according to standard techniques (see, e.g., Morrison, *J. Bact.* 132: 349-351 (1977); Clark-Curtiss & Curtiss, *Methods in Enzymology* 101: 347-362 (Wu et al., eds, 1983).

Any of the well-known procedures for introducing foreign nucleotide sequences into host cells may be used. These include the use of calcium phosphate transfection, polybrene, protoplast fusion, electroporation, liposomes, microinjection, plasma vectors, viral vectors and any of the other well-known methods for introducing cloned genomic DNA, cDNA, synthetic DNA, or other foreign genetic material into a host cell (see, e.g., Sambrook and Russell, supra). It is only necessary that the particular genetic engineering procedure used be capable of successfully introducing at least one gene into the host cell capable of expressing the recombinant polypeptide.

C. Detection of Recombinant Expression of *C. idella* Allergen in Host Cells

After the expression vector is introduced into appropriate host cells, the transfected cells are cultured under conditions favoring expression of the *C. idella* allergen or fusion polypeptide. The cells are then screened for the expression of the recombinant polypeptide, which is subsequently recovered from the culture using standard techniques (see, e.g., Scopes, *Protein Purification: Principles and Practice* (1982); U.S. Pat. No. 4,673,641; Ausubel et al., supra; and Sambrook and Russell, supra).

Several general methods for screening gene expression are well known among those skilled in the art. First, gene expression can be detected at the nucleic acid level. A variety of methods of specific DNA and RNA measurement using nucleic acid hybridization techniques are commonly used (e.g., Sambrook and Russell, supra). Some methods involve an electrophoretic separation (e.g., Southern blot for detecting DNA and Northern blot for detecting RNA), but detection of DNA or RNA can be carried out without electrophoresis as well (such as by dot blot). The presence of nucleic acid encoding a *C. idella* allergen or fusion polypeptide in transfected cells can also be detected by PCR or RT-PCR using sequence-specific primers.

Second, gene expression can be detected at the polypeptide level. Various immunological assays are routinely used by those skilled in the art to measure the level of a gene product, particularly using polyclonal or monoclonal antibodies that react specifically with a *C. idella* allergen of this invention (e.g., Harlow and Lane, *Antibodies, A Laboratory Manual*, Chapter 14, Cold Spring Harbor, 1988; Kohler and Milstein, *Nature,* 256: 495-497 (1975)). Such techniques require antibody preparation by selecting antibodies with high specificity against the *C. idella* allergen. The methods of raising polyclonal and monoclonal antibodies are well established and their descriptions can be found in the literature, see, e.g., Harlow and Lane, supra; Kohler and Milstein, *Eur. J. Immunol.,* 6: 511-519 (1976). More detailed descriptions of preparing antibodies against the *C. idella* allergens of this invention and conducting immunological assays detecting the polypeptides containing the antigens are provided in a later section.

D. Purification of Recombinantly Produced *C. idella* Allergens

Once the expression of a recombinant *C. idella* allergen of this invention or fusion polypeptide in transfected host cells is confirmed, the host cells are then cultured in an appropriate scale for the purpose of purifying the recombinant polypeptide.

1. Purification of Recombinantly Produced Polypeptide from Bacteria

When the *C. idella* allergens or fusion polypeptides of the present invention are produced recombinantly by transformed bacteria in large amounts, typically after promoter induction, although expression can be constitutive, the polypeptides may form insoluble aggregates. There are several protocols that are suitable for purification of protein inclusion bodies. For example, purification of aggregate proteins (hereinafter referred to as inclusion bodies) typically involves the extraction, separation and/or purification of inclusion bodies by disruption of bacterial cells, e.g., by incubation in a buffer of about 100-150 μg/ml lysozyme and 0.1% Nonidet P40, a non-ionic detergent. The cell suspension can be ground using a Polytron grinder (Brinkman Instruments, Westbury, N.Y.). Alternatively, the cells can be sonicated on ice. Alternate methods of lysing bacteria are described in Ausubel et al. and Sambrook and Russell, both supra, and will be apparent to those of skill in the art.

The cell suspension is generally centrifuged and the pellet containing the inclusion bodies resuspended in buffer which does not dissolve but washes the inclusion bodies, e.g., 20 mM Tris-HCl (pH 7.2), 1 mM EDTA, 150 mM NaCl and 2% Triton-X 100, a non-ionic detergent. It may be necessary to repeat the wash step to remove as much cellular debris as possible. The remaining pellet of inclusion bodies may be resuspended in an appropriate buffer (e.g., 20 mM sodium phosphate, pH 6.8, 150 mM NaCl). Other appropriate buffers will be apparent to those of skill in the art.

Following the washing step, the inclusion bodies are solubilized by the addition of a solvent that is both a strong hydrogen acceptor and a strong hydrogen donor (or a combination of solvents each having one of these properties). The proteins that formed the inclusion bodies may then be renatured by dilution or dialysis with a compatible buffer. Suitable solvents include, but are not limited to, urea (from about 4 M to about 8 M), formamide (at least about 80/%, volume/volume basis), and guanidine hydrochloride (from about 4 M to about 8 M). Some solvents that are capable of solubilizing aggregate-forming proteins, such as SDS (sodium dodecyl sulfate) and 70% formic acid, may be inappropriate for use in this procedure due to the possibility of irreversible denaturation of the proteins, accompanied by a lack of immunogenicity and/or activity. Although guanidine hydrochloride and similar agents are denaturants, this denaturation is not irreversible and renaturation may occur upon removal (by dialysis, for example) or dilution of the denaturant, allowing re-formation of the immunologically and/or biologically active protein of interest. After solubilization, the protein can be separated from other bacterial proteins by standard separation techniques. For further description of purifying recombinant polypeptides from bacterial inclusion body, see, e.g., Patra et al., *Protein Expression and Purification* 18: 182-190 (2000).

Alternatively, it is possible to purify recombinant polypeptides, e.g., a *C. idella* allergen of this invention or fusion polypeptide thereof, from bacterial periplasm. Where the recombinant protein is exported into the periplasm of the bacteria, the periplasmic fraction of the bacteria can be isolated by cold osmotic shock in addition to other methods known to those of skill in the art (see e.g., Ausubel et al., supra). To isolate recombinant proteins from the periplasm, the bacterial cells are centrifuged to form a pellet. The pellet is resuspended in a buffer containing 20% sucrose. To lyse the cells, the bacteria are centrifuged and the pellet is resuspended in ice-cold 5 mM $MgSO_4$ and kept in an ice bath for approximately 10 minutes. The cell suspension is centrifuged and the supernatant decanted and saved. The recombinant proteins present in the supernatant can be separated from the host proteins by standard separation techniques well known to those of skill in the art.

2. Standard Protein Separation Techniques for Purification

When a recombinant polypeptide, e.g., a *C. idella* allergen or fusion polypeptide of the present invention, is expressed in host cells in a soluble form, its purification can follow the standard protein purification procedure described below. This standard purification procedure is also suitable for purifying a *C. idella* allergen or fusion polypeptide obtained from chemical synthesis.

i. Solubility Fractionation

Often as an initial step, and if the protein mixture is complex, an initial salt fractionation can separate many of the unwanted host cell proteins (or proteins derived from the cell culture media) from the recombinant protein of interest. The preferred salt is ammonium sulfate. Ammonium sulfate precipitates proteins by effectively reducing the amount of water in the protein mixture. Proteins then precipitate on the basis of their solubility. The more hydrophobic a protein is, the more likely it is to precipitate at lower ammonium sulfate concentrations. A typical protocol is to add saturated ammonium sulfate to a protein solution so that the resultant ammonium sulfate concentration is between 20-30%. This will precipitate the most hydrophobic proteins. The precipitate is discarded (unless the protein of interest is hydrophobic) and ammonium sulfate is added to the supernatant to a concentration known to precipitate the protein of interest. The precipitate is then solubilized in buffer and the excess salt removed if necessary, through either dialysis or diafiltration. Other methods that rely on solubility of proteins, such as cold ethanol precipitation, are well known to those of skill in the art and can be used to fractionate complex protein mixtures.

ii. Size Differential Filtration

Based on a calculated molecular weight, a protein of greater and lesser size can be isolated using ultrafiltration through membranes of different pore sizes (for example, Amicon or Millipore membranes). As a first step, the protein mixture is ultrafiltered through a membrane with a pore size that has a lower molecular weight cut-off than the molecular weight of a protein of interest, e.g., a *C. idella* allergen of this invention or a fusion polypeptide thereof. The retentate of the ultrafiltration is then ultrafiltered against a membrane with a molecular cut off greater than the molecular weight of the protein of interest. The recombinant protein will pass through the membrane into the filtrate. The filtrate can then be chromatographed as described below.

iii. Column Chromatography

The proteins of interest (such as a *C. idella* allergen or fusion polypeptide of the present invention) can also be separated from other proteins on the basis of their size, net surface charge, hydrophobicity, or affinity for ligands. In addition, antibodies raised against a *C. idella* allergen can be conjugated to column matrices and the *C. idella* allergen immunopurified. All of these methods are well known in the art.

It will be apparent to one of skill that chromatographic techniques can be performed at any scale and using equipment from many different manufacturers (e.g., Pharmacia Biotech).

IV. Immunoassays for Detection of *C. idella* Antibodies

One aspect of this invention provides immunoassays used in the detection of antibodies, especially IgE antibodies, that are specifically reactive with the *C. idella* allergens identified in this application for the purpose of detecting a possible case of fish allergy in a patient who may have been exposed to fish and may be actively suffering from a fish allergy. The newly identified *C. idella* allergens described herein are useful for carrying out these immunological assays.

A. Patients to be Testes

Patients to be tested by the fish allergy diagnostic method of this invention include those who have recently consumed fish or fish-containing food items or may have come into contact with fish, fish-containing substance, or fish by-products and exhibiting possible signs of an allergy, including but not limited to hives or a skin rash, nausea, stomach cramps, indigestion, vomiting and/or diarrhea; stuffy or runny nose and/or sneezing; headaches; asthma; and anaphylaxis.

A sample is taken from a patient being tested for likely fish allergy, for example, a blood sample may be collected and processed (e.g., to yield a plasma or serum sample) in preparation for the specific IgE assay.

B. Immunoassays for Detecting IgE Antibodies

Once a *C. idella* allergen or fusion polypeptide of the present invention is available, the amount of the specific IgE in a sample, e.g., a blood/serum/plasma sample, or a skin sample or mouth swab, can be measured by a variety of immunoassay methods providing qualitative and quantitative results to a skilled artisan. For a review of immunological and immunoassay procedures in general see, e.g., Stites, supra; U.S. Pat. Nos. 4,366,241; 4,376,110; 4,517,288; and 4,837,168.

1. Labeling in Immunoassays

Immunoassays often utilize a labeling agent to specifically bind to and label the binding complex formed by the antibody and the target protein (antigen). The labeling agent may itself be one of the moieties comprising the antibody/target protein complex, or may be a third moiety, such as another antibody, that specifically binds to the antibody/target protein complex. A label may be detectable by spectroscopic, photochemical, biochemical, immunochemical, electrical, optical or chemical means. Examples include, but are not limited to, magnetic beads (e.g., Dynabeads™), fluorescent dyes (e.g., fluorescein isothiocyanate, Texas red, rhodamine, and the like), radiolabels (e.g., $^3$H, $^{125}$I, $^{35}$S, $^{14}$C, or $^{32}$P), enzymes (e.g., horse radish peroxidase, alkaline phosphatase, and others commonly used in an ELISA), and colorimetric labels such as colloidal gold or colored glass or plastic (e.g., polystyrene, polypropylene, latex, etc.) beads.

In some cases, the labeling agent is a second antibody (e.g., an anti-IgE antibody) bearing a detectable label. Alternatively, the second antibody may lack a label, but it may, in turn, be bound by a labeled third antibody specific to antibodies of the species from which the second antibody is derived. The second antibody can be modified with a detectable moiety, such as biotin, to which a third labeled molecule can specifically bind, such as enzyme-labeled streptavidin.

Other proteins capable of specifically binding immunoglobulin constant regions, such as protein A or protein G, can also be used as the label agents. These proteins are normal constituents of the cell walls of streptococcal bacteria. They exhibit a strong non-immunogenic reactivity with immunoglobulin constant regions from a variety of species (see, generally, Kronval, et al. *J. Immunol.*, 111: 1401-1406 (1973); and Akerstrom, et al., *J. Immunol.*, 135: 2589-2542 (1985)).

2. Immunoassay Format

Immunoassays for detecting a specific IgE of interest (e.g., an IgE specifically immune-reactive against a *C. idella* allergen of any one of SEQ ID NOs: 1-3) from samples may be either competitive or noncompetitive. A typical specific IgE immunoassay is a noncompetitive immunoassay in which the amount of captured target IgE is directly measured. In one preferred "sandwich" assay, for example, one or more of the *C. idella* allergens of the present invention can be bound or immobilized directly to a solid substrate (such as the surface of a plate). The immobilized allergen(s) can then capture the specific IgE in test samples. The antibody/target protein complex thus immobilized is then bound by a labeling agent, such as a second or third antibody bearing a label, as described above.

Other assay formats include liposome immunoassays (LIA), which use liposomes designed to bind specific molecules (e.g., antibodies) and release encapsulated reagents or markers. The released chemicals are then detected according to standard techniques (see, Monroe et al., *Amer. Clin. Prod. Rev.*, 5: 34-41 (1986)).

In practicing the method of the present invention for detecting fish allergy in a patient, an allergen array may be used for performing an immunoassay. For example, a plurality of the *C. idella* allergens or fusion proteins of the present invention (e.g., 2 or 3 selected from SEQ ID NOs: 1-3) or fusion polypeptides each comprising one of the allergens are immobilized to a solid substrate at a predetermined location to form an array, which then may be used in an immunoassay for detecting in a sample taken from a patient suspected of suffering from a fish allergy. Typically, positive results with multiple allergens, e.g., at least 1 out 2 or 2 out of 3 of all allergens on the array, indicate the patient as likely suffering from a case of fish allergy.

For these immunoassays, the patient being tested may be one who may have been exposed to fish or fish-contaminated substance and may have begun to demonstrate symptoms of an active fish allergy. Once a determination of likely fish allergy is made, the patient may be given treatment for his allergy in accordance with a physician's direction, such as administration of antihistamines or corticosteroids or immunotherapy (e.g., sublingual immunotherapy).

V. KITS

The invention also provides kits for diagnosis of a fish allergy in a subject according to the method of the present invention. The kits typically include a first container that contains a composition including a polypeptide comprising or consisting of an amino acid sequence selected from SEQ ID NOs: 1-3, and a second container containing a negative control sample that is taken, optionally processed, from a patient who has been confirmed to have no fish allergies. Optionally, the kit may include a positive control sample, which is taken (optionally processed) from a subject who has been confirmed to be allergic to fish and therefore has a detectable level of specific IgE in his body. The polypeptide may be one of a plurality of polypeptides, each comprising or consisting of a different amino acid sequence selected from SEQ ID NOs: 1-3. The polypeptide(s) maybe immobilized to a solid substrate, in some cases in the form of an array, and the solid substrate such as an assay plate is suitable for use in an immunoassay such as ELISA.

The kit may further include another container containing a secondary antibody, for example, an anti-IgE antibody, which is optionally conjugated to a detectable label. In addition, the kit may be include informational material containing instructions for a user on how to use the kit for performing an assay and determining whether a test subject is likely to suffer from a case of fish allergy.

EXAMPLES

The following examples are provided by way of illustration only and not by way of limitation. Those of skill in the art will readily recognize a variety of non-critical parameters that could be changed or modified to yield essentially the same or similar results.

Example 1. Identification of New Allergens in *Ctenopharyngodon idella* and their Use for Diagnosis of Fish Allergy Introduction Food allergy involving the potentially fatal adverse immune response to foods affected 5% of adults and 8% of children among the general population[1]. The increasing prevalence of food allergies imposes significant socio-economic burden to the society[2] and exert dramatic effect on the quality of life of patients[3,4]. Avoiding the causative food remains the primary management strategy for food allergy, but this might lead to growth and nutritional concern in children allergic to multiple food items[5]. Several studies reported unnecessary food avoidance due to misdiagnosis of food allergy[6-8], suggesting a need to improve the accuracy of current diagnostic tests. Skin prick test (SPT) and specific IgE (sIgE) assay are two conventional diagnostic approaches in clinical practice, but a recent meta-analysis revealed poor diagnostic performance of these tests[9]. On the other hand, double-blind placebo-controlled food challenges, despite being the gold standard of food allergy diagnosis, are time-consuming, labor-intensive and sometimes risky[10].

Diagnosis of fish allergy is more complex than diagnosis of other types of food allergies, due to the presence of huge variety of marketable fishes and extensive cross-reactivity of the major allergen parvalbumin among different fish species[11]. Although allergen extracts from 27 fish species are available for sIgE measurement by the Phadia ImmunoCAP system, most studies only used a few species (e.g., cod, salmon, tuna) as surrogate markers for the diagnosis of fish allergy. However, parvalbumin content and allergenicity varied significantly among fishes[12,13], such that the allergy test results of one fish cannot be generalized and extrapolated to all kinds of fishes. In light of this, component-resolved diagnosis (CRD) emerges as an attractive approach for fish allergy diagnosis. CRD aims to detect IgE reactivity to clinically relevant allergen components, thereby minimizing false positive results in extract-based tests where sensitization is directed to hypoallergenic or non-allergenic components. It can also improve sensitivity by targeting allergen components that are under-represented in allergen extracts and overcoming the problem of varying allergen contents in whole extracts[14]. Taken together, the component-resolved approach can be a robust supplementary or even a replacement tool to conventional extract-based allergy tests and reduce the need for oral food challenge[15].

The development of CRD largely depends on the availability of allergen components. Previous studies have shown that subjects from different geographical regions could have a distinct IgE sensitization profile to very closely related food allergen[16,17]. At present, only Gad c 1 from the Baltic cod has been evaluated for its diagnostic utility but its diagnostic value is in doubt especially for populations that consume very little cod or cod-related species[18]. It is thus most advantageous to use fish species most relevant to local consumption pattern, but the molecular information of the allergens might not always be available given the huge variety of marketable fishes. Nevertheless, identification and cloning of unknown allergens using conventional methods (e.g., cDNA library) are often tedious and time-consuming, resulting in a lack of diagnostic marker for fish allergy apart from Gad c 1. Described herein is an in silico approach to derive protein sequences of fish allergen components from the Transcriptome Shotgun Assembly (TSA), using grass carp *Ctenopharyngodon idella* as an example, for the development of fish CRD. This approach bypasses cDNA library screening and makes use of the huge amount of transcriptomic data deposited at the Genbank to obtain allergen sequences for subsequent recombinant allergen preparation. Grass carp is the top cultured and consumed freshwater species in China[19], yet allergens of this species have not been characterized and their amino acid sequences are not available. Most importantly, grass carp is often the first fish to be introduced into an infant's diet and is one of the commonest culprit species leading to fish-allergic reactions in Hong Kong. In this study the present inventors cloned the allergen components parvalbumin, aldolase, and enolase using sequences obtained from TSA database of grass carp, and compared the diagnostic value between sIgE to grass carp allergens and conventional extract-based ImmunoCAP tests for fish allergy in Hong Kong children.

Methods

Recruitment Offish-Allergic Subjects

Sixty-two fish-allergic patients aged 1-20 years old were recruited from allergy clinics of three regional hospitals in Hong Kong. All subjects were confirmed by pediatricians to exhibit a clear history of immediate allergic reactions within two hours of fish consumption or contact on at least two exposures to the same fish. Details of the allergic reactions and the causative or tolerant fish species of each patient were documented. Fish sensitization was detected by SPT with white fish mix or salmon extracts (ALK-Abéllo) and/or sIgE to cod, tuna, salmon and recombinant cod parvalbumin rGadc 1. Ten subjects regularly tolerated fish were recruited as controls. SPT with wheal≥3 mm larger than normal saline control and fish-specific IgE≥0.35 $kU_A/L$ by ImmunoCAP (Phadia), were considered positive. This study was approved by institutional review boards of all hospitals, and subjects and/or their parents gave informed written consent to particiate.

Alignment Offish Allergens Using TSA Database

The amino acid sequences of Gad m 1 (UniProtKB: Q90YK9.3), Sal s 2 (UniProtKB: B5DGQ7) and Sal s 3 (UniProtKB: B5DGM7) were used as the template sequence to search for parvalbumin-, enolase- and aldolase-like sequences in grass carp respectively. The tblastn in the BLAST suite was used to search for translated nucleotide sequence in the TSA of *C. idella* using the BLOSUM 62 matrix and expected threshold of 10. Transcripts from the database with query cover>95% and sequence identity>60% were considered possible candidates for further validation. These sequences were then subjected to BLAST search against a nucleotide collection database to exclude non-allergenic isoforms.

Preparation of Recombinant Fish Allergens

Gene sequences encoding for beta-parvalbumin, beta-enolase and aldolase A of *C. idella*, and cod allergen Gad m 1 (UniprotKB: Q90YK9.3) were synthesized (Genscript) and subcloned into pET30a expression vector (Novagen) using the NcoI and XhoI restriction sites. The plasmids were then transformed into BL21-DE3 competent *E. coli* cells (New England Biolabs) for propagation. The transformed *E. coli* cells were cultured in MagicMedia *E. coli* expression medium (Thermo Fisher) according to manufacturer's instructions. The polyhistidine-tagged recombinant allergens were purified using the HisPur cobalt purification kit and the protein concentration was measured with the BCA protein assay kit (Pierce). The enzymatic activities of recombinant enolase and aldolase were measured by colorimetric assay kits for enolase and aldolase activities (BioVision) respectively.

SDS-PAGE and Western Blotting

Purified recombinant allergens were resolved on a 12% polyacrylamide gel under denaturing conditions. The allergens were then transferred to an Immun-Blot PVDF membrane (Bio-Rad) with Trans-Blot SD semi-dry electrophoretic transfer cell (Bio-Rad). The membranes were then blocked with 5% non-fat dry milk (Bio-Rad) in phosphate-buffered saline (PBS). After washing three times with PBST, the membranes were incubated overnight at 4° C. with either anti-parvalbumin (Sigma), anti-enolase (Lifespan BioSciences) or anti-aldolase (Aviva Systems Biology) antibodies diluted in 5% blocking solution. The membranes were then washed with PBST for three times and incubated with HRP-conjugated anti-mouse IgG, anti-goat IgG or anti-rabbit IgG secondary antibodies at room temperature for 1 h. The membranes were washed with PBST for five times before incubating with Supersignal West Pico Plus (Thermo Fisher) chemiluminescent substrate, with the signal being detected by a ChemiDoc XRS+ Image system after 5 min of incubation (Bio-Rad).

Enzyme-Linked Immunosorbant Assay (FLSA)

Recombinant allergens (5 μg/ml NaHCO$_3$, pH 9.6 coating buffer, 100 μl per well) were coated onto Maxisorp microtiter plates (Nunc) and incubated at 37° C. for 3 h. The plates were washed with 0.05% Tween 20/PBS (PBST) and blocked with 10% fetal bovine serum (FBS) (Gibco) diluted in PBS at room temperature for 2 h. Serum samples were diluted with blocking buffer at 1:10 and incubated at 4° C. overnight. The plates were then washed with PBST and incubated with biotinylated anti-human IgE antibodies at 1:1000 dilution (Southern Biotech) at room temperature for 1 h. After washing with PBST, the plates were incubated with HRP avidin D at 1:1000 dilution (Vector) at room temperature for 30 min, washed with PBST for five times and incubated with 100 μl/well of 1-step Ultra TMB-ELISA Substrate Solution (Thermo Fisher) for color development. The reaction was terminated by adding 0.1 M sulfuric acid to the wells after 30 min and the optical density (O.D.) at 450 nm was measured using a microplate reader. Results were considered positive only if the O.D. is two-fold higher than those of negative controls. The O.D. readout was converted into the arbitrary kU$_A$/L unit by running the ELISA in parallel with a serum sample with known sIgE to rCyp c 1 by ImmunoCAP. The reference sample was added to ELISA plates coated with rCyp c 1 (Biomay) in serial dilutions to generate a standard curve for unit conversion. For cross-inhibition ELISA, the inhibitor (1 μg/ml, 20 μg/ml or 50 μg/ml) was co-incubated with pooled serum samples at room temperature for 2 h before adding to ELISA plates.

Statistical Analysis

Statistical analyses were performed by GraphPad Prism version 6. Tukey's multiple comparison test and Mann-Whitney test were used to compare paired and unpaired data respectively. The McNemar's chi-square test was used to compare sensitivity of two diagnostic tests. P-values<0.05 were considered statistically significant.

Results

Patient Characteristics

Fifty-three of 62 subjects reported history of allergic reactions to seawater fishes while 45 had allergic reactions after consumption of freshwater fishes. Thirty-six subjects were allergic to both seawater and freshwater fishes. At the time of recruitment, 28 subjects (45.2%) were tolerant to at least one seawater fish but only four subjects (6.4%) reported tolerance to any freshwater species. Based on the NIAID/FAAN criteria for anaphylaxis, 20 patients (32.2%) had history of anaphylaxis with the majority presenting with respiratory compromise and/or recurrent vomiting. Up to two-third of subjects experienced angioedema and facial rash, which were the commonest features associated with fish allergy while abdominal pain was only observed in two of the subjects. The characteristics of the study subjects are summarized in Tables 4 and 5.

Identification of Allergen Transcripts

Using Gad m 1 amino acid sequence as a template, four transcripts c692324, c8509, c185084 and c29630 were identified from TSA of *C. idella* (Table 2). Using BLAST search against a nucleotide collection database, c692324 was identified as alpha-parvalbumin while c8509 and c185084 were identified as thymic-like parvalbumin. Only transcript c29630 was identified as beta-parvalbumin, which was the known allergenic isoform in fish. Using Sal s 2 amino acid sequence as a template, three transcripts c70816, c52484, c60301 were identified from TSA of *C. idella* (Table 2). Using BLAST search against a nucleotide collection database, c60301 was identified as the alpha-enolase. Transcripts c70816 and c52484 have the same amino acid sequence and identified as beta-enolase, which was the known allergenic isoform in fish. Using Sal s 3 amino acid sequence as a template, four transcripts c23832, c72290, c95581 and c39713 were identified from TSA of *C. idella* (Table 1). Using BLAST search against a nucleotide collection database, transcripts c95581 and c39713 have the same amino acid sequence and identified as aldolase C. Transcripts c23832 and c72290 have the same amino acid sequence and identified as aldolase A, which was the known allergenic isoform in fish.

Purification and Biochemical Characterization of Recombinant Fish Allergens

Recombinant allergens from *C. idella* were purified to homogeneity and resolved on a polyacrylamide gel. Parvalbumin, enolase and aldolase had molecular weights of 12 kDa, 40 kDa and 50 kDa, respectively (FIG. 1a), which were concurrent with their predicted molecular weights. The identity of purified recombinant allergens was confirmed by immunoblotting with anti-parvalbumin, anti-enolase or anti-aldolase antibody, which detected purified proteins at corresponding molecular weights (FIG. 1b). Both recombinant enolase and aldolase demonstrated enzymatic activity, suggesting the conservation of their native conformation.

Diagnostic Sensitivity of SPT and ImmunoCAP

For SPT, 72.9% of subjects (35/48) were positive to white fish mix while 58.7% of subjects (27/46) were positive to salmon. The sIgE levels varied among fishes, where 64.5%, 51.6% and 59.7% of all subjects had positive sIgE testing for cod, tuna and salmon extracts respectively (FIG. 2). Alternatively, 79.0% of all subjects had positive sIgE to the recombinant cod parvalbumin rGad c 1. Notably, the sensitivity of the three fish extracts was slightly higher in seawater fish-allergic subjects (52.8-67.9%) than freshwater fish-allergic subjects (51.1-60.0%). Consistent results were observed in only 68.8% (33/48) of subjects between white fish mix (by SPT) and cod (by sIgE) and in 65.2% between SPT and sIgE of salmon. None of the control subjects showed positive results to SPT and sIgE.

Diagnostic Sensitivity of Recombinant Grass Carp Components

IgE reactivity to recombinant parvalbumin, enolase and aldolase from grass carp C.

*Idella* was tested by IgE ELISA, and the optical density measured was converted to the arbitrary unit (kU$_A$/L). Fifty-seven subjects (91.9%) had sIgE level≥0.35 kU$_A$/L to grass carp parvalbumin, while only 15 (24.1%) and 18 (29.0%) subjects had positive sIgE to grass carp enolase and aldolase respectively (FIG. 2). Notably, grass carp parvalbumin was equally sensitive to identify subjects who were allergic to seawater (92.5%) or freshwater (95.6%) fishes. Only two subjects were non-reactive to parvalbumin but positive to enolase or aldolase. All subjects with sIgE<0.35 kU$_A$/L to grass carp parvalbumin were also sIgE-negative against the three fish extracts and rGad c 1.

Comparison of Diagnostic Sensitivity Between Grass Carp Parvalbumin and ImmunoCAP IgE reactivity of grass carp parvalbumin in the subjects was significantly higher than rGad c 1 or any of the cod, tuna and salmon extracts (FIG. 2). The same results were also observed in subgroups of seawater fish-allergic or freshwater fish-allergic subjects. For ImmunoCAP against the fish extracts, cod and salmon had similar diagnostic sensitivity while tuna was significantly less sensitive than the other tests. Grass carp parvalbumin was significantly more sensitive than rGad c 1, with both components being superior to the fish extracts. Comparison of individual tests was summarized in Table 2.

Correlation of IgE Level and Fish Tolerability

Figure 3:
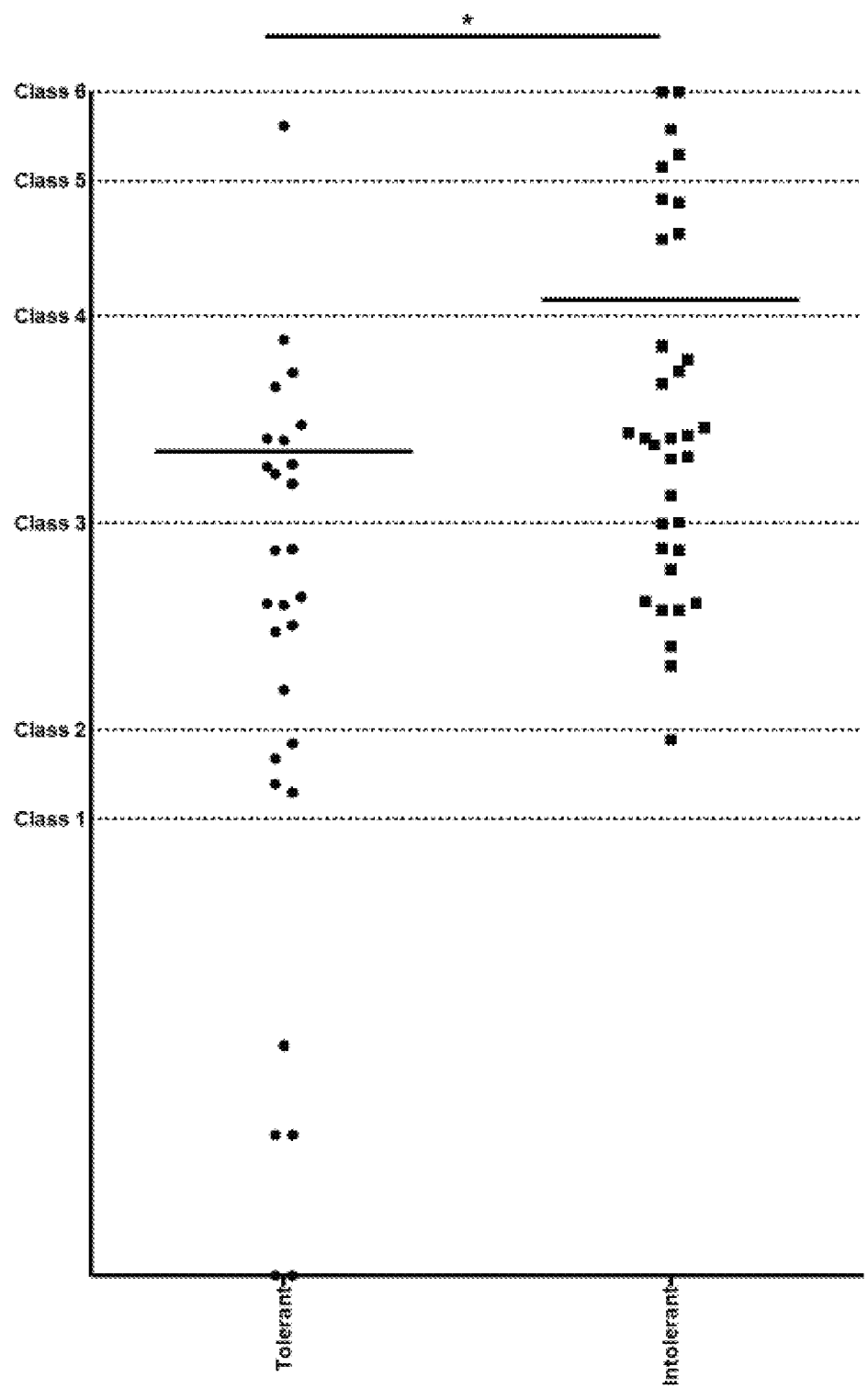
FIG. 3: IgE reactivity of subjects who tolerated at least one fish and those who were not able to tolerate any fish. * $p<0.05$.
Figure 4B:
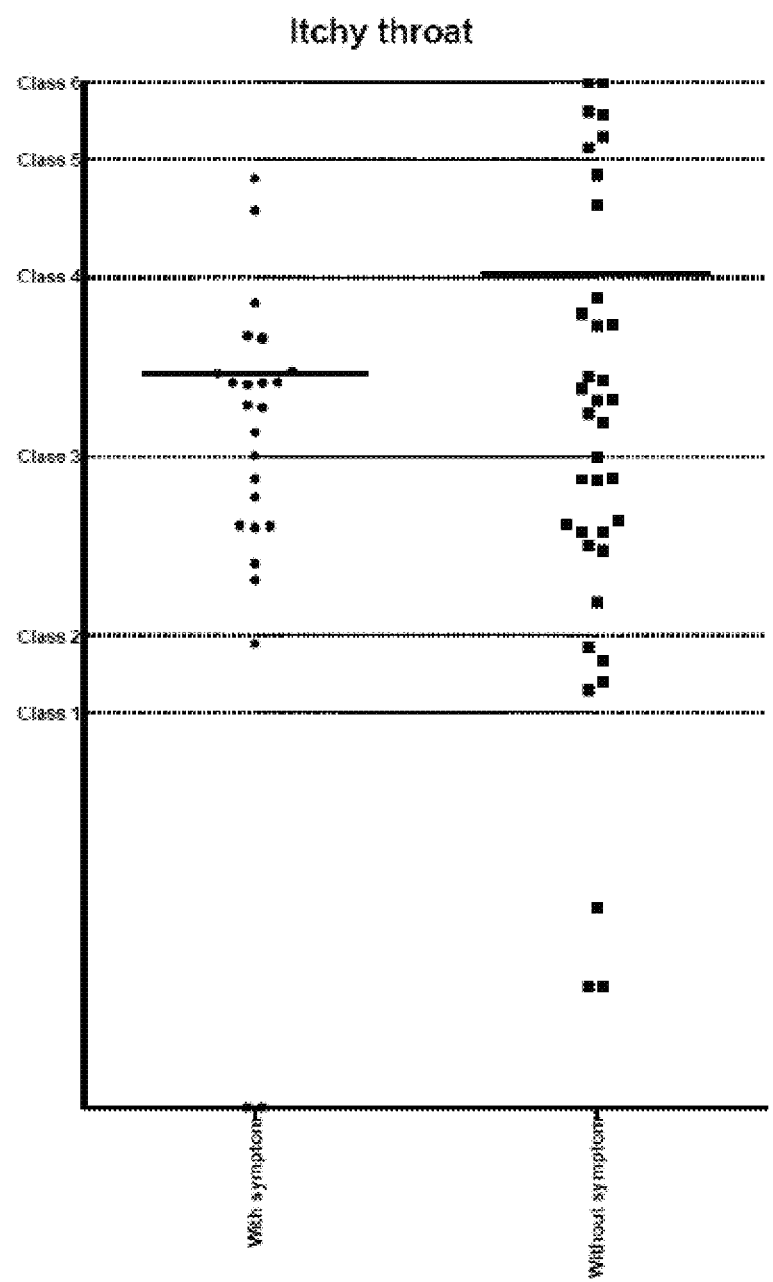
Figure 4E:
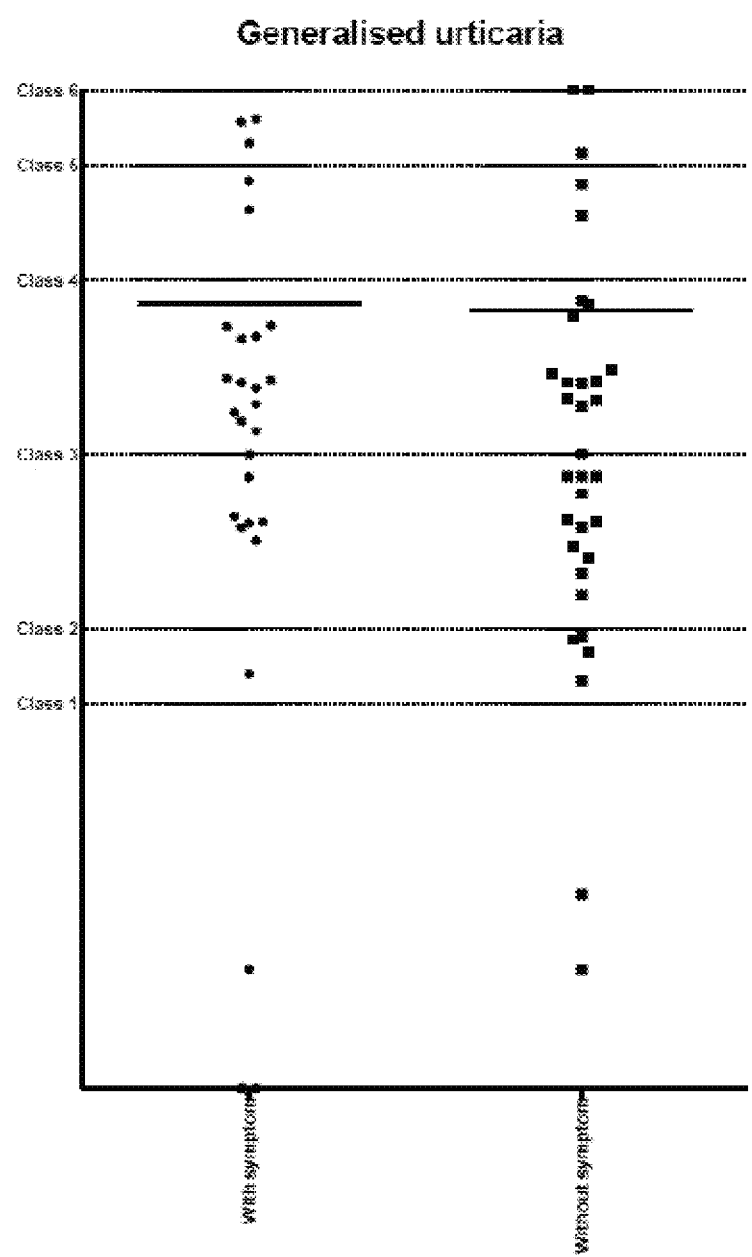
Figure 4G:
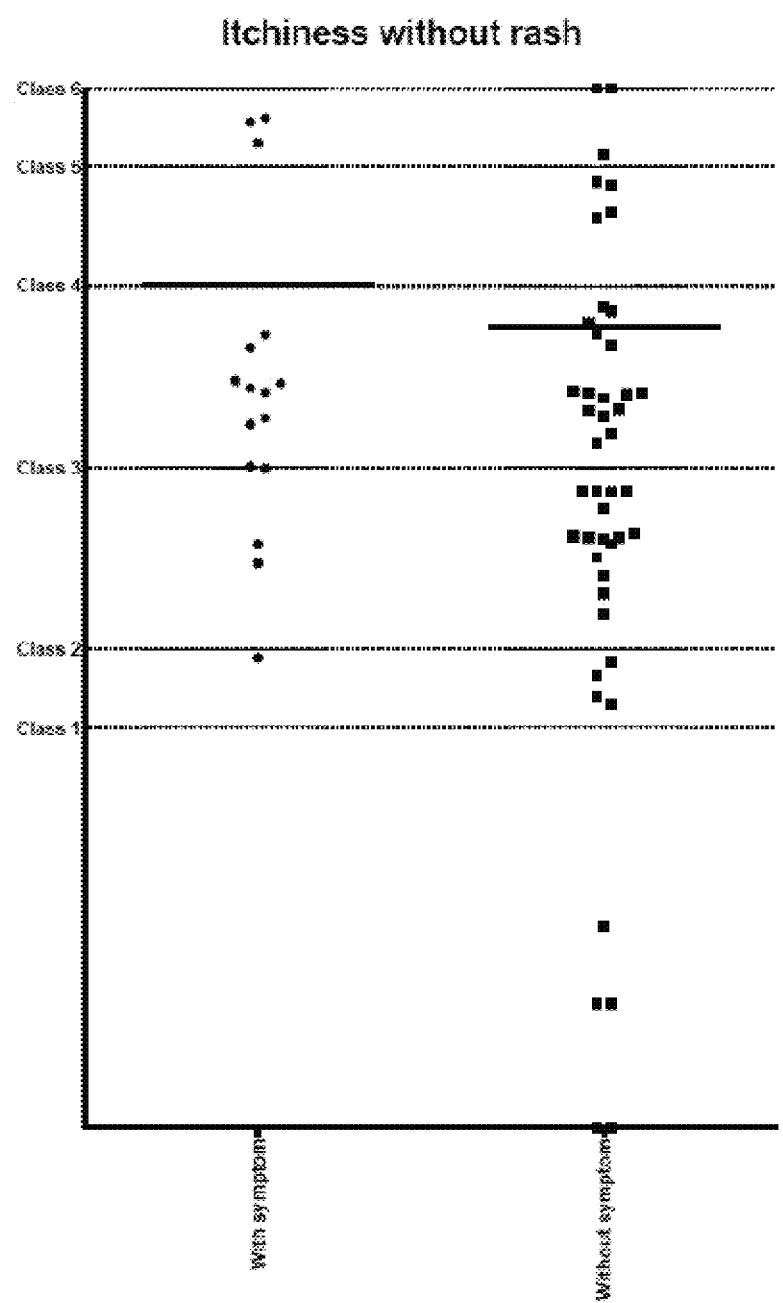
Figure 4H:
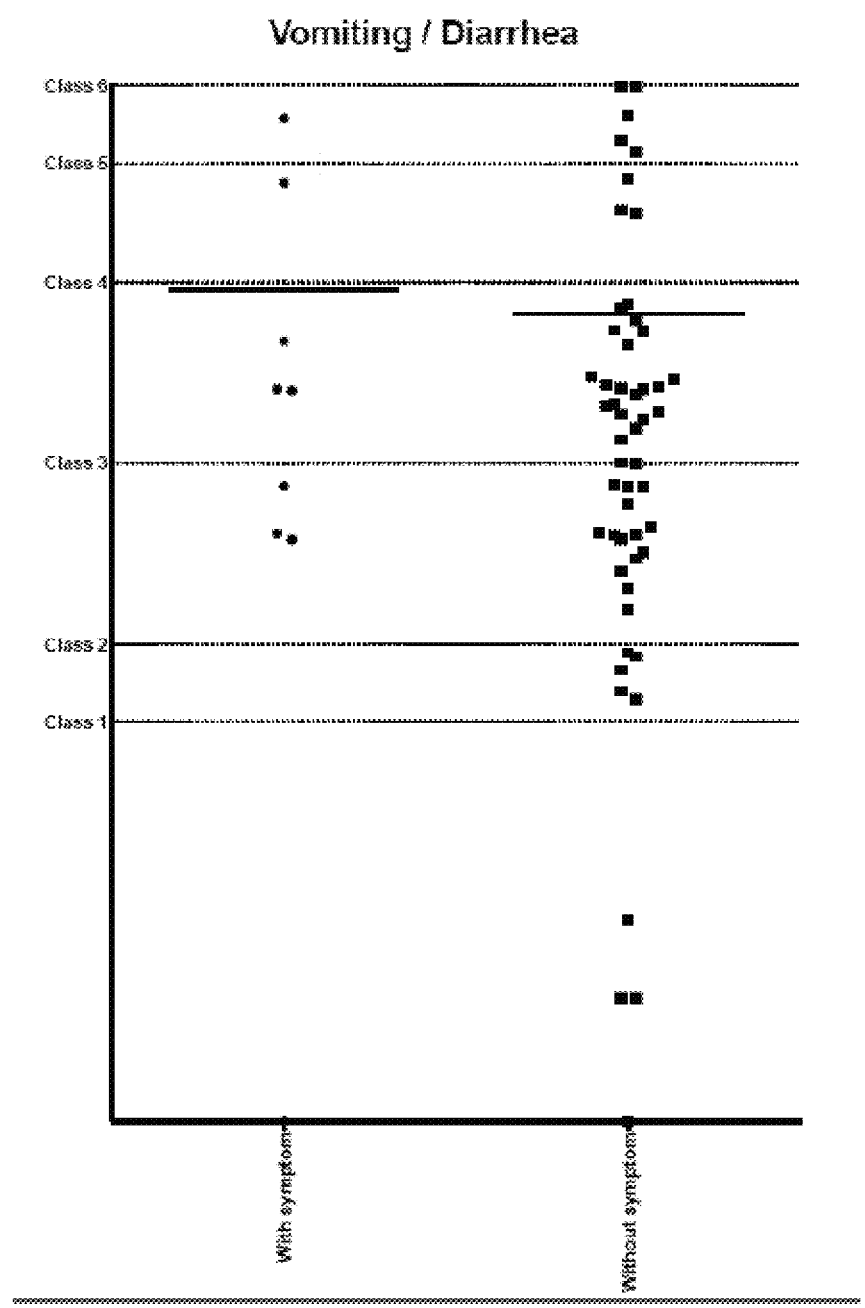
Figure 4I:
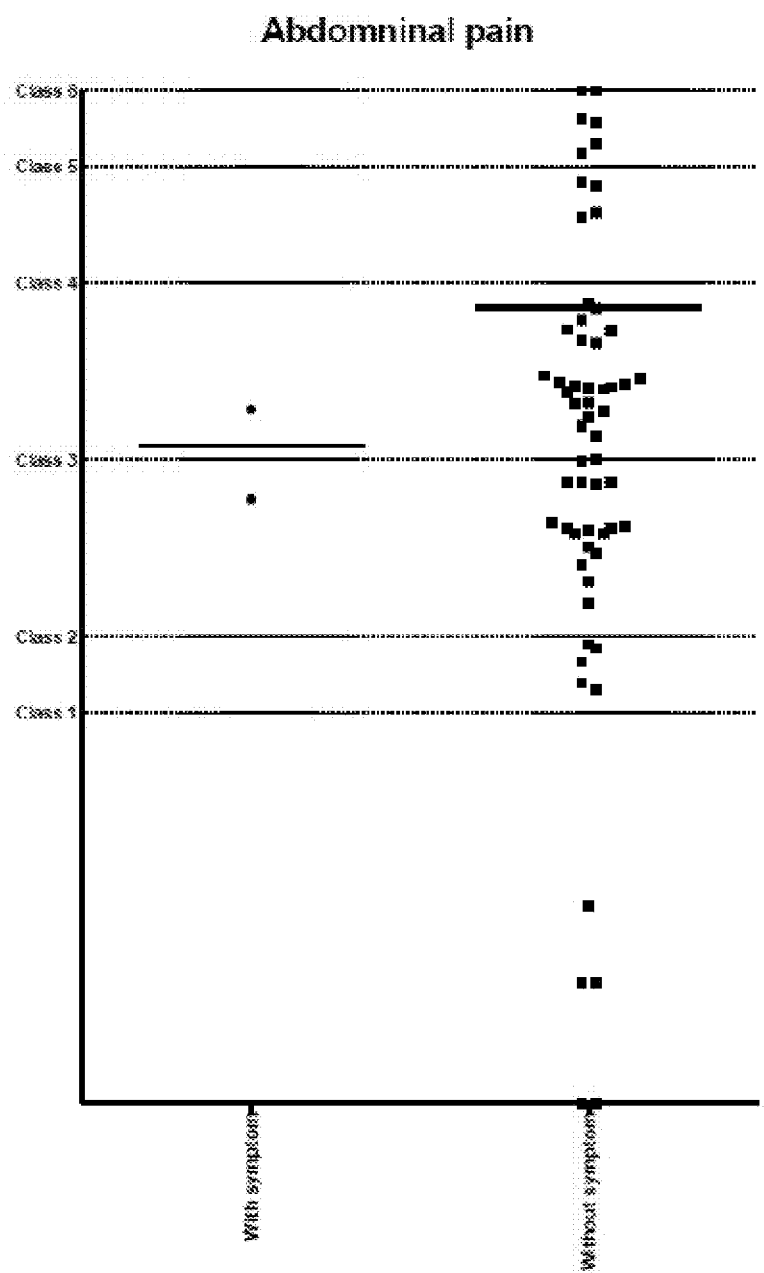
Figure 4J:
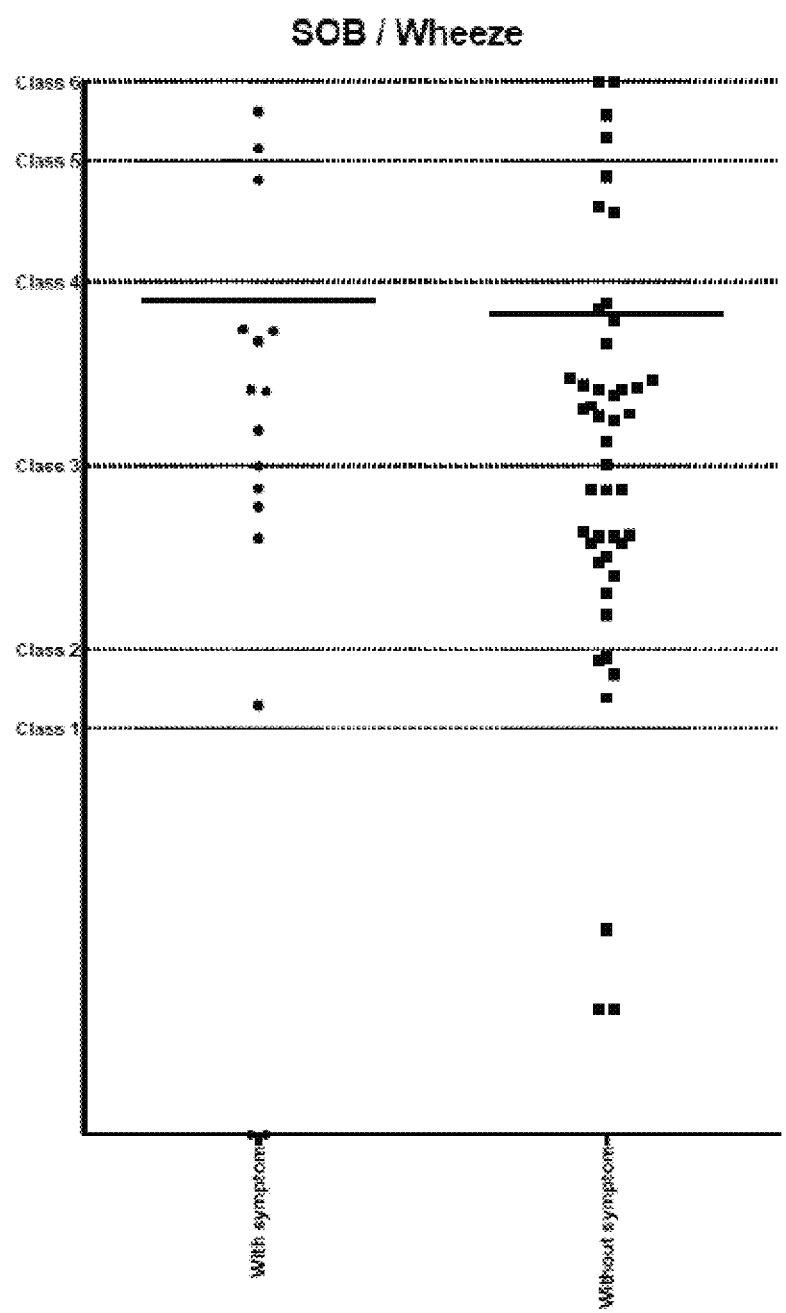

The IgE reactivity against grass carp parvalbumin was compared between subjects who were tolerance to at least one seawater fish (n=28) and those who were not tolerant to any fishes (n=34). IgE reactivity was significantly higher in the latter group (FIG. 3). The odds ratio for intolerance to any fish was 2.5 times higher when sIgE levels against grass carp parvalbumin exceeded 3.5 $kU_A/L$ (i.e., class 3 or above).

Correlation Between IgE Levels and Clinical Symptoms

The common clinical symptoms after fish intake or contact were evaluated for each subject and the IgE reactivity against grass carp parvalbumin was compared between those with or without clinical allergic reactions (FIG. 4a-4j). Only angioedema was found to correlate with sIgE levels, where subjects with angioedema had significantly higher sIgE levels. None of the other symptoms nor diagnosis of anaphylaxis was associated with IgE reactivity to grass carp parvalbumin. Alternatively, sensitization to enolase and aldolase were not associated with any clinical symptom (Table 3).

Cross-Inhibition ELISA Between Grass Carp and Cod Parvalbumin

Figure 6A:
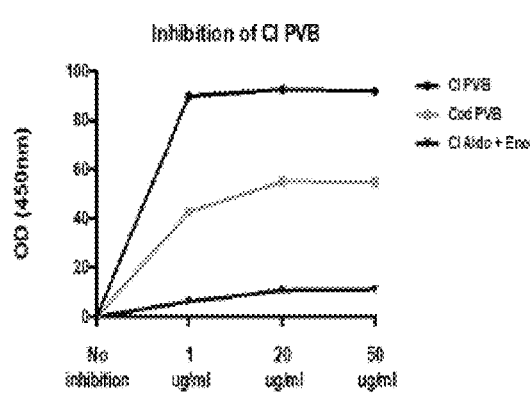
FIGS. 6A-6B: Cross-reactivity between *C. idella* parvalbumin and cod parvalbumin.
Figure 6B:
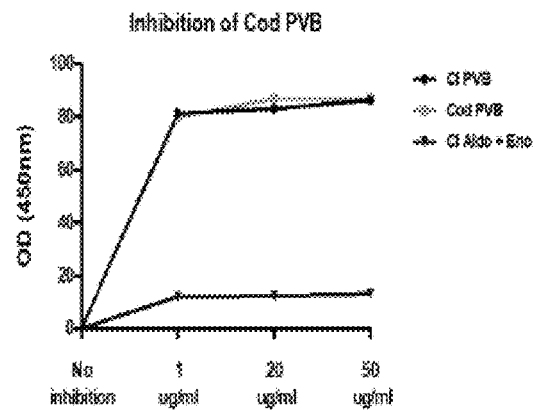

Grass carp parvalbumin inhibited IgE binding to immobilized cod parvalbumin for >80% even at the lowest concentration (1 μg/ml) (FIG. 6). Reciprocally, cod parvalbumin only inhibited 40% of IgE binding to C. idella parvalbumin at 1 μg/ml. The inhibition plateaued at 50% even when cod parvalbumin concentration increased to 50 μg/ml (FIG. 6). The positive control (grass carp parvalbumin) and negative control (grass carp enolase and aldolase) inhibited IgE binding to C. idella parvalbumin by 90% and 10% respectively.

Discussion

Diagnosis of fish allergy is complicated by the wide variety of fish species consumed all over the world. There are at least 33500 documented fish species, with at least 500 and 2000 species being caught or farmed for food respectively (website: fishbase.org). Meanwhile, sIgE tests by ImmunoCAP were only available for 27 fish species that represent a limited number of taxonomic families. Of all available species, cod is commonly used in diagnostics due to its cross-reactivity with common fish species[20]. However, these results suggest that the sensitivity of cod sIgE test was suboptimal in this study population, especially for subjects who were allergic to freshwater fishes. In contrast, allergen components from the grass carp Ctenopharyngodon idella demonstrated excellent diagnostic sensitivity. Grass carp allergens appeared to be representative of both seawater and freshwater fishes with the sensitivity exceeding 90% for both groups. Thus, the grass carp allergen component parvalbumin can be an optimal biomarker for fish allergy diagnosis.

Accurately predicting allergy to a specific species within a population of fish-allergic patients is a challenging task. Fish extracts were found to have low diagnostic specificity[21] due to the varying allergen content in fish extract and the presence of cross-reactive hypoallergenic parvalbumin isoforms. In light of this, CRD emerges as an attractive approach for fish allergy diagnosis. In this study population, a difference in IgE level against grass carp parvalbumin was observed between subjects who are able to tolerate at least one fish and those who are intolerant to all types of fish. Specific IgE concentration has been reported to have a positive correlation with oral food challenge outcomes[22-24] as well as the symptom-eliciting allergen dose[25]. Twenty-one of the 28 subjects with sIgE<3.5 $kU_A/L$ against grass carp parvalbumin had sIgE<0.35 $kU_A/L$ against tuna or salmon, and 17 of them reported clinical tolerance. It is thus possible that subjects with lower specific IgE titer may be able to tolerate fish species with low parvalbumin content such as salmon or tuna[12]. It is believed that sIgE level of 3.5 $kU_A/L$ can serve as a secondary cut-off to indicate whether a subject can tolerate fishes with relatively low allergenicity. Similar to previous studies concerning food allergy[26,27], this study did not find a significant correlation between sIgE level and symptom severity or anaphylaxis.

There are two possibilities in explaining the superior diagnostic sensitivity of grass carp when compared to fish extracts or even cod parvalbumin rGad c 1. Firstly, grass carp is an affordable and commonly consumed freshwater fish in South China region. It is marketed and consumed fresh, which might better retain the allergenicity and contribute to primary sensitization as opposed to imported frozen fishes like cod and salmon. However, this postulation is contradicted by the findings that patients who were allergic to seawater fish also developed high IgE titer against grass carp parvalbumin. The second possibility is that grass carp parvalbumin contained most of the IgE binding epitopes present in natural cod, tuna and salmon as previously suggested in the common carp parvalbumin[28]. It is thus more sensitive by encompassing a wider spectrum of IgE antibodies and extrapolating the IgE reactivity to both seawater and freshwater fishes. This explanation is also supported by the cross-inhibition ELISA results. For this reason, the use of grass carp parvalbumin for fish CRD is not only relevant to this population but also applicable to other parts of the world.

Figure 5:
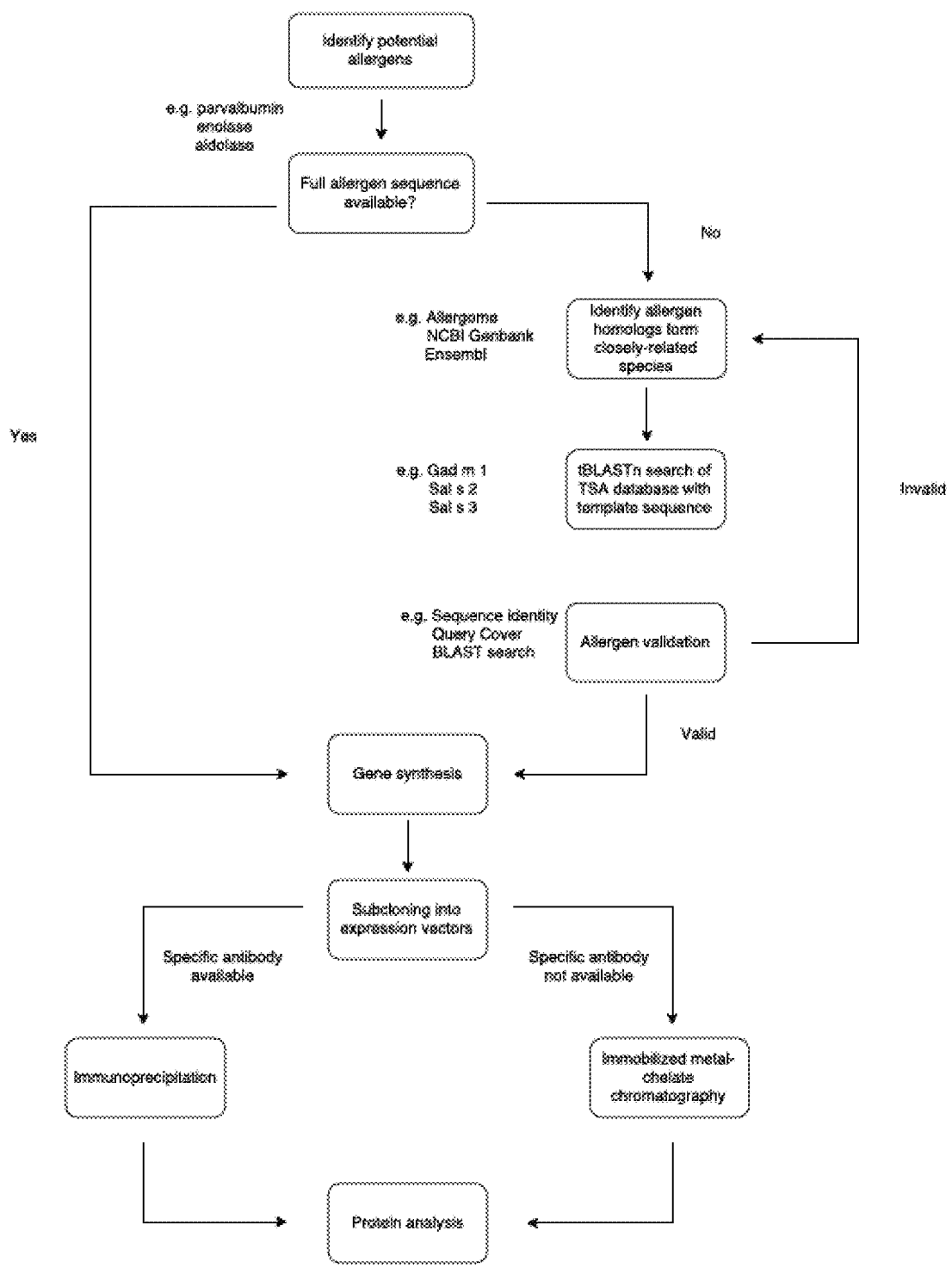
FIG. 5: General workflow of the in silico approach for the identification, validation, cloning and purification of recombinant allergens.

Despite their high sensitivity of grass carp CRD, three subjects did not react to any of grass carp allergen components or fish extracts. It might be explained by the mono-reactivity to a particular fish due to species-specific epitopes or allergens[29-32]. It is therefore essential to expand the knowledge to more fish species for the development of species-specific CRD[15,33,34]. A novel approach is hereby demonstrated to extract molecular information of fish allergens from TSA database, which could greatly reduce the time and resources required to screen and clone recombinant allergens using the conventional cDNA library method (FIG. 5). Nevertheless, it is important to validate the identity of allergens before using them for CRD. Allergen isoforms could be expressed simultaneously but clinical relevance is only linked with a few distinct isoforms. It is essential to eliminate non-allergenic isoforms through BLAST search. These findings indicate that allergen components derived by this novel approach had important diagnostic value. The methodology described in this study could serve as a model workflow to extrapolate allergen sequences from other fish species.

The importance of the minor allergens aldolase and enolase in fish allergy diagnosis requires further investigation. In contrast to a previous report[35], IgE reactivity to aldolase and enolase is rare in the study population. Given the high sequence homology of aldolase and enolase between grass carp and salmon, it is unlikely the non-reactivity is due to unique properties of grass carp aldolase and enolase. A more likely explanation is the difference in food processing methods between the Asian and western countries. Fish is usually steamed or added to congee for children, and both methods involved high temperature for an extended period. These preparatory methods would have degraded aldolase and enolase because both allergens were heat-sensitive[35]. The next goal is to investigate the IgE binding reactivity to aldolase and enolase in adults.

In summary, the present inventors cloned and synthesized recombinant allergens parvalbumin, enolase and aldolase from grass carp *C. idella* using a novel approach that made use of untagged sequence reads deposited at the TSA database. These recombinant allergens are robust biomarkers in CRD for fish allergy.

All patents, patent applications, and other publications, including GenBank Accession Numbers or equivalent sequence identification numbers, cited in this application are incorporated by reference in the entirety of their contents for all purposes.

Table 1 Allergen sequences derived from the TSA database of grass carp *C. idella*. Query cover indicates the percentage overlapped between the search sequence and aligned sequence. Identity indicates the percentage identical of amino acid sequence between the search sequence and aligned sequence.

TABLE 1

Allergen sequences derived from the TSA database of grass carp *C. Idella*. Query cover indicates the percentage overlapped between the search sequence and aligned sequence. Identity indicates the percentage identical of amino acid sequence between the search sequence and aligned sequence.

| Description | Potein Sequence | Query cover | Identity | Accession no. | BLAST search identity |
|---|---|---|---|---|---|
| *Parvalbumin* | | | | | |
| comp692324 | MAFAGILNEADITAALQACQAADSFKYKDFFAKVGLTAKSSDDIKKA FAVIDQDKSGFIEEEELKLFLQNFSAGARALTDAETKAFLKAGDSDG DGKIGVDEFAVLVKA (SEQ ID NO: 5) | 100% | 78% | GBKA01024099.1 | alpha-parvalbumin |
| c8509 | MAITDVLAASDISTAINACKAKDSFSPRTFFATVGLSKKSPREIEKI FKMLDQDKSGFIEQDELQLFLQNFSKGARALTAAETKAFLMAGDMDG DGKIGWEEFSALVNA (SEQ ID NO: 6) | 100% | 60% | GEUQ01014664.1 | thymic-like parvalbumin |
| comp185084 | MAITDVLAASDISTAINACKAKDSFSPRTFFATVGLSKKSPREIEKI FKMLDQDKSGFIEQDELQLFLQNFSKGARALTAAETKAFLMAGDMDG DGKIGWEEFSALVNA (SEQ ID NO: 7) | 100% | 60% | GBKA1021723.1 | thymic-like parvalbumin |
| c29630 | MAFAGVLNDADIAAALEACKAADSFNHKAFFAKVGLSAKSGDDVKKA FAIIDQDKSGFIEEDELKLFLQNFKADARALTDAETKIFLKAGDSDG DGKIGVDEFAALVKA (SEQ ID NO: 8) | 100% | 80% | GEUQ01040581.1/ GEUQ01041538.1 | beta-parvalbumin |
| *Enolase* | | | | | |
| c70816 | MSISKIHAREILDSRGNPTVEVDLYTSKGRFRAAVPSGASTGVHEAL ELRDGDKTRYLGKGTQKAVDHVNKEIAPKLIEKKFSVVDQEKIDKFM LELDGTENKSKFGANAILGVSLAVCKAGAAEKGVPLYRHIADLAGNK DVILPVPAFNVINGGSHAGNKLAMQEFMILPVGAKNFHEAMRIGAEV YHNLKNVIKAKYGKDATNVGDEGGFAPNILENNEALELLKSAIEKAG YPDKIIIGMDVAASEFFKSGKYDLDFKSPDDPKRHITGEQLGDLYKS FIKNYPVQSIEDPFDQDDWENWSKFTGSVDIQVVGDDLTVTNPKRIQ QACEKKACNCLLLKVNQIGSVTESIQACKLAQSNGWGVMVSHRSGET EDTFIADLVVGLCTGQIKTGAPCRSERLAKYNQLMRIEEELGDKAKF AGKDFRHPKL (SEQ ID NO: 9) | 99% | 91% | GEUQ01039200.1 | beta-enolase |
| comp52484 | MSISKIHAREILDSRGNPTVEVDLYTSKGRFRAAVPSGASTGVHEAL ELRDGDKTRYLGKGTQKAVDHVNKEIAPKLIEKKFSVVDQEKIDKFM LELDGTENKSKFGANAILGVSLAVCKAGAAEKGVPLYRHIADLAGNK DVILPVPAFNVINGGSHAGNKLAMQEFMILPVGAKNFHEAMRIGAEV YHNLKNVIKAKYGKDATNVGDEGGFAPNILENNEALELLKSAIEKAG YPDKIIIGMDVAASEFFKSGKYDLDFKSPDDPKRHITGEQLGDLYKS FIKNYPVQSIEDPFDQDDWENWSKFTGSVDIQVVGDDLTVTNPKRIQ QACEKKACNCLLLKVNQIGSVTESIQACKLAQSNGWGVMVSHRSGET EDTFIADLVVGLCTGQIKTGAPCRSERLAKYNQLMRIEEELGDKAKF AGKDFRHPKL (SEQ ID NO: 10) | 99% | 91% | GBKA01005072.1 | beta-enolase |
| c60301 | MSILKIHAREIFDSRGNPTVEVDLYTKKGLFRAAVPSGASTGIYEAL ELRDNDKTRYMGKGVSKAVEHINKTIAPALVSQSVSVLEQEKIDKLM LDMDGTENKSKFGANAILGVSLAVCKAGAAEKGVPLYRHIADLAGNP EVILPVPAFNVINGGSHAGNKLAMQEFMILPIGASNFKEAMRIGAEV YHNLKNVIKEKYGKDATNVGDEGGFAPNILENKEALELLKNAISKAG YTDKIVIGMDVAASEFYKGGKYDLDFKSPDDPSRYISPDQLADLYRS FVKDYPVVSIEDPFDQDDWEAWTNFTASTNIQVVGDDLTVTNPKRIA KRIAKAVSDKACNCLLLKVNQIGSVTESLQACKMAQSNGWGVMVSHR SGETEDTFIADLVVGLCTGQIKTGAPCRSERLAKYNQLLRIEEELGD KARFAGKNFRRP (SEQ ID NO: 11) | 100% | 85% | GEUQ01011316.1/ GEUQ0109226.1 | alpha-enolase |

TABLE 1-continued

Allergen sequences derived from the TSA database of grass carp *C. Idella*. Query cover indicates the percentage overlapped between the search sequence and aligned sequence. Identity indicates the percentage identical of amino acid sequence between the search sequence and aligned sequence.

| Description | Potein Sequence | Query cover | Identity | Accession no. | BLAST search identity |
|---|---|---|---|---|---|
| Aldolase | | | | | |
| c23832 | MPHAYPFLTPEQKKELSDIALRIVAPGKGILAADESTGSVAKRFQSI NAENTEENRRLYRQLLFTADDRVKPCIGGVILFHETLYQKADDGKLF SQLLKERGMVVGIKVDKGVVPLAGTNGETTTQGLDGLYERCAQYKKD GADFAKWRCVLKITSTTPSRLAIIENANVLARYASICQMHGIVPIVE PEILPDGDHDLKRCQYVTEKVLAAVYKALSDHHVYLEGTLLKPNMVT AGHSCSQKNTPQEIAMATVTALRRTVPPAVPGITFLSGGQSEEEATL NLNAMNKCPLHRPWALTFSYGRALQASALKAWGGKKENGKACQEEFI KRALNNSLACVGKYVSSGDKGAAAGESLFVANHAY (SEQ ID NO: 12) | 100% | 87% | GEUQ01036650.1 | Aldolase A |
| comp 72290 | MPHAYPFLTPEQKKELSDIALRIVAPGKGILAADESTGSVAKRFQSI NAENTEENRRLYRQLLFTADDRVKPCIGGVILFHETLYQKADDGKLF SQLLKERGMVVGIKVDKGVVPLAGTNGETTTQGLDGLYERCAQYKKD GADFAKWRCVLKITSTTPSRLAIIENANVLARYASICQMHGIVPIVE PEILPDGDHDLKRCQYVTEKVLAAVYKALSDHHVYLEGTLLKPNMVT AGHSCSQKNTPQEIAMATVTALRRTVPPAVPGITFLSGGQSEEEATL NLNAMNKCPLHRPWALTFSYGRALQASALKAWGGKKENGKACQEEFI KRALNNSLACVGKYVSSGDKGAAAGESLFVANHAY (SEQ ID NO: 13) | 100% | 87% | GBKA01026157.1 | Aldolase A |
| c95581 | MTHQYPALTTEQKKELQDIAQRIVAPGKGILAADESTGSMAKRLNPI GVENTEENRRLYRQILFSADERIDKCIGGVIFFHETLYQNADDGTCF AKMIKDRGIVVGIKVDKGVVPLAGTNGETTTQGLDGLSERCAQYKKD GADFAKWRCVLKISDTTPSELAIMENANVLARYASICQQNGIVPIVE PEILPDGDHDLKRCQYVTEKVLAACYKALSDHHVYLEGTLLKPNWVT AGHSCPTKYNSQEIAMATVTALRRTVPPAVTGVTFLSGGQSEEEASV NLNAINNCPLAKPWALTFSYGRALQASALAAWRGVKDNEKAATEAFI QRAEANGLAAQGKYVSSGTDGAAGQSLYVANHAY (SEQ ID NO: 14) | 100% | 79% | GBKA01026157.1 | Aldolase A |
| c39713 | MTHQYPALTTEQKKELQDIAQRIVAPGKGILAADESTGSMAKRLNPI GVENTEENRRLYRQILFSADERIDKCIGGVIFFHETLYQNADDGTCF AKMIKDRGIVVGIKVDKGVVPLAGTNGETTTQGLDGLSERCAQYKKD GADFAKWRCVLKISDTTPSELAIMENANVLARYASICQQNGIVPIVE PEILPDGDHDLKRCQYVTEKVLAACYKALSDHHVYLEGTLLKPNMVT AGHSCPTKYNSQEIAMATVTALRRTVPPAVTGVTFLSGGQSEEEASV NLNAINNCPLAKPWALTFSYGRALQASALAAWRGVKDNEKAATEAFI QRAEANGLAAQGKYVSSGTDGAAGQSLYVANHAY (SEQ ID NO: 15) | 100% | 79% | GBKA01002483.1 | Aldolase C |
| c23832 | MPHAYPFLTPEQKKELSDIALRIVAPGKGILAADESTGSVAKRFQSI NAENTEENRRLYRQLLFTADDRVKPCIGGVILFHETLYQKADDGKLF SQLLKERGMVVGIKVDKGVVPLAGTNGETTTQGLDGLYERCAQYKKD GADFAKWRCVLKITSTTPSRLAIIENANVIARYASICQMHGIVPIVE PEILPDGDHDLKRCQYVTEKVLAAVYKALSDHHVYLEGTLLKPNMVT AGHSCSQKNTPQEIAMATVTALRRTVPPAVPGITFLSGGQSEEEATL NLNAMNKCPLHRPWALTFSYGRALQASALKAWGGKKENGKACQEEFI KRALNNSLACVGKYVSSGDKGAAAGESLFVANHAY | 100% | 87% | GEUQ01036650.1 | Adolase A |
| comp 72290 | MPHAYPFLTPEQKKELSDIALRIVAPGKGILAADESTGSVAKRFQSI NAENTEENRRLYRQLLFTADDRVKPCIGGVILFHETLYQKADDGKLF SQLLKERGMVVGIKVDKGVVPLAGTNGETTTQGLDGLYERCAQYKKD GADFAKWRCVLKITSTTPSRLAIIENANVLARYASICQMHGIVPIVE PEILPDGDHDLKRCQYVTEKVLAAVYKALSDHHVYLEGTLLKPNMVT AGHSCSQKNTPQEIAMATVTALRRTVPPAVPGITFLSGGQSEEEATL NLNAMNKCPLHRPWALTFSYGRALQASALKAWGGKKENGKACQEEFI KRALNNSLACVGKYVSSGDKGAAAGESLFVANHAY | 100% | 87% | GBKA01026157.1 | Adolase A |
| c95581 | MTHQYPALTTEQKKELQDIAQRIVAPGKGILAADESTGSMAKRLNPI GVENTEENRRLYRQILFSADERIDKCIGGVIFFHETLYQNADDGTCF AKMIKDRGIVVGIKVDKGVVPLAGTNGETTTQGLDGLSERCAQYKKD GADFAKWRCVLKISDTTPSELAIMENANVLARYASICQQNGIVPIVE PEILPDGDHDLKRCQYVTEKVLAACYKALSDHHVYLEGTLLKPNWVT AGHSCPTKYNSQEIAMATVTALRRTVPPAVTGVTFLSGGQSEEEASV NLNAINNCPLAKPWALTFSYGRALQASALAAWRGVKDNEKAATEAFI QRAEANGLAAQGKYVSSGTDGAAGQSLYVANHAY | 100% | 79% | GEUQ01009493.1 | Adolase C |
| c39713 | MTHQYPALTTEQKKELQDIAQRIVAPGKGILAADESTGSMAKRLNPI GVENTEENRRLYRQILFSADERIDKCIGGVIFFHETLYQNADDGTCF AKMIKDRGIVVGIKVDKGVVPLAGTNGETTTQGLDGLSERCAQYKKD GADFAKWRCVLKISDTTPSELAIMENANVLARYASICQQNGIVPIVE | 100% | 79% | GBKA01002483.1 | Adolase C |

TABLE 1-continued

Allergen sequences derived from the TSA database of grass carp *C. Idella*. Query cover indicates the percentage overlapped between the search sequence and aligned sequence. Identity indicates the percentage identical of amino acid sequence between the search sequence and aligned sequence.

| Description | Potein Sequence | Query cover | Identity | Accession no. | BLAST search identity |
|---|---|---|---|---|---|
| | PEILPDGDHDLKRCQYVTEKVLAACYKALSDHHVYLEGTLLKPNMVT AGHSCPTKYNSQEIAMATVTALRRTVPPAVTGVTFLSGGQSEEEASV NLNAINNCPLAKPWALTFSYGRALQASALAAWRGVKDNEKAATEAFI QRAEANGLAAQGKYVSSGTDGAAGQSLYVANHAY | | | | |

TABLE 2

Detailed in-parallel comparison of individual diagnostic tests. Other than the total number of fish allergic subjects (n = 62), the subjects are further divided into freshwater fish allergic subjects (n = 45) and seawater fish allergic subjects (n = 53). P-values indicate statistical significance by McNemar's chi-square test.

OVERALL

| | Tuna Positive | Tuna Negative | Totals |
|---|---|---|---|
| Cod Positive | 31 | 9 | 40 |
| Cod Negative | 1 | 21 | 22 |
| Totals | 32 | 60 | 62 |
| p-value | 0.027 | | |

| | Salmon Positive | Salmon Negative | Totals |
|---|---|---|---|
| Cod Positive | 34 | 6 | 40 |
| Cod Negative | 3 | 19 | 22 |
| Totals | 37 | 25 | 62 |
| p-value | 0.505 | | |

| | Salmon Positive | Salmon Negative | Totals |
|---|---|---|---|
| Tuna Positive | 30 | 2 | 32 |
| Tuna Negative | 7 | 23 | 30 |
| Totals | 37 | 25 | 62 |
| p-value | 0.182 | | |

| | Cod Positive | Cod Negative | Totals |
|---|---|---|---|
| rGad c 1 Positive | 39 | 10 | 49 |
| rGad c 1 Negative | 1 | 12 | 13 |
| Totals | 40 | 22 | 62 |
| p-value | 0.015 | | |

| | GC PV Positive | GC PV Negative | Totals |
|---|---|---|---|
| rGad c 1 Positive | 49 | 0 | 49 |
| rGad c 1 Negative | 8 | 5 | 13 |
| Totals | 57 | 5 | 62 |
| p-value | 0.013 | | |

| | GC PV Positive | GC PV Negative | Totals |
|---|---|---|---|
| Salmon Positive | 36 | 1 | 37 |
| Salmon Negative | 14 | 11 | 25 |
| Totals | 50 | 12 | 62 |
| p-value | 0.002 | | |

| | GC PV Positive | GC PV Negative | Totals |
|---|---|---|---|
| Tuna Positive | 31 | 1 | 32 |
| Tuna Negative | 18 | 12 | 30 |
| Totals | 49 | 13 | 62 |
| p-value | <0.001 | | |

| | Cod Positive | Cod Negative | Totals |
|---|---|---|---|
| GC PV Positive | 40 | 17 | 57 |
| GC PV Negative | 0 | 5 | 5 |
| Totals | 40 | 22 | 62 |
| p-value | <0.001 | | |

| | GC PV Positive | GC PV Negative | Totals |
|---|---|---|---|
| Tuna Positive | 32 | 0 | 32 |
| Tuna Negative | 25 | 5 | 30 |
| Totals | 57 | 5 | 62 |
| p-value | <0.001 | | |

| | GC PV Positive | GC PV Negative | Totals |
|---|---|---|---|
| Salmon Positive | 37 | 0 | 37 |
| Salmon Negative | 20 | 5 | 25 |
| Totals | 57 | 5 | 62 |
| p-value | <0.001 | | |

FRESHWATER

| | Tuna Positive | Tuna Negative | Totals |
|---|---|---|---|
| Cod Positive | 22 | 6 | 28 |
| Cod Negative | 1 | 16 | 17 |
| Totals | 23 | 22 | 45 |
| p-value | 0.131 | | |

| | Salmon Positive | Salmon Negative | Totals |
|---|---|---|---|
| Cod Positive | 23 | 5 | 28 |
| Cod Negative | 31 | 14 | 17 |
| Totals | 26 | 19 | 45 |
| p-value | 0.724 | | |

| | Salmon Positive | Salmon Negative | Totals |
|---|---|---|---|
| Tuna Positive | 21 | 2 | 23 |
| Tuna Negative | 5 | 17 | 22 |
| Totals | 26 | 19 | 45 |
| p-value | 0.450 | | |

| | Cod Positive | Cod Negative | Totals |
|---|---|---|---|
| rGad c 1 Positive | 28 | 8 | 36 |
| rGad c 1 Negative | 0 | 9 | 9 |
| Totals | 28 | 17 | 45 |
| p-value | 0.013 | | |

TABLE 2-continued

Detailed in-parallel comparison of individual diagnostic tests. Other than the total number of fish allergic subjects (n = 62), the subjects are further divided into freshwater fish allergic subjects (n = 45) and seawater fish allergic subjects (n = 53). P-values indicate statistical significance by McNemar's chi-square test.

|  | CGCPV Positive | GC PV Negative | Totals |
|---|---|---|---|
| rGad c 1 Positive | 36 | 0 | 36 |
| rGad c 1 Negative | 7 | 2 | 9 |
| Totals | 43 | 2 | 45 |
| p-value | 0.023 | | |

|  | rGad c1 Positive | rGad c1 Negative | Totals |
|---|---|---|---|
| Salmon Positive | 25 | 1 | 26 |
| Salmon Negative | 11 | 8 | 19 |
| Totals | 36 | 9 | 62 |
| p-value | 0.009 | | |

|  | rGad c1 Positive | rGad c1 Negative | Totals |
|---|---|---|---|
| Tuna Positive | 23 | 0 | 23 |
| Tuna Negative | 13 | 9 | 22 |
| Totals | 26 | 9 | 45 |
| p-value | <0.001 | | |

|  | Cod Positive | Cod Negative | Totals |
|---|---|---|---|
| GC PV Positive | 40 | 17 | 57 |
| GC PV Negative | 0 | 5 | 5 |
| Totals | 40 | 22 | 62 |
| p-value | <0.001 | | |

|  | GC PV Positive | GC PV Negative | Totals |
|---|---|---|---|
| Tuna Positive | 23 | 0 | 23 |
| Tuna Negative | 20 | 2 | 22 |
| Totals | 43 | 2 | 45 |
| p-value | <0.001 | | |

|  | GC PV Positive | GC PV Negative | Totals |
|---|---|---|---|
| Salmon Positive | 26 | 0 | 26 |
| Salmon Negative | 17 | 2 | 19 |
| Totals | 43 | 2 | 45 |
| p-value | <0.001 | | |

SEAWATER

|  | Tuna Positive | Tuna Negative | Totals |
|---|---|---|---|
| Cod Positive | 28 | 8 | 36 |
| Cod Negative | 0 | 17 | 27 |
| Totals | 28 | 25 | 53 |
| p-value | 0.013 | | |

|  | Salmon Positive | Salmon Negative | Totals |
|---|---|---|---|
| Cod Positive | 31 | 5 | 36 |
| Cod Negative | 2 | 15 | 17 |
| Totals | 33 | 20 | 53 |
| p-value | 0.450 | | |

|  | Salmon Positive | Salmon Negative | Totals |
|---|---|---|---|
| Tuna Positive | 26 | 2 | 28 |
| Tuna Negative | 7 | 18 | 25 |
| Totals | 33 | 20 | 53 |
| p-value | 0.12 | | |

TABLE 2-continued

Detailed in-parallel comparison of individual diagnostic tests. Other than the total number of fish allergic subjects (n = 62), the subjects are further divided into freshwater fish allergic subjects (n = 45) and seawater fish allergic subjects (n = 53). P-values indicate statistical significance by McNemar's chi-square test.

|  | Cod Positive | Cod Negative | Totals |
|---|---|---|---|
| rGad c 1 Positive | 35 | 8 | 43 |
| rGad c 1 Negative | 1 | 9 | 10 |
| Totals | 36 | 17 | 53 |
| p-value | 0.046 | | |

|  | GC PV Positive | GC PV Negative | Totals |
|---|---|---|---|
| rGad c 1 Positive | 43 | 0 | 43 |
| rGad c 1 Negative | 6 | 2 | 8 |
| Totals | 49 | 2 | 53 |
| p-value | 0.041 | | |

|  | rGad c1 Positive | rGad c1 Negative | Totals |
|---|---|---|---|
| Salmon Positive | 31 | 2 | 33 |
| Salmon Negative | 12 | 8 | 20 |
| Totals | 43 | 10 | 43 |
| p-value | 0.016 | | |

|  | rGad c1 Positive | rGad c1 Negative | Totals |
|---|---|---|---|
| Tuna Positive | 27 | 1 | 28 |
| Tuna Negative | 16 | 9 | 25 |
| Totals | 43 | 10 | 53 |
| p-value | <0.001 | | |

|  | Cod Positive | Cod Negative | Totals |
|---|---|---|---|
| GC PV Positive | 36 | 13 | 49 |
| GC PV Negative | 0 | 4 | 4 |
| Totals | 40 | 13 | 53 |
| p-value | <0.001 | | |

|  | GC PV Positive | GC PV Negative | Totals |
|---|---|---|---|
| Tuna Positive | 28 | 0 | 28 |
| Tuna Negative | 21 | 4 | 25 |
| Totals | 49 | 4 | 53 |
| p-value | <0.001 | | |

|  | GC PV Positive | GC PV Negative | Totals |
|---|---|---|---|
| Salmon Positive | 33 | 0 | 33 |
| Salmon Negative | 16 | 4 | 20 |
| Totals | 49 | 4 | 53 |
| p-value | <0.001 | | |

TABLE 3

Associations between clinical symptoms and IgE sensitization to the minor allergens enolase and aldolase. P-value indicates statistical significance by chi-square test.

|  | Anaphylaxis | No anaphylaxis |  | Facial rash | No facial rash |
|---|---|---|---|---|---|
| Eno/Aldo | 5 | 16 | Eno/Aldo | 7 | 14 |
| PV only | 15 | 26 | PV only | 19 | 22 |
| p-value | 0.3085 |  | p-value | 0.3259 |  |

|  | Angioedema | No angioedema |  | Itchiness without rash | No itchiness without rash |
|---|---|---|---|---|---|
| Eno/Aldo | 18 | 3 | Eno/Aldo | 6 | 15 |
| PV only | 28 | 13 | PV only | 10 | 31 |
| p-value | 0.1379 |  | p-value | 0.7218 |  |

|  | Itchy throat | No itchy throat |  | Vomiting/diarrhea | No vomiting/diarrhea |
|---|---|---|---|---|---|
| Eno/Aldo | 6 | 15 | Eno/Aldo | 1 | 20 |
| PV only | 19 | 22 | PV only | 8 | 33 |
| p-value | 0.177 |  | p-value | 0.1187 |  |

|  | Localised urticaria | No localised urticaria |  | Abdominal pain | No abdominalpain |
|---|---|---|---|---|---|
| Eno/Aldo | 4 | 17 | Eno/Aldo | 1 | 20 |
| PV only | 9 | 32 | PV only | 1 | 40 |
| p-value | 0.7905 |  | p-value | 0.6242 |  |

|  | Generalized urticaria | No generalised urticaria |  | SOB/wheeze | No SOB/wheeze |
|---|---|---|---|---|---|
| Eno/Aldo | 13 | 8 | Eno/Aldo | 3 | 18 |
| PV only | 15 | 26 | PV only | 13 | 28 |
| p-value | 0.058 |  | p-value | 0.1379 |  |

TABLE 4

Demographics of the study population

| Subjects' clinical profile | Mean/Percentage | Range |
|---|---|---|
| Age (n = 62) | 7.0 years | 1.4-20 years |
| Male (n = 62) | 66% |  |
| Age of 1st reaction (n = 47) | 10 months | 6 months-3 years |
| FW as 1st allergic fish (n = 48) | 56% |  |
| SPT fish (n = 48) | 5.7 mm | 0-17 mm |
| SPT salmon (n = 46) | 3.8 mm | 0-17 mm |
| Asthma (n = 55) | 45.5% |  |
| Allergic rhinitis (n = 55) | 67.3% |  |
| Eczema (n = 55) | 96.4% |  |

TABLE 4-continued

Demographics of the study population

| Symptoms | Percentage |
|---|---|
| Itchy throat | 40.3% |
| Angioedema | 74.2% |
| Facial rash | 71.0% |
| Generalized urticaria | 45.2% |
| GI symptoms | 17.7% |
| SOB | 25.8% |
| Anaphylaxis | 30.6% |

TABLE 5

Sensitization profile and clinical features of the study population

| Patient | Sex | Age | Skin Prick Test (mm) Fish Mix | Skin Prick Test (mm) Salmon | Skin Prick Test (mm) Cod | ImmunoCAP specific IgE ($kU_A/L$) Tuna | ImmunoCAP specific IgE ($kU_A/L$) Salmon | ImmunoCAP specific IgE ($kU_A/L$) rGad c 1 | Grass carp CRD specific IgE ($kU_A/L$) Parvalbumin | Grass carp CRD specific IgE ($kU_A/L$) Enolase | Grass carp CRD specific IgE ($kU_A/L$) Aldolase | Allergic to SW | Allergic to FW | Tolerant to SW |
|---|---|---|---|---|---|---|---|---|---|---|---|---|---|---|
| 1 | F | 14 | 6 | 5 | 1.45 | 0.51 | 0.78 | 2.32 | 5.53 | 0.40 | 0.41 | * | * | * |
| 2 | M | 14 | 7 | 2 | 0.39 | 0.44 | 0.22 | 0.53 | 1.97 | 0.58 | 0.11 | * | * | * |
| 3 | M | 14 | 9 | 5 | 0.17 | 0.07 | 0.08 | 0.68 | 1.34 | 0.03 | 0.00 | * | * |  |
| 4 | M | 3 | 2 | 2 | 0.38 | 0.59 | 0.48 | 0.58 | 0.95 | 0.11 | 0.00 | * |  | * |
| 5 | F | 4 | 3 | 3 | 0.34 | 0.22 | 0.77 | 0.68 | 2.83 | 0.03 | 0.02 | * | * | * |
| 6 | M | 9 | 4 | 0 | 1.77 | 1.47 | 2.46 | 5.75 | 7.54 | 0.00 | 0.03 | * |  | * |
| 7 | F | 4 | 5 | 0 | 59.4 | 22.0 | 66.3 | 100.0 | 74.6 | 0.23 | 2.17 | * | * |  |
| 8 | M | 14 | 4 | 4 | 0.16 | 0.25 | 0.07 | 0.20 | 0.65 | 0.19 | 0.09 |  | * |  |
| 9 | F | 20 | 7 | 3 | 1.48 | 8.65 | 8.38 | 0.72 | 2.44 | 0.12 | 0.07 | * | * |  |
| 10 | M | 2 | 0 | 0 | 0.03 | 0.01 | 0.02 | 0.43 | 1.85 | 0.00 | 0.04 | * |  | * |
| 11 | M | 6 | 9 | 0 | 0.35 | 0.17 | 0.05 | 1.23 | 2.86 | 0.19 | 0.00 |  | * | * |
| 12 | F | 5 | 5 | 5 | 7.5 | 2.56 | 1.09 | 1.41 | 5.14 | 10.4 | 0.07 | 0.05 | * | * |

TABLE 5-continued

Sensitization profile and clinical features of the study population

| Patient | Sex | Age | | | | | | | | | | | | | | | | | |
|---|---|---|---|---|---|---|---|---|---|---|---|---|---|---|---|---|---|---|---|
| 13 | F | 7 | 0 | 0 | 2.48 | 6.61 | 6.96 | 4.37 | 7.37 | 0.68 | 0.10 | * | * | | | | | | |
| 14 | M | 2 | 0 | 0 | 0.10 | 0.04 | 0.83 | 0.07 | 0.46 | 0.00 | 0.00 | * | * | * | | | | | |
| 15 | M | 10 | 6.5 | 5.5 | 1.40 | 0.21 | 1.09 | 3.71 | 6.69 | 0.00 | 0.31 | * | * | * | | | | | |
| 16 | M | 14 | 0 | 0 | 0.01 | 0.01 | 0.01 | 0.01 | 0.01 | 0.07 | 0.03 | * | * | | | | | | |
| 17 | M | 11 | 4 | 3.5 | 3.09 | 0.32 | 0.27 | 4.66 | 4.34 | 0.64 | 0.80 | * | * | | | | | | |
| 18 | F | 12 | 8.5 | 1.5 | 0.31 | 0.04 | 0.07 | 3.07 | 2.87 | 0.39 | 0.12 | | * | | | | | | |
| 19 | M | 7 | 10 | 12 | 3.41 | 0.99 | 2.58 | 10.7 | 11.5 | 0.20 | 0.12 | * | * | | | | | | |
| 20 | M | 10 | 6 | 6 | 6.84 | 0.71 | 3.38 | 21.7 | 31.8 | 0.00 | 0.04 | * | * | | | | | | |
| 21 | M | 13 | 7 | 3 | 0.09 | 0.09 | 0.07 | 0.71 | 1.88 | 0.00 | 0.00 | * | * | | | | | | |
| 22 | F | 9 | 11 | 4.5 | 0.02 | 0.03 | 0.00 | 0.20 | 1.15 | 0.00 | 0.05 | * | * | | | | | | |
| 23 | M | 10 | 0 | 0 | 0.28 | 0.30 | 0.22 | 0.54 | 0.43 | 0.15 | 0.39 | * | | * | | | | | |
| 24 | M | 5 | 4 | 7 | 11.4 | 11.6 | 16.1 | 32.7 | 55.8 | 0.00 | 0.12 | * | | | | | | | |
| 25 | M | 5 | 6 | 4 | 0.53 | 0.31 | 0.29 | 1.37 | 1.78 | 0.00 | 0.07 | * | | | | | | | |
| 26 | M | 2 | 0 | 0 | 0.22 | 0.17 | 0.17 | 0.32 | 0.63 | 0.34 | 0.08 | * | * | * | | | | | |
| 27 | M | 3 | 9 | 5 | 2.58 | 0.74 | 1.34 | 6.02 | 5.14 | 0.11 | 0.04 | * | * | * | | | | | |
| 28 | F | 2 | N.D. | N.D. | 0.20 | 0.10 | 0.01 | 0.22 | 3.48 | 0.07 | 0.14 | | * | | | | | | |
| 29 | M | 7 | N.D. | N.D. | 1.53 | 1.40 | 2.72 | 2.36 | 11.3 | 0.00 | 0.03 | * | * | * | | | | | |
| 30 | F | 11 | 17 | 17 | 1.97 | 0.57 | 1.96 | 12.2 | 13.9 | 0.00 | 0.00 | * | * | | | | | | |
| 31 | F | 13 | 10 | 9 | 0.91 | 0.89 | 1.22 | 4.22 | 5.78 | 0.00 | 0.00 | * | * | | | | | | |
| 32 | F | 10 | 8 | 6 | 0.87 | 0.21 | 0.47 | 5.25 | 5.88 | 0.06 | 0.02 | * | | | | | | | |
| 33 | F | 6 | 5 | 9 | 0.09 | 0.34 | 0.13 | 0.32 | 4.76 | 0.02 | 0.15 | * | * | * | | | | | |
| 34 | M | 22 m | 0 | 0 | 0.13 | 0.06 | 0.00 | 1.60 | 7.08 | 0.23 | 0.63 | * | * | | | | | | |
| 35 | M | 4 | N.D. | N.D. | 49.4 | 4.29 | 15.5 | 97.4 | >100 | 0.27 | 1.36 | * | | | | | | | |
| 36 | M | 12 | 7.5 | 7 | 0.83 | 0.54 | 1.95 | 1.01 | 3.52 | 1.65 | 1.33 | | * | | | | | | |
| 37 | F | 18 m | N.D. | N.D. | 1.84 | 0.68 | 1.01 | 7.83 | 42.23 | 0.00 | 0.00 | * | | | | | | | |
| 38 | M | 18 m | N.D. | N.D. | 0.18 | 0.17 | 0.24 | 0.35 | 1.50 | 0.00 | 0.02 | * | * | * | | | | | |
| 39 | M | 5 | 5 | 5 | 0.03 | 0.05 | 0.04 | 0.49 | 1.78 | 0.00 | 0.28 | * | * | | | | | | |
| 40 | M | 34 m | 15 | 5 | 63.0 | 28.9 | 52.5 | >100 | >100 | 0.08 | 0.00 | * | | | | | | | |
| 41 | M | 3 | 7 | 0 | 0.86 | 0.59 | 0.17 | 1.01 | 1.58 | 0.44 | 0.04 | * | * | * | | | | | |
| 42 | M | 4 | N.D. | N.D. | 21.4 | 8.66 | 59.0 | 42.2 | 61.45 | 0.62 | 1.90 | * | * | | | | | | |
| 43 | M | 31 m | N.D. | N.D. | 1.62 | 0.22 | 0.78 | 4.66 | 6.92 | 0.36 | 0.87 | * | * | | | | | | |
| 44 | F | 8 | 0 | 0 | 0.00 | 0.00 | 0.00 | 0.00 | 0.03 | 0.51 | 0.43 | | | * | | | | | |
| 45 | F | 17 m | 0 | 0 | 0.00 | 0.00 | 0.00 | 0.00 | 0.06 | 0.07 | 0.36 | * | | | | | | | |
| 46 | F | 14 | 7 | 7 | 1.39 | 0.78 | 0.64 | 2.01 | 1.87 | 0.75 | 0.21 | * | * | * | | | | | |
| 47 | F | 29 m | 3 | 4 | 1.03 | 0.53 | 0.55 | 4.32 | 6.45 | 0.27 | 0.38 | * | | | | | | | |
| 48 | M | 11 | 15 | 11 | 0.97 | 0.12 | 0.42 | 3.90 | 6.77 | 0.17 | 0.13 | * | | * | | | | | |
| 49 | M | 29 m | N.D. | N.D. | 0.00 | 0.00 | 0.00 | 0.00 | 0.00 | 0.15 | 0.13 | * | | | | | | | |
| 50 | M | 31 m | 14 | N.D. | 10.5 | 3.41 | 4.44 | 74.1 | 76.8 | 0.55 | 0.92 | * | | | | | | | |
| 51 | F | 9 | 13 | N.D. | 10.4 | 2.39 | 2.69 | 29.6 | 43.5 | 0.84 | 0.97 | | * | * | | | | | |
| 52 | F | 4 | N.D. | N.D. | 25.1 | 4.48 | 6.73 | 29.0 | 33.1 | 0.33 | 4.22 | * | * | * | | | | | |
| 53 | M | 7 | 6 | 5 | 0.85 | 0.33 | 0.46 | 2.90 | 6.78 | 0.44 | 1.10 | * | | | | | | | |
| 54 | M | 3 | 2 | 0 | 0.04 | 0.05 | 0.05 | 0.09 | 1.90 | 0.05 | 0.00 | * | * | * | | | | | |
| 55 | F | 28 m | N.D. | N.D. | 0.48 | 0.06 | 0.08 | 3.77 | 10.1 | 0.28 | 0.31 | * | * | * | | | | | |
| 56 | M | 18 | 7 | 6 | 3.13 | 0.63 | 1.06 | 5.89 | 12.5 | 0.19 | 1.01 | * | | | | | | | |
| 57 | M | 3 | N.D. | N.D. | 0.47 | 0.40 | 0.63 | 0.91 | 2.84 | 0.49 | 1.05 | * | * | | | | | | |
| 58 | M | 17 m | 0 | 0 | 0.25 | 0.60 | 0.37 | 1.22 | 5.43 | 0.04 | 0.28 | | * | * | | | | | |
| 59 | M | 10 | N.D. | N.D. | 5.58 | 2.95 | 3.87 | 4.20 | 6.81 | 0.02 | 0.29 | * | | | | | | | |
| 60 | M | 9 | N.D. | N.D. | 0.00 | 0.01 | 0.02 | 0.02 | 0.03 | 0.20 | 0.28 | * | * | * | | | | | |
| 61 | M | 6 | N.D. | N.D. | 1.84 | 0.89 | 0.70 | 5.78 | 14.5 | 0.00 | 0.00 | * | * | * | | | | | |
| 62 | M | 29 m | 0 | 0 | 0.95 | 1.06 | 0.89 | 0.31 | 0.56 | 0.00 | 0.00 | * | | * | | | | | |

| Patient | Tolerant to FW | Anaphylaxis | Itchy throat | Angiodema | Localized urticaria | Generalized urticaria | Facial rash | Itchiness without rash | Vomiting/ Diarrhea | Abdominal pain | SOB/ Wheeze |
|---|---|---|---|---|---|---|---|---|---|---|---|
| 1 | | | * | * | | * | | | | * | |
| 2 | | | | * | | * | * | | | | |
| 3 | | | * | * | * | | * | | | | |
| 4 | | | | | | | * | | | | |
| 5 | | | * | * | | * | * | | | | |
| 6 | | | | * | | | * | * | | | |
| 7 | | * | * | | | * | | | * | * | |
| 8 | | | * | * | | | | * | | | |
| 9 | | * | * | * | | | * | | | * | * |
| 10 | | * | * | | | | | | | | * |
| 11 | | * | * | * | | | * | | * | | |
| 12 | | * | * | * | * | * | * | | * | | * |
| 13 | | | | * | | | * | * | | | |
| 14 | * | | * | | | * | * | | | | |
| 15 | | * | * | * | * | | | | * | | * |
| 16 | * | * | * | | | * | * | | * | | * |
| 17 | | | * | * | * | * | | | | | |
| 18 | | * | | * | * | | | | | | * |
| 19 | | * | | * | | * | * | | | | * |
| 20 | | | * | * | | | * | | * | | |
| 21 | | | * | | | | * | | | | |
| 22 | | | * | | * | | * | | | | |
| 23 | * | | * | * | | | * | | | | * |

TABLE 5-continued

Sensitization profile and clinical features of the study population

| | | | | | | | |
|---|---|---|---|---|---|---|---|
| 24 | * | * | | * | | | * |
| 25 | * | * | | * | * | | |
| 26 | | * | | * | | | |
| 27 | | | | * | * | * | * |
| 28 | * | * | | * | * | | * |
| 29 | * | * | | * | * | | |
| 30 | | * | * | | * | | |
| 31 | | * | | | * | | |
| 32 | | * | | | | | |
| 33 | * | * | | * | * | | * |
| 34 | | * | | * | * | * | |
| 35 | | * | | | * | | |
| 36 | | * | * | | * | * | |
| 37 | * | * | * | | * | * | * |
| 38 | * | | | | * | | |
| 39 | | * | | | | | |
| 40 | | * | | | * | | |
| 41 | * | * | | * | * | | |
| 42 | | * | | * | * | | |
| 43 | | * | | * | * | | |
| 44 | * | * | * | * | * | | |
| 45 | | | | | * | | |
| 46 | | * | * | * | | | |
| 47 | | * | | * | | | |
| 48 | * | * | | * | | * | |
| 49 | * | * | | * | | | * |
| 50 | * | * | | * | * | | * |
| 51 | * | * | | * | * | | |
| 52 | | | * | * | * | | |
| 53 | * | * | | * | | | |
| 54 | | | * | * | | | |
| 55 | | * | * | * | * | * | |
| 56 | | * | | * | | | |
| 57 | | | * | * | | | |
| 58 | * | | | * | * | | |
| 59 | * | * | | * | * | | * |
| 60 | | * | * | | | | |
| 61 | | * | | | | | |
| 62 | | * | | * | | | |

REFERENCES

1. Sicherer S H, Sampson H A. Food allergy: Epidemiology, pathogenesis, diagnosis, and treatment. J Allergy Clin Immunol 2014; 133:291-307.
2. Pawankar R. Allergic diseases and asthma: a global public health concern and a call to action. World Allergy Organ J 2014; 7:12.
3. Leung T F, Yung E, Wong Y S, Li C Y, Wong G W. Quality-of-life assessment in Chinese families with food-allergic children. Clin Exp Allergy 2009; 39:890-6.
4. Stensgaard A, Bindslev-Jensen C, Nielsen D, Munch M, DunnGalvin A. Quality of life in childhood, adolescence and adult food allergy: Patient and parent perspectives. Clin Exp Allergy 2017; 47:530-9.
5. Mehta H, Groetch M, Wang J. Growth and nutritional concerns in children with food allergy. Curr Opin Allergy Clin Immunol 2013; 13:275-9.
6. Alvares M, Kao L, Mittal V, Wuu A, Clark A, Bird J A. Misdiagnosed food allergy resulting in severe malnutrition in an infant. Pediatrics 2013; 132:e229-32.
7. Bird J A, Crain M, Varshney P. Food allergen panel testing often results in misdiagnosis of food allergy. J Pediatr 2015; 166:97-100.
8. Okada Y, Yamashita T, Kumagai H, Morikawa Y, Akasawa A. Accurate determination of childhood food allergy prevalence and correction of unnecessary avoidance. Allergy Asthma Immunol Res 2017; 9:322-8.
9. Soares-Weiser K, Takwoingi Y, Panesar S S, Muraro A, Werfel T, Hoffmann-Sommergruber K, et al. The diagnosis of food allergy: a systematic review and meta-analysis. Allergy 2014; 69:76-86.
10. Sampson H A, Gerth van Wijk R, Bindslev-Jensen C, Sicherer S, Teuber S S, Burks A W, et al. Standardizing double-blind, placebo-controlled oral food challenges: American Academy of Allergy, Asthma & Immunology-European Academy of Allergy and Clinical Immunology PRACTALL consensus report. J Allergy Clin Immunol 2012; 130:1260-74.
11. Sharp M F, Lopata A L. Fish allergy: in review. Clin Rev Allergy Immunol 2014; 46:258-71.
12. Kuehn A, Scheuermann T, Hilger C, Hentges F. Important variations in parvalbumin content in common fish species: a factor possibly contributing to variable allergenicity. Int Arch Allergy Immunol 2010; 153:359-66.
13. Kuehn A, Swoboda I, Arumugam K, Hilger C, Hentges F. Fish allergens at a glance: variable allergenicity of parvalbumins, the major fish allergens. Front Immunol 2014; 5:179.
14. Aalberse R C, Aalberse J A. Molecular allergen-specific IgE assays as a complement to allergen extract-based sensitization assessment. J Allergy Clin Immunol Pract 2015; 3:863-9.
15. Borres M P, Maruyama N, Sato S, Ebisawa M. Recent advances in component resolved diagnosis in food allergy. Allergol Int 2016; 65:378-87.
16. Bublin M, Mari A, Ebner C, Knulst A, Scheiner O, Hoffmann-Sommergruber K, et al. IgE sensitization profiles toward green and gold kiwifruits differ among patients allergic to kiwifruit from 3 European countries. J Allergy Clin Immunol 2004; 114:1169-75.
17. Fernandez-Rivas M, Bolhaar S, Gonzalez-Mancebo E, Asero R, van Leeuwen A, Bohle B, et al. Apple allergy across Europe: how allergen sensitization profiles determine the clinical expression of allergies to plant foods. J Allergy Clin Immunol 2006; 118:481-8.
18. Dominguez O, Carrillo P, Giner M, Piquer M, Alvaro M, Jimenez-Feijoo R, et al. Gad c 1 efficiency in the diagnosis of fish allergy in children. clin Transl Allergy 2013; 3:54.
19. Needham S, Funge-Smit S J. The consumption of fish and fish products in the Asia-Pacific region based on household surveys. FAO Regional Office for Asia and the Pacific, Bangkok, thailand. RAP Publication, 2015/12: 87pp.
20. Van Do T, Elsayed S, Florvaag E, Hordvik I, Endresen C. Allergy to fish parvalbumins: studies on the cross-reactivity of allergens from 9 commonly consumed fish. J Allergy Clin Immunol 2005; 116:1314-20.
21. Schulkes K J, Klemans R J, Knigge L, de Bruin-Weller M, Bruijnzeel-Koomen C A, Marknell deWitt A, et al. Specific IgE to fish extracts does not predict allergy to specific species within an adult fish allergic population. Clin Transl Allergy 2014; 4:27.
22. Komata T, Soderstrom L, Borres M P, Tachimoto H, Ebisawa M. Usefulness of wheat and soybean specific IgE antibody titers for the diagnosis of food allergy. Allergol Int 2009; 58:599-603.
23. Osterballe M, Bindslev-Jensen C. Threshold levels in food challenge and specific IgE in patients with egg allergy: is there a relationship? J Allergy Clin Immunol 2003; 112:196-201.
24. Abrams E M, Becker A B. Oral food challenge outcomes in a pediatric tertiary care center. Allergy Asthma Clin Immunol 2017; 13:43.
25. Rolinck-Werninghaus C, Niggemann B, Grabenhenrich L, Wahn U, Beyer K. Outcome of oral food challenges in children in relation to symptom-eliciting allergen dose and allergen-specific IgE. Allergy 2012; 67:951-7.
26. Novembre E, Mori F, Contestabile S, Rossi M E, Pucci N. Correlation of anti-Pru p 3 IgE levels with severity of peach allergy reactions in children. Ann Allergy Asthma Immunol 2012; 108:271-4.
27. Lieberman J A, Glaumann S, Batelson S, Borres M P, Sampson H A, Nilsson C. The utility of peanut components in the diagnosis of IgE-mediated peanut allergy among distinct populations. J Allergy Clin Immunol Pract 2013; 1:75-82.
28. Swoboda I, Bugajska-Schretter A, Verdino P, Keller W, Sperr W R, Valent P, et al. Recombinant carp parvalbumin, the major cross-reactive fish allergen: a tool for diagnosis and therapy of fish allergy. J Immunol 2002; 168:4576-84.
29. Asero R, Mistrello G, Roncarolo D, Casarini M, Falagiani P. True monosensitivity to a tropical sole. Allergy 1999; 54:1228-9.
30. Ebo D G, Kuehn A, Bridts C H, Hilger C, Hentges F, Stevens W J. Monosensitivity to pangasius and tilapia caused by allergens other than parvalbumin. J Investig Allergol Clin Immunol 2010; 20:84-8.
31. Kuehn A, Hutt-Kempf E, Hilger C, Hentges F. Clinical monosensitivity to salmonid fish linked to specific IgE-epitopes on salmon and trout beta-parvalbumins. Allergy 2011; 66:299-301.
32. Vazquez-Cortes S, Nunez-Acevedo B, Jimeno-Nogales L, Ledesma A, Fernandez-Rivas M. Selective allergy to the Salmonidae fish family: a selective parvalbumin epitope? Ann Allergy Asthma Immunol 2012; 108:62-3.
33. Luengo O, Cardona V. Component resolved diagnosis: when should it be used? Clin Transl Allergy 2014; 4:28.
34. Tuano K S, Davis C M. Utility of component-resolved diagnostics in food allergy. Curr Allergy Asthma Rep 2015; 15:32.
35. Kuehn A, Hilger C, Lehners-Weber C, Codreanu-Morel F, Morisset M, Metz-Favre C, et al. Identification of enolases and aldolases as important fish allergens in cod, salmon and tuna: component resolved diagnosis using parvalbumin and the new allergens. Clin Exp Allergy 2013; 43:811-22.

What is claimed is:

1. A polypeptide conjugate comprising a polypeptide consisting of the amino acid sequence of SEQ ID NO:1 or 2 conjugated to a heterologous moiety.

2. The polypeptide conjugate of claim 1, wherein the polypeptide consists of the amino acid sequence of SEQ ID NO:1.

3. The polypeptide conjugate of claim 1, wherein the heterologous moiety is a heterologous peptide sequence, and the polypeptide conjugate is a fusion protein.

4. The polypeptide conjugate of claim 1, wherein the heterologous moiety is a detectable label.

5. The polypeptide conjugate of claim 1, wherein the heterologous moiety is a solid substrate.

6. The polypeptide conjugate of claim 1, wherein the polypeptide consists of the amino acid sequence of SEQ ID NO:2.

7. A composition comprising (a) at least one of the polypeptide conjugate of claim 1 and (b) a physiologically acceptable excipient.

8. A method for detecting fish allergy in a subject suspected of suffering from fish allergy, comprising the steps of:
   (1) contacting a serum or plasma sample taken from the subject with the polypeptide conjugate of claim 1;
   (2) detecting in the sample presence of an IgE antibody that specifically binds to the polypeptide conjugate; and
   (3) determining the subject as likely suffering from fish allergy.

9. The method of claim 8, wherein the polypeptide is conjugated to a solid support.

10. The method of claim 8, wherein the polypeptide consists of the amino acid sequence of SEQ ID NO:1.

11. The method of claim 8, wherein the IgE antibody detected in step (2) is at a level of no less than 0.35 kUa/L.

12. The method of claim 8, wherein an anti-IgE antibody is used in step (2).

13. The method of claim 12, wherein the anti-IgE antibody is conjugated to a detectable label.

14. The method of claim 8, wherein the subject is a human.

15. The method of claim 8, wherein two polypeptide conjugates each comprising a different amino acid sequence of SEQ ID NO:1 or 2 are used in step (1).

16. The method of claim 8, further comprising a step of treating the subject for fish allergy by administration of antihistamines or corticosteroids or immunotherapy.

17. A kit for diagnosing fish allergy, comprising a first container containing the polypeptide conjugate of claim 1; and (ii) a second container containing a serum or plasma sample obtained from a control subject who is confirmed to have no fish allergy.

18. The kit of claim 17, wherein the polypeptide is conjugated to a solid support.

19. The kit of claim 17, wherein the polypeptide consists of the amino acid sequence of SEQ ID NO:1.

20. The kit of claim 17, further comprising a third container containing an anti-IgE antibody, which is optionally conjugated to a detectable label.

\* \* \* \* \*

SEQUENCE LISTING

<160> NUMBER OF SEQ ID NOS: 15

<210> SEQ ID NO 1
<211> LENGTH: 109
<212> TYPE: PRT
<213> ORGANISM: Ctenopharyngodon idella

<400> SEQUENCE: 1

```
Met Ala Phe Ala Gly Val Leu Asn Asp Ala Asp Ile Ala Ala Ala Leu
1               5                   10                  15

Glu Ala Cys Lys Ala Ala Asp Ser Phe Asn His Lys Ala Phe Phe Ala
            20                  25                  30

Lys Val Gly Leu Ser Ala Lys Ser Gly Asp Asp Val Lys Lys Ala Phe
        35                  40                  45

Ala Ile Ile Asp Gln Asp Lys Ser Gly Phe Ile Glu Glu Asp Glu Leu
    50                  55                  60

Lys Leu Phe Leu Gln Asn Phe Lys Ala Asp Ala Arg Ala Leu Thr Asp
65                  70                  75                  80

Ala Glu Thr Lys Ile Phe Leu Lys Ala Gly Asp Ser Asp Gly Asp Gly
            85                  90                  95
```

```
Lys Ile Gly Val Asp Glu Phe Ala Ala Leu Val Lys Ala
            100                 105

<210> SEQ ID NO 2
<211> LENGTH: 433
<212> TYPE: PRT
<213> ORGANISM: Ctenopharyngodon idella

<400> SEQUENCE: 2

Met Ser Ile Ser Lys Ile His Ala Arg Glu Ile Leu Asp Ser Arg Gly
1               5                   10                  15

Asn Pro Thr Val Glu Val Asp Leu Tyr Thr Ser Lys Gly Arg Phe Arg
            20                  25                  30

Ala Ala Val Pro Ser Gly Ala Ser Thr Gly Val His Glu Ala Leu Glu
        35                  40                  45

Leu Arg Asp Gly Asp Lys Thr Arg Tyr Leu Gly Lys Gly Thr Gln Lys
    50                  55                  60

Ala Val Asp His Val Asn Lys Glu Ile Ala Pro Lys Leu Ile Glu Lys
65                  70                  75                  80

Lys Phe Ser Val Val Asp Gln Glu Lys Ile Asp Lys Phe Met Leu Glu
                85                  90                  95

Leu Asp Gly Thr Glu Asn Lys Ser Lys Phe Gly Ala Asn Ala Ile Leu
            100                 105                 110

Gly Val Ser Leu Ala Val Cys Lys Ala Gly Ala Ala Glu Lys Gly Val
        115                 120                 125

Pro Leu Tyr Arg His Ile Ala Asp Leu Ala Gly Asn Lys Asp Val Ile
    130                 135                 140

Leu Pro Val Pro Ala Phe Asn Val Ile Asn Gly Gly Ser His Ala Gly
145                 150                 155                 160

Asn Lys Leu Ala Met Gln Glu Phe Met Ile Leu Pro Val Gly Ala Lys
                165                 170                 175

Asn Phe His Glu Ala Met Arg Ile Gly Ala Glu Val Tyr His Asn Leu
            180                 185                 190

Lys Asn Val Ile Lys Ala Lys Tyr Gly Lys Asp Ala Thr Asn Val Gly
        195                 200                 205

Asp Glu Gly Gly Phe Ala Pro Asn Ile Leu Glu Asn Asn Glu Ala Leu
    210                 215                 220

Glu Leu Leu Lys Ser Ala Ile Glu Lys Ala Gly Tyr Pro Asp Lys Ile
225                 230                 235                 240

Ile Ile Gly Met Asp Val Ala Ala Ser Glu Phe Phe Lys Ser Gly Lys
                245                 250                 255

Tyr Asp Leu Asp Phe Lys Ser Pro Asp Pro Lys Arg His Ile Thr
            260                 265                 270

Gly Glu Gln Leu Gly Asp Leu Tyr Lys Ser Phe Ile Lys Asn Tyr Pro
        275                 280                 285

Val Gln Ser Ile Glu Asp Pro Phe Asp Gln Asp Trp Glu Asn Trp
    290                 295                 300

Ser Lys Phe Thr Gly Ser Val Asp Ile Gln Val Val Gly Asp Asp Leu
305                 310                 315                 320

Thr Val Thr Asn Pro Lys Arg Ile Gln Gln Ala Cys Glu Lys Lys Ala
                325                 330                 335

Cys Asn Cys Leu Leu Leu Lys Val Asn Gln Ile Gly Ser Val Thr Glu
            340                 345                 350

Ser Ile Gln Ala Cys Lys Leu Ala Gln Ser Asn Gly Trp Gly Val Met
```

```
              355                 360                 365
Val Ser His Arg Ser Gly Glu Thr Glu Asp Thr Phe Ile Ala Asp Leu
    370                 375                 380

Val Val Gly Leu Cys Thr Gly Gln Ile Lys Thr Gly Ala Pro Cys Arg
385                 390                 395                 400

Ser Glu Arg Leu Ala Lys Tyr Asn Gln Leu Met Arg Ile Glu Glu Glu
                405                 410                 415

Leu Gly Asp Lys Ala Lys Phe Ala Gly Lys Asp Phe Arg His Pro Lys
            420                 425                 430

Leu

<210> SEQ ID NO 3
<211> LENGTH: 364
<212> TYPE: PRT
<213> ORGANISM: Ctenopharyngodon idella

<400> SEQUENCE: 3

Met Pro His Ala Tyr Pro Phe Leu Thr Pro Glu Gln Lys Lys Glu Leu
1               5                   10                  15

Ser Asp Ile Ala Leu Arg Ile Val Ala Pro Gly Lys Gly Ile Leu Ala
            20                  25                  30

Ala Asp Glu Ser Thr Gly Ser Val Ala Lys Arg Phe Gln Ser Ile Asn
        35                  40                  45

Ala Glu Asn Thr Glu Glu Asn Arg Arg Leu Tyr Arg Gln Leu Leu Phe
    50                  55                  60

Thr Ala Asp Asp Arg Val Lys Pro Cys Ile Gly Gly Val Ile Leu Phe
65                  70                  75                  80

His Glu Thr Leu Tyr Gln Lys Ala Asp Asp Gly Lys Leu Phe Ser Gln
                85                  90                  95

Leu Leu Lys Glu Arg Gly Met Val Val Gly Ile Lys Val Asp Lys Gly
            100                 105                 110

Val Val Pro Leu Ala Gly Thr Asn Gly Glu Thr Thr Thr Gln Gly Leu
        115                 120                 125

Asp Gly Leu Tyr Glu Arg Cys Ala Gln Tyr Lys Lys Asp Gly Ala Asp
    130                 135                 140

Phe Ala Lys Trp Arg Cys Val Leu Lys Ile Thr Ser Thr Thr Pro Ser
145                 150                 155                 160

Arg Leu Ala Ile Ile Glu Asn Ala Asn Val Leu Ala Arg Tyr Ala Ser
                165                 170                 175

Ile Cys Gln Met His Gly Ile Val Pro Ile Val Glu Pro Glu Ile Leu
            180                 185                 190

Pro Asp Gly Asp His Asp Leu Lys Arg Cys Gln Tyr Val Thr Glu Lys
        195                 200                 205

Val Leu Ala Ala Val Tyr Lys Ala Leu Ser Asp His His Val Tyr Leu
    210                 215                 220

Glu Gly Thr Leu Leu Lys Pro Asn Met Val Thr Ala Gly His Ser Cys
225                 230                 235                 240

Ser Gln Lys Asn Thr Pro Gln Glu Ile Ala Met Ala Thr Val Thr Ala
                245                 250                 255

Leu Arg Arg Thr Val Pro Pro Ala Val Pro Gly Ile Thr Phe Leu Ser
            260                 265                 270

Gly Gly Gln Ser Glu Glu Glu Ala Thr Leu Asn Leu Asn Ala Met Asn
        275                 280                 285

Lys Cys Pro Leu His Arg Pro Trp Ala Leu Thr Phe Ser Tyr Gly Arg
```

```
            290                 295                 300

Ala Leu Gln Ala Ser Ala Leu Lys Ala Trp Gly Gly Lys Lys Glu Asn
305                 310                 315                 320

Gly Lys Ala Cys Gln Glu Glu Phe Ile Lys Arg Ala Leu Asn Asn Ser
                325                 330                 335

Leu Ala Cys Val Gly Lys Tyr Val Ser Ser Gly Asp Lys Gly Ala Ala
            340                 345                 350

Ala Gly Glu Ser Leu Phe Val Ala Asn His Ala Tyr
        355                 360

<210> SEQ ID NO 4
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 4

His His His His His His
1               5

<210> SEQ ID NO 5
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Met Ala Phe Ala Gly Ile Leu Asn Glu Ala Asp Ile Thr Ala Ala Leu
1               5                   10                  15

Gln Ala Cys Gln Ala Ala Asp Ser Phe Lys Tyr Lys Asp Phe Phe Ala
            20                  25                  30

Lys Val Gly Leu Thr Ala Lys Ser Ser Asp Asp Ile Lys Lys Ala Phe
        35                  40                  45

Ala Val Ile Asp Gln Asp Lys Ser Gly Phe Ile Glu Glu Glu Glu Leu
    50                  55                  60

Lys Leu Phe Leu Gln Asn Phe Ser Ala Gly Ala Arg Ala Leu Thr Asp
65                  70                  75                  80

Ala Glu Thr Lys Ala Phe Leu Lys Ala Gly Asp Ser Asp Gly Asp Gly
            85                  90                  95

Lys Ile Gly Val Asp Glu Phe Ala Val Leu Val Lys Ala
        100                 105

<210> SEQ ID NO 6
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Met Ala Ile Thr Asp Val Leu Ala Ala Ser Asp Ile Ser Thr Ala Ile
1               5                   10                  15

Asn Ala Cys Lys Ala Lys Asp Ser Phe Ser Pro Arg Thr Phe Phe Ala
            20                  25                  30

Thr Val Gly Leu Ser Lys Lys Ser Pro Arg Glu Ile Glu Lys Ile Phe
        35                  40                  45
```

```
Lys Met Leu Asp Gln Asp Lys Ser Gly Phe Ile Glu Gln Asp Glu Leu
        50                  55                  60

Gln Leu Phe Leu Gln Asn Phe Ser Lys Gly Ala Arg Ala Leu Thr Ala
 65                  70                  75                  80

Ala Glu Thr Lys Ala Phe Leu Met Ala Gly Asp Met Asp Gly Asp Gly
                85                  90                  95

Lys Ile Gly Trp Glu Glu Phe Ser Ala Leu Val Asn Ala
                100                 105

<210> SEQ ID NO 7
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Met Ala Ile Thr Asp Val Leu Ala Ala Ser Asp Ile Ser Thr Ala Ile
 1               5                   10                  15

Asn Ala Cys Lys Ala Lys Asp Ser Phe Ser Pro Arg Thr Phe Phe Ala
                20                  25                  30

Thr Val Gly Leu Ser Lys Lys Ser Pro Arg Glu Ile Glu Lys Ile Phe
            35                  40                  45

Lys Met Leu Asp Gln Asp Lys Ser Gly Phe Ile Glu Gln Asp Glu Leu
        50                  55                  60

Gln Leu Phe Leu Gln Asn Phe Ser Lys Gly Ala Arg Ala Leu Thr Ala
 65                  70                  75                  80

Ala Glu Thr Lys Ala Phe Leu Met Ala Gly Asp Met Asp Gly Asp Gly
                85                  90                  95

Lys Ile Gly Trp Glu Glu Phe Ser Ala Leu Val Asn Ala
                100                 105

<210> SEQ ID NO 8
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Met Ala Phe Ala Gly Val Leu Asn Asp Ala Asp Ile Ala Ala Ala Leu
 1               5                   10                  15

Glu Ala Cys Lys Ala Ala Asp Ser Phe Asn His Lys Ala Phe Phe Ala
                20                  25                  30

Lys Val Gly Leu Ser Ala Lys Ser Gly Asp Asp Val Lys Ala Phe
            35                  40                  45

Ala Ile Ile Asp Gln Asp Lys Ser Gly Phe Ile Glu Glu Asp Glu Leu
        50                  55                  60

Lys Leu Phe Leu Gln Asn Phe Lys Ala Asp Ala Arg Ala Leu Thr Asp
 65                  70                  75                  80

Ala Glu Thr Lys Ile Phe Leu Lys Ala Gly Asp Ser Asp Gly Asp Gly
                85                  90                  95

Lys Ile Gly Val Asp Glu Phe Ala Ala Leu Val Lys Ala
                100                 105

<210> SEQ ID NO 9
```

```
<211> LENGTH: 433
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Met Ser Ile Ser Lys Ile His Ala Arg Glu Ile Leu Asp Ser Arg Gly
1               5                   10                  15

Asn Pro Thr Val Glu Val Asp Leu Tyr Thr Ser Lys Gly Arg Phe Arg
            20                  25                  30

Ala Ala Val Pro Ser Gly Ala Ser Thr Gly Val His Glu Ala Leu Glu
        35                  40                  45

Leu Arg Asp Gly Asp Lys Thr Arg Tyr Leu Gly Lys Gly Thr Gln Lys
    50                  55                  60

Ala Val Asp His Val Asn Lys Glu Ile Ala Pro Lys Leu Ile Glu Lys
65                  70                  75                  80

Lys Phe Ser Val Val Asp Gln Glu Lys Ile Asp Lys Phe Met Leu Glu
                85                  90                  95

Leu Asp Gly Thr Glu Asn Lys Ser Lys Phe Gly Ala Asn Ala Ile Leu
            100                 105                 110

Gly Val Ser Leu Ala Val Cys Lys Ala Gly Ala Ala Glu Lys Gly Val
        115                 120                 125

Pro Leu Tyr Arg His Ile Ala Asp Leu Ala Gly Asn Lys Asp Val Ile
    130                 135                 140

Leu Pro Val Pro Ala Phe Asn Val Ile Asn Gly Gly Ser His Ala Gly
145                 150                 155                 160

Asn Lys Leu Ala Met Gln Glu Phe Met Ile Leu Pro Val Gly Ala Lys
                165                 170                 175

Asn Phe His Glu Ala Met Arg Ile Gly Ala Glu Val Tyr His Asn Leu
            180                 185                 190

Lys Asn Val Ile Lys Ala Lys Tyr Gly Lys Asp Ala Thr Asn Val Gly
        195                 200                 205

Asp Glu Gly Gly Phe Ala Pro Asn Ile Leu Glu Asn Asn Glu Ala Leu
    210                 215                 220

Glu Leu Leu Lys Ser Ala Ile Glu Lys Ala Gly Tyr Pro Asp Lys Ile
225                 230                 235                 240

Ile Ile Gly Met Asp Val Ala Ala Ser Glu Phe Phe Lys Ser Gly Lys
                245                 250                 255

Tyr Asp Leu Asp Phe Lys Ser Pro Asp Asp Pro Lys Arg His Ile Thr
            260                 265                 270

Gly Glu Gln Leu Gly Asp Leu Tyr Lys Ser Phe Ile Lys Asn Tyr Pro
        275                 280                 285

Val Gln Ser Ile Glu Asp Pro Phe Asp Gln Asp Asp Trp Glu Asn Trp
    290                 295                 300

Ser Lys Phe Thr Gly Ser Val Asp Ile Gln Val Val Gly Asp Asp Leu
305                 310                 315                 320

Thr Val Thr Asn Pro Lys Arg Ile Gln Gln Ala Cys Glu Lys Lys Ala
                325                 330                 335

Cys Asn Cys Leu Leu Leu Lys Val Asn Gln Ile Gly Ser Val Thr Glu
            340                 345                 350

Ser Ile Gln Ala Cys Lys Leu Ala Gln Ser Asn Gly Trp Gly Val Met
        355                 360                 365

Val Ser His Arg Ser Gly Glu Thr Glu Asp Thr Phe Ile Ala Asp Leu
```

```
                    370                 375                 380
Val Val Gly Leu Cys Thr Gly Gln Ile Lys Thr Gly Ala Pro Cys Arg
385                 390                 395                 400

Ser Glu Arg Leu Ala Lys Tyr Asn Gln Leu Met Arg Ile Glu Glu Glu
                405                 410                 415

Leu Gly Asp Lys Ala Lys Phe Ala Gly Lys Asp Phe Arg His Pro Lys
            420                 425                 430

Leu

<210> SEQ ID NO 10
<211> LENGTH: 433
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Met Ser Ile Ser Lys Ile His Ala Arg Glu Ile Leu Asp Ser Arg Gly
1               5                   10                  15

Asn Pro Thr Val Glu Val Asp Leu Tyr Thr Ser Lys Gly Arg Phe Arg
                20                  25                  30

Ala Ala Val Pro Ser Gly Ala Ser Thr Gly Val His Glu Ala Leu Glu
            35                  40                  45

Leu Arg Asp Gly Asp Lys Thr Arg Tyr Leu Gly Lys Gly Thr Gln Lys
        50                  55                  60

Ala Val Asp His Val Asn Lys Glu Ile Ala Pro Lys Leu Ile Glu Lys
65                  70                  75                  80

Lys Phe Ser Val Val Asp Gln Glu Lys Ile Asp Lys Phe Met Leu Glu
                85                  90                  95

Leu Asp Gly Thr Glu Asn Lys Ser Lys Phe Gly Ala Asn Ala Ile Leu
                100                 105                 110

Gly Val Ser Leu Ala Val Cys Lys Ala Gly Ala Ala Glu Lys Gly Val
            115                 120                 125

Pro Leu Tyr Arg His Ile Ala Asp Leu Ala Gly Asn Lys Asp Val Ile
        130                 135                 140

Leu Pro Val Pro Ala Phe Asn Val Ile Asn Gly Gly Ser His Ala Gly
145                 150                 155                 160

Asn Lys Leu Ala Met Gln Glu Phe Met Ile Leu Pro Val Gly Ala Lys
                165                 170                 175

Asn Phe His Glu Ala Met Arg Ile Gly Ala Glu Val Tyr His Asn Leu
            180                 185                 190

Lys Asn Val Ile Lys Ala Lys Tyr Gly Lys Asp Ala Thr Asn Val Gly
        195                 200                 205

Asp Glu Gly Gly Phe Ala Pro Asn Ile Leu Glu Asn Asn Glu Ala Leu
    210                 215                 220

Glu Leu Leu Lys Ser Ala Ile Glu Lys Ala Gly Tyr Pro Asp Lys Ile
225                 230                 235                 240

Ile Ile Gly Met Asp Val Ala Ala Ser Glu Phe Phe Lys Ser Gly Lys
                245                 250                 255

Tyr Asp Leu Asp Phe Lys Ser Pro Asp Pro Lys Arg His Ile Thr
            260                 265                 270

Gly Glu Gln Leu Gly Asp Leu Tyr Lys Ser Phe Ile Lys Asn Tyr Pro
        275                 280                 285

Val Gln Ser Ile Glu Asp Pro Phe Asp Gln Asp Asp Trp Glu Asn Trp
```

```
                290                 295                 300

Ser Lys Phe Thr Gly Ser Val Asp Ile Gln Val Val Gly Asp Asp Leu
305                 310                 315                 320

Thr Val Thr Asn Pro Lys Arg Ile Gln Gln Ala Cys Glu Lys Lys Ala
                325                 330                 335

Cys Asn Cys Leu Leu Lys Val Asn Gln Ile Gly Ser Val Thr Glu
            340                 345                 350

Ser Ile Gln Ala Cys Lys Leu Ala Gln Ser Asn Gly Trp Gly Val Met
        355                 360                 365

Val Ser His Arg Ser Gly Glu Thr Glu Asp Thr Phe Ile Ala Asp Leu
    370                 375                 380

Val Val Gly Leu Cys Thr Gly Gln Ile Lys Thr Gly Ala Pro Cys Arg
385                 390                 395                 400

Ser Glu Arg Leu Ala Lys Tyr Asn Gln Leu Met Arg Ile Glu Glu Glu
                405                 410                 415

Leu Gly Asp Lys Ala Lys Phe Ala Gly Lys Asp Phe Arg His Pro Lys
            420                 425                 430

Leu

<210> SEQ ID NO 11
<211> LENGTH: 431
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Met Ser Ile Leu Lys Ile His Ala Arg Glu Ile Phe Asp Ser Arg Gly
1               5                   10                  15

Asn Pro Thr Val Glu Val Asp Leu Tyr Thr Lys Lys Gly Leu Phe Arg
            20                  25                  30

Ala Ala Val Pro Ser Gly Ala Ser Thr Gly Ile Tyr Glu Ala Leu Glu
        35                  40                  45

Leu Arg Asp Asn Asp Lys Thr Arg Tyr Met Gly Lys Gly Val Ser Lys
    50                  55                  60

Ala Val Glu His Ile Asn Lys Thr Ile Ala Pro Ala Leu Val Ser Gln
65              70                  75                  80

Ser Val Ser Val Leu Glu Gln Glu Lys Ile Asp Lys Leu Met Leu Asp
                85                  90                  95

Met Asp Gly Thr Glu Asn Lys Ser Lys Phe Gly Ala Asn Ala Ile Leu
            100                 105                 110

Gly Val Ser Leu Ala Val Cys Lys Ala Gly Ala Ala Glu Lys Gly Val
        115                 120                 125

Pro Leu Tyr Arg His Ile Ala Asp Leu Ala Gly Asn Pro Glu Val Ile
    130                 135                 140

Leu Pro Val Pro Ala Phe Asn Val Ile Asn Gly Gly Ser His Ala Gly
145                 150                 155                 160

Asn Lys Leu Ala Met Gln Glu Phe Met Ile Leu Pro Ile Gly Ala Ser
                165                 170                 175

Asn Phe Lys Glu Ala Met Arg Ile Gly Ala Glu Val Tyr His Asn Leu
            180                 185                 190

Lys Asn Val Ile Lys Glu Lys Tyr Gly Lys Asp Ala Thr Asn Val Gly
        195                 200                 205

Asp Glu Gly Gly Phe Ala Pro Asn Ile Leu Glu Asn Lys Glu Ala Leu
```

Glu Leu Leu Lys Asn Ala Ile Ser Lys Ala Gly Tyr Thr Asp Lys Ile
225                 230                 235                 240

Val Ile Gly Met Asp Val Ala Ala Ser Glu Phe Tyr Lys Gly Gly Lys
            245                 250                 255

Tyr Asp Leu Asp Phe Lys Ser Pro Asp Pro Ser Arg Tyr Ile Ser
            260                 265                 270

Pro Asp Gln Leu Ala Asp Leu Tyr Arg Ser Phe Val Lys Asp Tyr Pro
        275                 280                 285

Val Val Ser Ile Glu Asp Pro Phe Asp Gln Asp Asp Trp Glu Ala Trp
    290                 295                 300

Thr Asn Phe Thr Ala Ser Thr Asn Ile Gln Val Val Gly Asp Asp Leu
305                 310                 315                 320

Thr Val Thr Asn Pro Lys Arg Ile Ala Lys Ala Val Ser Asp Lys Ala
                325                 330                 335

Cys Asn Cys Leu Leu Leu Lys Val Asn Gln Ile Gly Ser Val Thr Glu
            340                 345                 350

Ser Leu Gln Ala Cys Lys Met Ala Gln Ser Asn Gly Trp Gly Val Met
        355                 360                 365

Val Ser His Arg Ser Gly Glu Thr Glu Asp Thr Phe Ile Ala Asp Leu
    370                 375                 380

Val Val Gly Leu Cys Thr Gly Gln Ile Lys Thr Gly Ala Pro Cys Arg
385                 390                 395                 400

Ser Glu Arg Leu Ala Lys Tyr Asn Gln Leu Leu Arg Ile Glu Glu Glu
                405                 410                 415

Leu Gly Asp Lys Ala Arg Phe Ala Gly Lys Asn Phe Arg Arg Pro
            420                 425                 430

<210> SEQ ID NO 12
<211> LENGTH: 364
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Met Pro His Ala Tyr Pro Phe Leu Thr Pro Glu Gln Lys Lys Glu Leu
1               5                   10                  15

Ser Asp Ile Ala Leu Arg Ile Val Ala Pro Gly Lys Gly Ile Leu Ala
            20                  25                  30

Ala Asp Glu Ser Thr Gly Ser Val Ala Lys Arg Phe Gln Ser Ile Asn
        35                  40                  45

Ala Glu Asn Thr Glu Glu Asn Arg Arg Leu Tyr Arg Gln Leu Leu Phe
    50                  55                  60

Thr Ala Asp Asp Arg Val Lys Pro Cys Ile Gly Gly Val Ile Leu Phe
65                  70                  75                  80

His Glu Thr Leu Tyr Gln Lys Ala Asp Asp Gly Lys Leu Phe Ser Gln
                85                  90                  95

Leu Leu Lys Glu Arg Gly Met Val Val Gly Ile Lys Val Asp Lys Gly
            100                 105                 110

Val Val Pro Leu Ala Gly Thr Asn Gly Glu Thr Thr Thr Gln Gly Leu
        115                 120                 125

Asp Gly Leu Tyr Glu Arg Cys Ala Gln Tyr Lys Lys Asp Gly Ala Asp
    130                 135                 140

```
Phe Ala Lys Trp Arg Cys Val Leu Lys Ile Thr Ser Thr Thr Pro Ser
145                 150                 155                 160

Arg Leu Ala Ile Ile Glu Asn Ala Asn Val Leu Ala Arg Tyr Ala Ser
                165                 170                 175

Ile Cys Gln Met His Gly Ile Val Pro Ile Val Glu Pro Glu Ile Leu
            180                 185                 190

Pro Asp Gly Asp His Asp Leu Lys Arg Cys Gln Tyr Val Thr Glu Lys
        195                 200                 205

Val Leu Ala Ala Val Tyr Lys Ala Leu Ser Asp His His Val Tyr Leu
    210                 215                 220

Glu Gly Thr Leu Leu Lys Pro Asn Met Val Thr Ala Gly His Ser Cys
225                 230                 235                 240

Ser Gln Lys Asn Thr Pro Gln Glu Ile Ala Met Ala Thr Val Thr Ala
                245                 250                 255

Leu Arg Arg Thr Val Pro Pro Ala Val Pro Gly Ile Thr Phe Leu Ser
            260                 265                 270

Gly Gly Gln Ser Glu Glu Glu Ala Thr Leu Asn Leu Asn Ala Met Asn
        275                 280                 285

Lys Cys Pro Leu His Arg Pro Trp Ala Leu Thr Phe Ser Tyr Gly Arg
290                 295                 300

Ala Leu Gln Ala Ser Ala Leu Lys Ala Trp Gly Gly Lys Lys Glu Asn
305                 310                 315                 320

Gly Lys Ala Cys Gln Glu Phe Ile Lys Arg Ala Leu Asn Asn Ser
                325                 330                 335

Leu Ala Cys Val Gly Lys Tyr Val Ser Ser Gly Asp Lys Gly Ala Ala
            340                 345                 350

Ala Gly Glu Ser Leu Phe Val Ala Asn His Ala Tyr
        355                 360

<210> SEQ ID NO 13
<211> LENGTH: 364
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Met Pro His Ala Tyr Pro Phe Leu Thr Pro Glu Gln Lys Lys Glu Leu
1               5                   10                  15

Ser Asp Ile Ala Leu Arg Ile Val Ala Pro Gly Lys Gly Ile Leu Ala
            20                  25                  30

Ala Asp Glu Ser Thr Gly Ser Val Ala Lys Arg Phe Gln Ser Ile Asn
        35                  40                  45

Ala Glu Asn Thr Glu Glu Asn Arg Arg Leu Tyr Arg Gln Leu Leu Phe
    50                  55                  60

Thr Ala Asp Asp Arg Val Lys Pro Cys Ile Gly Gly Val Ile Leu Phe
65                  70                  75                  80

His Glu Thr Leu Tyr Gln Lys Ala Asp Asp Gly Lys Leu Phe Ser Gln
                85                  90                  95

Leu Leu Lys Glu Arg Gly Met Val Val Gly Ile Lys Val Asp Lys Gly
            100                 105                 110

Val Val Pro Leu Ala Gly Thr Asn Gly Glu Thr Thr Thr Gln Gly Leu
        115                 120                 125

Asp Gly Leu Tyr Glu Arg Cys Ala Gln Tyr Lys Lys Asp Gly Ala Asp
    130                 135                 140
```

Phe Ala Lys Trp Arg Cys Val Leu Lys Ile Thr Ser Thr Thr Pro Ser
145                 150                 155                 160

Arg Leu Ala Ile Ile Glu Asn Ala Asn Val Leu Ala Arg Tyr Ala Ser
            165                 170                 175

Ile Cys Gln Met His Gly Ile Val Pro Ile Val Glu Pro Glu Ile Leu
        180                 185                 190

Pro Asp Gly Asp His Asp Leu Lys Arg Cys Gln Tyr Val Thr Glu Lys
    195                 200                 205

Val Leu Ala Ala Val Tyr Lys Ala Leu Ser Asp His His Val Tyr Leu
210                 215                 220

Glu Gly Thr Leu Leu Lys Pro Asn Met Val Thr Ala Gly His Ser Cys
225                 230                 235                 240

Ser Gln Lys Asn Thr Pro Gln Glu Ile Ala Met Ala Thr Val Thr Ala
            245                 250                 255

Leu Arg Arg Thr Val Pro Pro Ala Val Pro Gly Ile Thr Phe Leu Ser
        260                 265                 270

Gly Gly Gln Ser Glu Glu Ala Thr Leu Asn Leu Asn Ala Met Asn
    275                 280                 285

Lys Cys Pro Leu His Arg Pro Trp Ala Leu Thr Phe Ser Tyr Gly Arg
290                 295                 300

Ala Leu Gln Ala Ser Ala Leu Lys Ala Trp Gly Gly Lys Lys Glu Asn
305                 310                 315                 320

Gly Lys Ala Cys Gln Glu Glu Phe Ile Lys Arg Ala Leu Asn Asn Ser
            325                 330                 335

Leu Ala Cys Val Gly Lys Tyr Val Ser Ser Gly Asp Lys Gly Ala Ala
        340                 345                 350

Ala Gly Glu Ser Leu Phe Val Ala Asn His Ala Tyr
    355                 360

<210> SEQ ID NO 14
<211> LENGTH: 363
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 14

Met Thr His Gln Tyr Pro Ala Leu Thr Thr Glu Gln Lys Lys Glu Leu
1               5                   10                  15

Gln Asp Ile Ala Gln Arg Ile Val Ala Pro Gly Lys Gly Ile Leu Ala
            20                  25                  30

Ala Asp Glu Ser Thr Gly Ser Met Ala Lys Arg Leu Asn Pro Ile Gly
        35                  40                  45

Val Glu Asn Thr Glu Glu Asn Arg Arg Leu Tyr Arg Gln Ile Leu Phe
50                  55                  60

Ser Ala Asp Glu Arg Ile Asp Lys Cys Ile Gly Gly Val Ile Phe Phe
65                  70                  75                  80

His Glu Thr Leu Tyr Gln Asn Ala Asp Asp Gly Thr Cys Phe Ala Lys
                85                  90                  95

Met Ile Lys Asp Arg Gly Ile Val Val Gly Ile Lys Val Asp Lys Gly
            100                 105                 110

Val Val Pro Leu Ala Gly Thr Asn Gly Glu Thr Thr Thr Gln Gly Leu
        115                 120                 125

Asp Gly Leu Ser Glu Arg Cys Ala Gln Tyr Lys Lys Asp Gly Ala Asp

```
                    130                 135                 140
Phe Ala Lys Trp Arg Cys Val Leu Lys Ile Ser Asp Thr Thr Pro Ser
145                 150                 155                 160

Glu Leu Ala Ile Met Glu Asn Ala Asn Val Leu Ala Arg Tyr Ala Ser
                165                 170                 175

Ile Cys Gln Gln Asn Gly Ile Val Pro Ile Val Glu Pro Glu Ile Leu
                180                 185                 190

Pro Asp Gly Asp His Asp Leu Lys Arg Cys Gln Tyr Val Thr Glu Lys
            195                 200                 205

Val Leu Ala Ala Cys Tyr Lys Ala Leu Ser Asp His His Val Tyr Leu
        210                 215                 220

Glu Gly Thr Leu Leu Lys Pro Asn Met Val Thr Ala Gly His Ser Cys
225                 230                 235                 240

Pro Thr Lys Tyr Asn Ser Gln Glu Ile Ala Met Ala Thr Val Thr Ala
                245                 250                 255

Leu Arg Arg Thr Val Pro Pro Ala Val Thr Gly Val Thr Phe Leu Ser
                260                 265                 270

Gly Gly Gln Ser Glu Glu Glu Ala Ser Val Asn Leu Asn Ala Ile Asn
            275                 280                 285

Asn Cys Pro Leu Ala Lys Pro Trp Ala Leu Thr Phe Ser Tyr Gly Arg
        290                 295                 300

Ala Leu Gln Ala Ser Ala Leu Ala Ala Trp Arg Gly Val Lys Asp Asn
305                 310                 315                 320

Glu Lys Ala Ala Thr Glu Ala Phe Ile Gln Arg Ala Glu Ala Asn Gly
                325                 330                 335

Leu Ala Ala Gln Gly Lys Tyr Val Ser Ser Gly Thr Asp Gly Ala Ala
                340                 345                 350

Gly Gln Ser Leu Tyr Val Ala Asn His Ala Tyr
            355                 360

<210> SEQ ID NO 15
<211> LENGTH: 363
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Met Thr His Gln Tyr Pro Ala Leu Thr Thr Glu Gln Lys Lys Glu Leu
1               5                   10                  15

Gln Asp Ile Ala Gln Arg Ile Val Ala Pro Gly Lys Gly Ile Leu Ala
                20                  25                  30

Ala Asp Glu Ser Thr Gly Ser Met Ala Lys Arg Leu Asn Pro Ile Gly
            35                  40                  45

Val Glu Asn Thr Glu Glu Asn Arg Arg Leu Tyr Arg Gln Ile Leu Phe
        50                  55                  60

Ser Ala Asp Glu Arg Ile Asp Lys Cys Ile Gly Val Ile Phe Phe
65                  70                  75                  80

His Glu Thr Leu Tyr Gln Asn Ala Asp Asp Gly Thr Cys Phe Ala Lys
                85                  90                  95

Met Ile Lys Asp Arg Gly Ile Val Val Gly Ile Lys Val Asp Lys Gly
                100                 105                 110

Val Val Pro Leu Ala Gly Thr Asn Gly Glu Thr Thr Thr Gln Gly Leu
            115                 120                 125
```

```
Asp Gly Leu Ser Glu Arg Cys Ala Gln Tyr Lys Lys Asp Gly Ala Asp
        130                 135                 140

Phe Ala Lys Trp Arg Cys Val Leu Lys Ile Ser Asp Thr Thr Pro Ser
145                 150                 155                 160

Glu Leu Ala Ile Met Glu Asn Ala Asn Val Leu Ala Arg Tyr Ala Ser
                165                 170                 175

Ile Cys Gln Gln Asn Gly Ile Val Pro Ile Val Glu Pro Glu Ile Leu
                180                 185                 190

Pro Asp Gly Asp His Asp Leu Lys Arg Cys Gln Tyr Val Thr Glu Lys
            195                 200                 205

Val Leu Ala Ala Cys Tyr Lys Ala Leu Ser Asp His His Val Tyr Leu
        210                 215                 220

Glu Gly Thr Leu Leu Lys Pro Asn Met Val Thr Ala Gly His Ser Cys
225                 230                 235                 240

Pro Thr Lys Tyr Asn Ser Gln Glu Ile Ala Met Ala Thr Val Thr Ala
                245                 250                 255

Leu Arg Arg Thr Val Pro Pro Ala Val Thr Gly Val Thr Phe Leu Ser
                260                 265                 270

Gly Gly Gln Ser Glu Glu Glu Ala Ser Val Asn Leu Asn Ala Ile Asn
            275                 280                 285

Asn Cys Pro Leu Ala Lys Pro Trp Ala Leu Thr Phe Ser Tyr Gly Arg
290                 295                 300

Ala Leu Gln Ala Ser Ala Leu Ala Ala Trp Arg Gly Val Lys Asp Asn
305                 310                 315                 320

Glu Lys Ala Ala Thr Glu Ala Phe Ile Gln Arg Ala Glu Ala Asn Gly
                325                 330                 335

Leu Ala Ala Gln Gly Lys Tyr Val Ser Ser Gly Thr Asp Gly Ala Ala
                340                 345                 350

Gly Gln Ser Leu Tyr Val Ala Asn His Ala Tyr
            355                 360
```